US010314733B2

(12) United States Patent
Hyde et al.

(10) Patent No.: US 10,314,733 B2
(45) Date of Patent: Jun. 11, 2019

(54) SENSOR-BASED CONTROL OF ACTIVE WEARABLE SYSTEM

(71) Applicant: Elwha LLC, Belleveue, WA (US)

(72) Inventors: Roderick A. Hyde, Redmond, WA (US); Jordin T. Kare, San Jose, CA (US); Dennis J. Rivet, Richmond, VA (US); Suzanne Kathleen Scheele, Kirkland, WA (US); Katherine E. Sharadin, Redmond, WA (US); Lowell L. Wood, Jr., Bellevue, WA (US)

(73) Assignee: Elwha LLC, Bellevue, WA (US)

( * ) Notice: Subject to any disclaimer, the term of this patent is extended or adjusted under 35 U.S.C. 154(b) by 267 days.

(21) Appl. No.: 15/161,599

(22) Filed: May 23, 2016

(65) Prior Publication Data
US 2016/0324677 A1 Nov. 10, 2016

Related U.S. Application Data

(63) Continuation-in-part of application No. 13/739,868, filed on Jan. 11, 2013, now Pat. No. 9,345,609, and a
(Continued)

(51) Int. Cl.
*A61F 5/02* (2006.01)
*A61F 5/03* (2006.01)
(Continued)

(52) U.S. Cl.
CPC ............... *A61F 5/028* (2013.01); *A61B 5/01* (2013.01); *A61B 5/112* (2013.01); *A61B 5/1112* (2013.01);
(Continued)

(58) Field of Classification Search
CPC .......... A61F 5/028; A61F 5/024; A61F 5/026; A61F 5/03; A61F 13/14; A61F 5/05816; A61F 5/012; A61F 5/34; A61B 5/01
See application file for complete search history.

(56) References Cited

U.S. PATENT DOCUMENTS

| | | | |
|---|---|---|---|
| 4,135,503 A | 1/1979 | Romano | |
| 4,552,135 A | 11/1985 | Racz et al. | |

(Continued)

FOREIGN PATENT DOCUMENTS

| | | |
|---|---|---|
| WO | WO 2008/150746 A1 | 12/2008 |
| WO | WO 2010/027689 A1 | 3/2010 |
| WO | WO 2014/100092 A1 | 6/2014 |

OTHER PUBLICATIONS

PCT International Search Report; Application No. PCT/US2017/033507; dated Sep. 12, 2017; pp. 1-4.
(Continued)

*Primary Examiner* — Ophelia A Hawthorne

(57) ABSTRACT

An active wearable system includes a one or more positioning elements configured as a torso support and/or other wearable item, one or more sensors for sensing motion, posture, or gait of a subject, and at least one of force applying elements for applying force to selected regions of a body of a subject, and feedback device and other actuators, under the control of control circuitry responsive to sensed motion, posture or gait of the subject. In an aspect, force is applied according to spatial or temporal patterns. Related devices and methods are described.

17 Claims, 25 Drawing Sheets

Related U.S. Application Data continuation-in-part of application No. 13/910,511, filed on Jun. 5, 2013, now abandoned, and a continuation-in-part of application No. 13/875,538, filed on May 2, 2013, now abandoned, and a continuation-in-part of application No. 13/748,871, filed on Jan. 24, 2013, now abandoned, which is a continuation-in-part of application No. 13/721,474, filed on Dec. 20, 2012, and a continuation-in-part of application No. 13/739,868, filed on Jan. 11, 2013, now Pat. No. 9,345,609, application No. 15/161,599, which is a continuation-in-part of application No. 13/721,474, filed on Dec. 20, 2012.

(51) Int. Cl.

| | | |
|---|---|---|
| A61N 1/36 | (2006.01) | |
| A61N 1/08 | (2006.01) | |
| A61B 5/11 | (2006.01) | |
| A61B 5/01 | (2006.01) | |
| A61F 5/34 | (2006.01) | |
| A61F 5/01 | (2006.01) | |

(52) U.S. Cl.
CPC .......... *A61B 5/1116* (2013.01); *A61B 5/1118* (2013.01); *A61F 5/024* (2013.01); *A61F 5/03* (2013.01); *A61F 5/34* (2013.01); *A61N 1/08* (2013.01); *A61N 1/36003* (2013.01); *A61N 1/36014* (2013.01); *A61F 2005/0188* (2013.01); *A61F 2005/0197* (2013.01)

(56) References Cited

U.S. PATENT DOCUMENTS

| | | |
|---|---|---|
| 4,605,582 A | 8/1986 | Sias et al. |
| 5,226,874 A | 7/1993 | Heinz et al. |
| 5,346,461 A | 9/1994 | Heinz et al. |
| 5,437,617 A | 8/1995 | Heinz et al. |
| 5,624,383 A | 4/1997 | Hazard et al. |
| 5,628,721 A | 5/1997 | Arnold et al. |
| 5,749,838 A | 5/1998 | Kline |
| RE35,940 E | 10/1998 | Heinz et al. |
| 5,827,209 A | 10/1998 | Gross |
| 6,007,459 A | 12/1999 | Burgess |
| 6,050,962 A | 4/2000 | Kramer et al. |
| 6,137,675 A | 10/2000 | Perkins |
| 6,331,170 B1 | 12/2001 | Ordway |
| 6,540,707 B1 | 4/2003 | Stark et al. |
| 6,746,413 B2 | 6/2004 | Reinecke et al. |
| 6,776,767 B2 | 8/2004 | Reinecke et al. |
| 6,974,432 B2 | 12/2005 | Reinecke et al. |
| 6,997,892 B2 | 2/2006 | Reinecke |
| 7,063,677 B1 | 6/2006 | Daggett |
| 7,070,571 B2 | 7/2006 | Kramer et al. |
| 7,074,201 B2 | 7/2006 | Reinecke et al. |
| 7,330,566 B2 | 2/2008 | Cutler |
| 7,413,554 B2 | 8/2008 | Kobayashi et al. |
| 7,416,537 B1* | 8/2008 | Stark ............... A61F 5/0125 602/16 |
| 7,553,266 B2 | 6/2009 | Abdoli-Eramaki |
| 7,616,779 B2 | 11/2009 | Liao et al. |
| 7,628,766 B1 | 12/2009 | Kazerooni et al. |
| 7,654,972 B2 | 2/2010 | Alleyne |
| 7,728,839 B2 | 6/2010 | Yang et al. |
| 7,871,388 B2 | 1/2011 | Brown |
| 8,012,113 B2 | 9/2011 | Lee et al. |
| 8,025,632 B2 | 9/2011 | Einarsson |
| 8,074,559 B2 | 12/2011 | Altobelli et al. |
| 8,147,437 B2 | 4/2012 | Alleyne |
| 8,170,656 B2 | 5/2012 | Tan et al. |
| 8,177,733 B2 | 5/2012 | Ashihara et al. |
| 8,396,283 B2 | 3/2013 | Iihoshi et al. |
| 8,657,772 B2 | 2/2014 | Einarsson |
| 8,845,754 B2 | 9/2014 | Streeter et al. |
| 8,870,970 B2 | 10/2014 | Altobelli et al. |
| 8,882,852 B2 | 11/2014 | Altobelli et al. |
| 8,928,484 B2 | 1/2015 | Chang et al. |
| 2001/0008955 A1 | 7/2001 | Garth |
| 2001/0020143 A1* | 9/2001 | Stark ............... A61F 5/012 602/13 |
| 2003/0135134 A1 | 7/2003 | Chase et al. |
| 2004/0003455 A1 | 1/2004 | Davidson |
| 2004/0077982 A1 | 4/2004 | Reinecke |
| 2005/0043660 A1 | 2/2005 | Stark et al. |
| 2005/0182287 A1 | 8/2005 | Becker |
| 2005/0197607 A1 | 9/2005 | Brown |
| 2006/0149179 A1 | 7/2006 | Alleyne |
| 2006/0161085 A1 | 7/2006 | Wikenheiser et al. |
| 2008/0039764 A1 | 2/2008 | Nordt, III et al. |
| 2009/0030359 A1 | 1/2009 | Wikenheiser et al. |
| 2009/0177131 A1 | 7/2009 | Dar et al. |
| 2009/0287109 A1 | 11/2009 | Ferren et al. |
| 2010/0075817 A1 | 3/2010 | Abdoli-Eramaki |
| 2010/0113995 A1 | 5/2010 | Alleyne |
| 2010/0198067 A1* | 8/2010 | Mahfouz ............... G16H 50/50 600/443 |
| 2010/0198124 A1 | 8/2010 | Bhugra |
| 2010/0256717 A1 | 10/2010 | Brown |
| 2011/0028875 A1 | 2/2011 | Martinez Ferro et al. |
| 2011/0034842 A1 | 2/2011 | Guldalian |
| 2011/0082393 A1 | 4/2011 | Bort |
| 2011/0213283 A1 | 9/2011 | Brown |
| 2011/0230806 A1 | 9/2011 | Lou et al. |
| 2011/0247321 A1 | 10/2011 | Streeter et al. |
| 2011/0301519 A1 | 12/2011 | Lan et al. |
| 2012/0116252 A1 | 5/2012 | Newman et al. |
| 2012/0116276 A1 | 5/2012 | Martinez Ferro et al. |
| 2012/0184887 A1 | 7/2012 | Wynne et al. |
| 2012/0184888 A1 | 7/2012 | Alleyne |
| 2012/0215140 A1 | 8/2012 | Hirata et al. |
| 2012/0245491 A1 | 9/2012 | Amell et al. |
| 2013/0015976 A1 | 1/2013 | Chang et al. |
| 2013/0207889 A1 | 8/2013 | Chang et al. |
| 2013/0312168 A1 | 11/2013 | Raanan |
| 2013/0317400 A1 | 11/2013 | Ferezy |
| 2013/0345612 A1 | 12/2013 | Bannister et al. |
| 2014/0009262 A1 | 1/2014 | Robertson et al. |
| 2014/0142485 A1 | 5/2014 | Berry et al. |

OTHER PUBLICATIONS

European Patent Office, Extended European Search Report, Pursuant to Rule 62 EPC; App. No. 14807063.4; dated Dec. 14, 2016 (received by our Agent on Dec. 9, 2016); pp. 1-8.
U.S. Appl. No. 13/910,511, Hyde et al.
U.S. Appl. No. 13/875,538, Hyde et al.
U.S. Appl. No. 13/748,871, Hyde et al.
U.S. Appl. No. 13/739,868, Hyde et al.
U.S. Appl. No. 13/721,474, Hyde et al.
Derawi et al.; "Improved Cycle Detection for Accelerometer Based Gait Authentication"; 2010 Sixth International Conference on Intelligent Information Hiding and Multimedia Signal Processing; 2010; pp. 312-317; 2010 IEEE.
Itoh, Takaki et al.; "Development of New Instrument for Evaluating Leg Motions Using Acceleration Sensors"; Environmental Health and Preventive Medicine; May 2007; pp. 111-118; vol. 12.
Mannini, Andrea et al.; "Accelerometry-Based Classification of Human Activities Using Markov Modeling"; Computational Intelligence and Neuroscience; accepted Jun. 29, 2011; pp. 1-10; vol. 2011; Hindawi Publishing Corporation.
Middleton, Lee et al.; "A floor sensor system for gait recognition"; School of Electronics and Computer Science, University of Southampton; downloaded on Dec. 21, 2012; 6 pages; United Kingdom.
PCT International Search Report; International App. No. PCT/US2013/075943; dated Apr. 3, 2014; pp. 1-3.
PCT International Search Report; International App. No. PCT/US2013/075953; dated Apr. 3, 2014; pp. 1-3.

(56) References Cited

OTHER PUBLICATIONS

PCT International Search Report; International App. No. PCT/US2013/075960; dated Apr. 3, 2014; pp. 1-4.
PCT International Search Report; International App. No. PCT/US2014/036041; dated Sep. 1, 2014; pp. 1-4.
PCT International Search Report; International App. No. PCT/US2014/040826; dated Sep. 22, 2014; pp. 1-3.
Rong et al.; "A Wearable Acceleration Sensor System for Gait Recognition"; 2007 Second IEEE Conference on Industrial Electronics and Applications; 2007; pp. 2654-2659; 2007 IEEE.
Sabelman et al.; "Accelerometric Activity Identification for Remote Assessment of Quality of Movement"; Proceedings of the $26^{th}$ Annual International Conference of the IEEE EMBS; Sep. 1-5, 2004; pp. 4781-4784; 2004 IEEE.
Sander, T. H.; "Magnetoencephalography with a chip-scale atomic magnetometer"; Biomedical Optics Express; May 1, 2012; pp. 981-990; vol. 3; No. 5; Optical Society of America.
Sekine et al.; "Discrimination of Walking Patterns Using Wavelet-Based Fractal Analysis"; IEEE Transactions on Neural Systems and Rehabilitation Engineering; Sep. 2002; pp. 188-196; vol. 10; No. 3; 2002 IEEE.
Torrealba et al.; "Statistics-based technique for automated detection of gait events from accelerometer signals"; Electronics Letters; Oct. 28, 2010; pp. 1-2; vol. 46; No. 22; The Institution of Engineering and Technology 2010.

\* cited by examiner

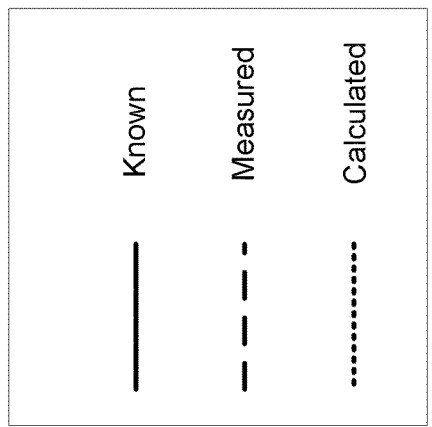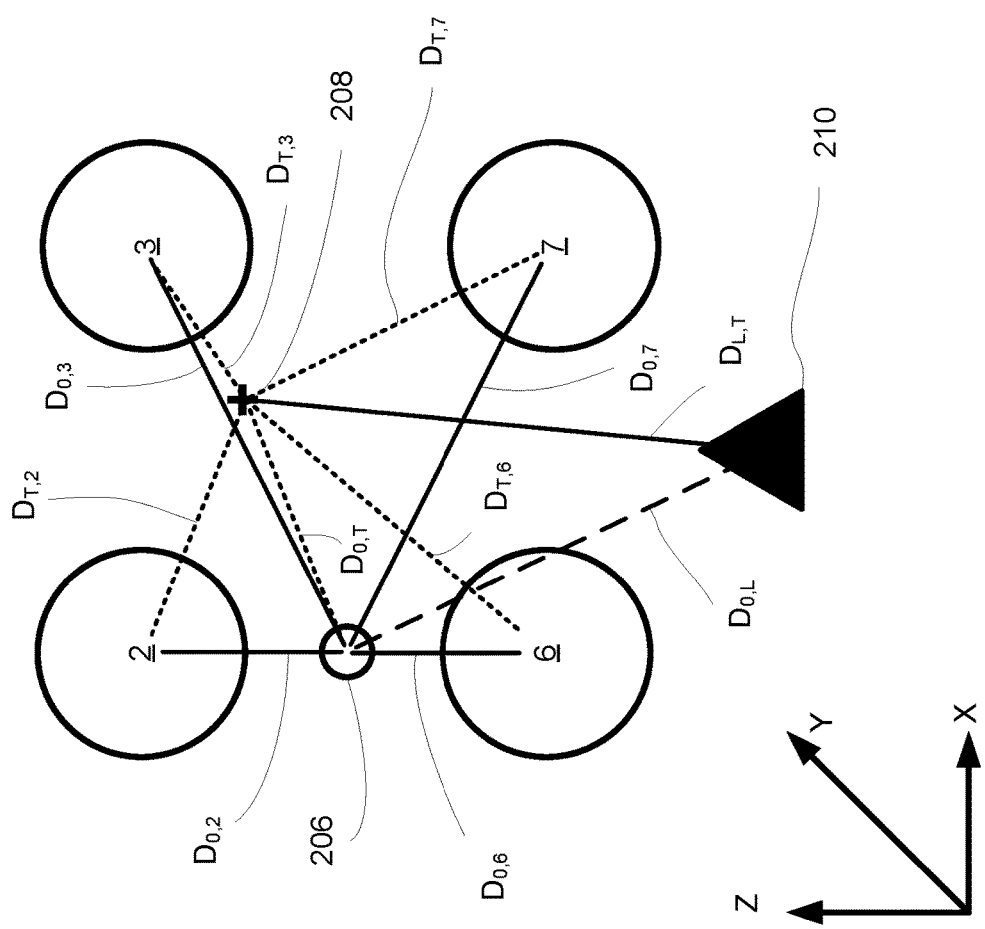
FIG. 3

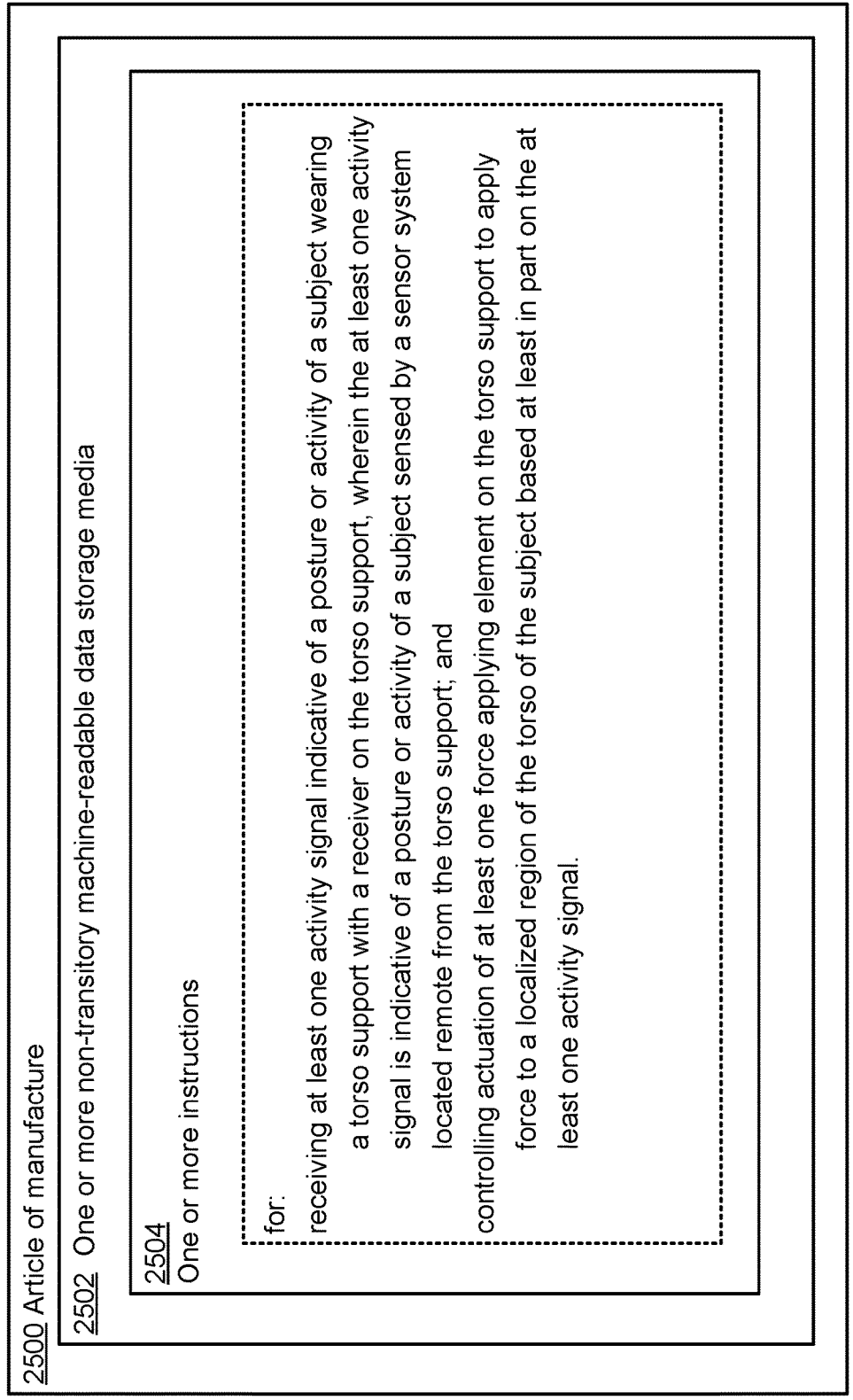

SENSOR-BASED CONTROL OF ACTIVE WEARABLE SYSTEM

If an Application Data Sheet (ADS) has been filed on the filing date of this application, it is incorporated by reference herein. Any applications claimed on the ADS for priority under 35 U.S.C. §§ 119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application claims the benefit of the earliest available effective filing date(s) from the following listed application(s) (the "Priority Applications"), if any, listed below (e.g., claims earliest available priority dates for other than provisional patent applications or claims benefits under 35 USC § 119(e) for provisional patent applications, for any and all parent, grandparent, great-grandparent, etc. applications of the Priority Application(s)).

PRIORITY APPLICATIONS

The present application constitutes a continuation-in-part of U.S. patent application Ser. No. 13/739,868, entitled POSITION SENSING ACTIVE TORSO SUPPORT, naming Roderick A. Hyde, Jordin T. Kare, Dennis J. Rivet, and Lowell L. Wood, Jr. as inventors, filed 11 Jan. 2013, which is currently co-pending or is an application of which a currently co-pending application is entitled to the benefit of the filing date.

The present application constitutes a continuation-in-part of U.S. patent application Ser. No. 13/910,511, entitled TIME-BASED CONTROL OF ACTIVE TORSO SUPPORT, naming Roderick A. Hyde, Jordin T. Kare, Dennis J. Rivet, and Lowell L. Wood, Jr. as inventors, filed 5 Jun. 2013, which is currently co-pending or is an application of which a currently co-pending application is entitled to the benefit of the filing date.

The present application constitutes a continuation-in-part of U.S. patent application Ser. No. 13/875,538, entitled EXTERNAL SENSOR-BASED CONTROL OF ACTIVE TORSO SUPPORT, naming Roderick A. Hyde, Jordin T. Kare, Dennis J. Rivet, and Lowell L. Wood, Jr. as inventors, filed 2 May 2013, which is currently co-pending or is an application of which a currently co-pending application is entitled to the benefit of the filing date.

The present application constitutes a continuation-in-part of U.S. patent application Ser. No. 13/748,871, entitled GAIT-RESPONSIVE ACTIVE TORSO SUPPORT, naming Roderick A. Hyde, Jordin T. Kare, Dennis J. Rivet, and Lowell L. Wood, Jr. as inventors, filed 24 Jan. 2013, which is currently co-pending or is an application of which a currently co-pending application is entitled to the benefit of the filing date, and which is a continuation-in-part of U.S. patent application Ser. No. 13/721,474, entitled POSTURE-DEPENDENT ACTIVE TORSO SUPPORT, naming Roderick A. Hyde, Jordin T. Kare, Dennis J. Rivet, and Lowell L. Wood, Jr. as inventors, filed 20 Dec. 2012, and of U.S. patent application Ser. No. 13/739,868, entitled POSITION SENSING ACTIVE TORSO SUPPORT, naming Roderick A. Hyde, Jordin T. Kare, Dennis J. Rivet, and Lowell L. Wood, Jr. as inventors, filed 11 Jan. 2013.

The present application constitutes a continuation-in-part of U.S. patent application Ser. No. 13/721,474, entitled POSTURE-DEPENDENT ACTIVE TORSO SUPPORT, naming Roderick A. Hyde, Jordin T. Kare, Dennis J. Rivet, and Lowell L. Wood, Jr. as inventors, filed 20 Dec. 2012, which is currently co-pending or is an application of which a currently co-pending application is entitled to the benefit of the filing date.

If the listings of applications provided above are inconsistent with the listings provided via an ADS, it is the intent of the Applicant to claim priority to each application that appears in the Domestic Benefit/National Stage Information section of the ADS and to each application that appears in the Priority Applications section of this application.

All subject matter of the Priority Applications and of any and all applications related to the Priority Applications by priority claims (directly or indirectly), including any priority claims made and subject matter incorporated by reference therein as of the filing date of the instant application, is incorporated herein by reference to the extent such subject matter is not inconsistent herewith.

SUMMARY

In one aspect, a system includes, but is not limited a wearable item including a plurality of actuators, each actuator configured to be positioned with respect to a localized region of a body of a subject; at least one landmark sensor adapted to sense a parameter indicative of a position of a landmark in or on the body of the subject and to produce at least one landmark position signal; at least one positioning element adapted to be worn on the body of the subject and to position the at least one landmark sensor and the plurality of actuators with respect to the body of the subject, wherein each of the plurality of actuators is in a known position relative to the wearable item; at least one activity sensor adapted to detect an input indicative of a posture, gait or activity of the subject, and to generate an activity signal indicative of the posture, gait or activity of the subject; and control circuitry including electrical circuitry for receiving from the at least one landmark sensor the at least one landmark position signal; electrical circuitry for receiving from the at least one activity sensor the at least one activity signal; signal processing circuitry for calculating a position of a target region on the body of the subject relative to the wearable item based on the at least one landmark position signal and on a known position of the target region relative to the landmark; signal processing circuitry for selecting at least one actuator positioned closest to the target region; and electrical circuitry for generating an electrical control signal for controlling actuation of the at least one actuator based at least in part on the at least one activity signal. In addition to the foregoing, other system aspects are described in the claims, drawings, and text forming a part of the disclosure set forth herein.

In one aspect, a system includes, but is not limited at least one remote sensor system including at least one sensor adapted to detect an input indicative of a posture or activity of a subject; and at least one transmitter adapted for transmitting at least one first activity signal indicative of the posture or activity of the subject; an intermediate system including at least one receiver for receiving the at least one first activity signal; and at least one transmitter for transmitting at least one second activity signal, the at least one second activity signal containing at least a portion of the information indicative of the posture or activity of the subject contained in the first activity signal; and a wearable item including at least one actuator; at least one positioning element adapted to position the at least one actuator with respect to the torso of the subject; at least one receiver adapted to receive the at least one second activity signal from the intermediate system; and a control circuitry including electrical circuitry for generating a control signal for controlling actuation of the at least one actuator based at least in part on the at least one second activity signal. In addition to the foregoing, other system aspects are described in the claims, drawings, and text forming a part of the disclosure set forth herein.

In one aspect, a torso support system includes, but is not limited a remote sensor system including a pad, patch, plate or mat adapted to be positioned on a structure; at least one sensor adapted to detect application of pressure to the structure by a subject, the application of pressure indicative of a posture or activity of a subject; and at least one transmitter adapted for transmitting at least one activity signal indicative of the posture or activity of the subject; and a torso support including at least one force applying element adapted to apply force to a localized region of a torso of the subject; at least one positioning element adapted to position the at least one force applying element with respect to the torso of the subject; at least one receiver adapted to receive at least one activity signal indicative of the posture or activity of the subject responsive to the at least one activity signal transmitted by the at least one transmitter and based on at least one signal detected by the at least one sensor in the remote sensor system; and a control circuitry including electrical circuitry for generating a control signal for controlling actuation of the at least one force applying element based at least in part on the at least one activity signal received by the at least one receiver. In addition to the foregoing, other system aspects are described in the claims, drawings, and text forming a part of the disclosure set forth herein.

In one aspect, a torso support includes, but is not limited at least one force applying element adapted to apply force to a localized region of a torso of a subject; at least one positioning element adapted to position the at least one force applying element with respect to the torso of the subject; at least one receiver adapted to receive at least one activity signal indicative of a posture or activity of the subject detected by at least one sensor system located remote from the torso support; at least one memory device adapted to store two or more pre-defined patterns for activation of the at least one force applying element, each pre-defined pattern corresponding to a pre-defined posture or activity of the subject; and control circuitry including electrical circuitry for selecting a pre-defined pattern from the two or more pre-defined patterns based at least in part on the at least one activity signal; and electrical circuitry for generating a control signal for controlling actuation of the at least one force applying element to apply force according to the selected pre-defined pattern. In addition to the foregoing, other system aspects are described in the claims, drawings, and text forming a part of the disclosure set forth herein.

In one aspect, a torso support system includes, but is not limited a remote sensor system including a camera adapted to detect an image indicative of a posture or activity of a subject; and at least one transmitter adapted for transmitting at least one activity signal based on the detected image, the at least one activity signal indicative of the posture or activity of the subject; and a torso support including at least one force applying element adapted to apply force to a localized region of a torso of the subject; at least one positioning element adapted to position the at least one force applying element with respect to the torso of the subject; at least one receiver adapted to receive at least one activity signal indicative of the posture or activity of the subject detected by the at least one sensor system located remote from the torso support; and a control circuitry including electrical circuitry for generating a control signal for controlling actuation of the at least one force applying element based at least in part on the at least one activity signal received by the at least one receiver. In addition to the foregoing, other system aspects are described in the claims, drawings, and text forming a part of the disclosure set forth herein.

In one aspect, a method of controlling a wearable item includes, but is not limited receiving with an electrical circuitry operably coupled to the wearable item and including signal processing circuitry, at least one landmark position signal from at least one sensor, the at least one landmark position signal indicative of a position of a landmark in or on a body of a subject relative to at least a portion of the wearable item worn on the body of the subject, the wearable item including a plurality of actuators, at least one positioning element configured to position each of the plurality of actuators with respect to the body of the subject in a known position relative to the wearable item; and a control circuitry including electrical circuitry for generating an electrical control signal for controlling actuation of the at least one selected actuator to apply force to the target region; determining, with the signal processing circuitry, the position of the target region on the body of the subject relative to the wearable item based on the position of the landmark relative to the wearable item; selecting, with the signal processing circuitry, at least one actuator positioned closest to the target region from among a plurality of actuators based upon information indicative of the positions of the plurality of actuators relative to the wearable item; and controlling, with the control circuitry, actuation of the at least one selected actuator by generating the electrical control signal with the electrical circuitry for generating the electrical control signal. In addition to the foregoing, other method aspects are described in the claims, drawings, and text forming a part of the disclosure set forth herein.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

For a more complete understanding of embodiments, reference now is made to the following descriptions taken in connection with the accompanying drawings. The use of the same symbols in different drawings typically indicates similar or identical items, unless context dictates otherwise. The illustrative embodiments described in the detailed description, drawings, and claims are not meant to be limiting. Other embodiments may be utilized, and other changes may be made, without departing from the spirit or scope of the subject matter presented here.

FIG. 3 is an illustration of aspects of selection of force applying elements for applying a force to a target region.

FIG. 25 illustrates an article of manufacture including non-transitory machine-readable data storage media bearing one or more instructions.

DETAILED DESCRIPTION

Figure 1:
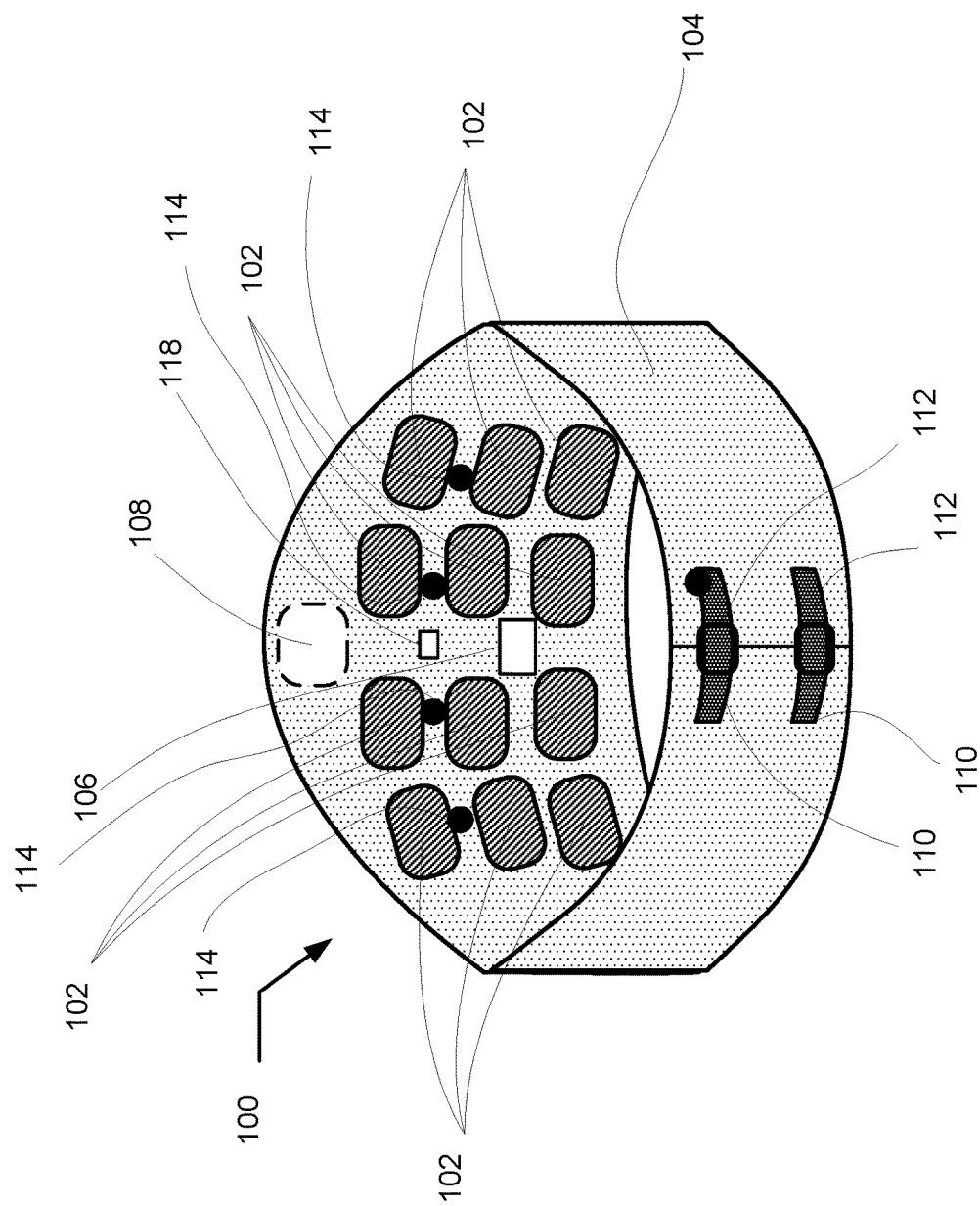
FIG. 1 is an illustration of a torso support.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

FIG. 1 depicts a torso support 100, which includes a plurality of force applying elements 102, a positioning element 104, and control circuitry 106. Each force applying element 102 is adapted to apply force to a localized region of a torso of a subject. A force applying element (e.g., force applying element 102 depicted in FIG. 1) can be any structure that is capable of applying force to a region of the torso of the subject. A controllable active force applying element can be controlled by control circuitry 106.

In the embodiment depicted in FIG. 1, force applying elements 102 are expandable fluid/air filled bladders of the type described, for example, in U.S. Pat. No. 4,135,503 to Romano; U.S. Pat. No. 6,540,707 to Stark et al., and U.S. Pat. No. 5,827,209 to Gross et al., each of which is incorporated herein by reference. Expansion of such bladders is controlled through the use of a motorized pump 108 and electrically controlled valves, with feedback provided by pressure sensors (not shown). Force applying elements 102 are fed by fluid lines running from pump 108, which are not depicted in FIG. 1.

Various types of force applying elements can be used in the embodiments described herein. A force applying element can include a torso-contacting portion such as a pad or probe, and a controllable active force applying element that acts to move the torso contacting portion relative to the torso (e.g., by pressing against the torso and/or by applying shear forces to the torso, e.g., by engaging the surface of the torso by friction). For example, in the embodiment shown in FIG. 1, force applying element 102 includes a fabric pad overlying the bladder that serves to distribute the force as well as enhance comfort for the subject. A force applying element may include one or more of an actuator, mechanical linkage, expandable element, inflatable element, pneumatic element, or hydraulic element, or other structures or components capable of applying force or pressure in a controlled fashion to a localized area of the torso. In an aspect, the force applying element includes a passive force applying element and a controllable active force applying element. In an aspect, a force applying element has a controllable stiffness, a controllable dimension, and/or a controllable position relative to the positioning element. The force applying element can include one or more of a spring, an electroactive polymer, an elastic material, or a viscoelastic material. In an aspect, the force applying element includes an actuator, which may include, for example, a mechanical linkage, an expandable element, an inflatable element, a screw, a spring, a magnetic actuator, an electroactive polymer, a pneumatic element, or a hydraulic element. Mechanically or pneumatically driven force applying elements can be, e.g., as described in U.S. Pat. No. 5,624,383 to Hazard et al., which is incorporated herein by reference. Pneumatic and hydraulic piston type force applying elements as described in U.S. Pat. No. 6,746,413 to Reinecke et al., which is incorporated herein by reference, and screw thread/worm gear assembly structures as described in U.S. Published Patent Application 2009/0030359 to Wikenheiser et al., which is incorporated herein by reference, may be positioned to press against the torso (delivering force substantially perpendicular to the skin surface), or positioned to apply shear forces (i.e., force having a significant component parallel to the skin surface). Electromechanical force applying elements having mechanical components driven by electrical control signals, may receive control signals from control circuitry via a wired electrical connection, or via a wireless signal such as an optical or electromagnetic signal transmitted from the control circuitry associated with the force applying element. A force applying element can include a plate (which may be curved or planar), a probe, a post, or any structure having shape and size suitable for applying force to a desired portion of the torso. Force applying elements as used in torso support may be adapted to fit against a region of the torso of the subject, the region of the torso selected from a back, a side, an abdomen, a chest, a ribcage, a stomach, a hip, a pelvic region, a thorax, a shoulder, a buttock, a lower back, and an upper back. In an aspect, at least a portion of the plurality of force applying elements are adapted to apply force to the torso of the subject, such that at least a component of the force is in a direction normal to the surface of the torso of the subject. A force normal to the surface of the torso may be a compressive force or a tensile force. In an aspect, at least a portion of the plurality of force applying elements are adapted to apply force to the torso of the subject, wherein at least a component of the force applied to the torso of the subject is in a direction tangential to the surface of the torso of the subject. A force applying element can also include a skin-engaging element adapted to apply tensile or shear force to the skin surface; for example a skin-engaging element may include an adhesive, a suction cup, a skin penetrating member, a frictional surface, or other components known to those skilled in the art to provide for the application of tensile or shear forces to the skin.

Positioning element 104 is adapted to position the plurality of force applying elements 102 with respect to the torso of the subject, with each force applying element in a known position relative to the torso support. Force applying elements 102, control circuitry 106, pump 108, and other system components described herein are attached to positioning element 104, but in some aspects may be held in place by pressure or friction, e.g., by being pressed between the torso of the subject and the positioning element. Active torso support 100 is configured as a back support or back brace in the example shown in FIG. 1, with positioning element 104 configured as a belt adapted to be fitted around the waist/lower torso of a subject. However, an active torso support may be configured to support or brace other portions of the torso, including, for example, one or more portions of a side, an abdomen, a chest, a ribcage, a stomach, a hip, a pelvic region, a thorax, a shoulder, a buttock, a lower back, and an upper back. In general, a positioning element 104 can be any structure capable of holding force applying element in position with regard to at least a portion of the torso of the subject, and in various embodiments may include, for example, at least one band, strap, belt, or harness, or a garment such as a corset, girdle, jacket, vest, or brief. In various embodiments, the positioning element may include one or multiple straps or other components, without limitation. The positioning element can be constructed from flexible, resilient, or elastic material, including but not limited to leather, fabric, webbing, mesh, cable, cord, flexible metals or polymers, or sections of rigid metals, polymers or other materials connected in such a manner that the sections can be movably fitted around the torso of the subject, e.g., by a hinge or other linkage or by one or more sections of flexible material.

In other aspects, positioning elements can be configured to fit onto portions of the body other than, or in addition to, than the torso (e.g., arms, legs, hands, feet, head, wrists, ankles, neck, etc.), and may function to secure force applying elements, sensors, and/or other system components thereto. In some aspects, a system may include multiple positioning elements. In some aspects, a single positioning element (e.g., a jacket or other garment) may fit over the torso as well as other portions of the body (e.g., arms). It will be appreciated that the positioning element may perform functions other than positioning force applying elements, sensors, etc. with respect to the body of the subject. For example, a garment may provide any or all of warmth, modesty, and fashion; a wristband may support a watch as well as position a sensor; etc. In general, a positioning element that can be worn on the body of a subject can be considered a wearable item.

As shown in FIG. 1, positioning element 104 includes fasteners to secure the positioning element with respect to the torso of the subject, e.g., straps 110 and buckles 112 as depicted in FIG. 1. In other embodiments, other types of fasteners as are well known in the art can be used, including but not limited to buckles, snaps, zippers, latches, clips, ties, hook and loop fasteners, lacings, and so forth. A positioning element may include an active or passive tensioning component (for example, elastic) to provide for tightening of the positioning element about the torso of the subject to provide for a secure fit. In an embodiment, a positioning element may simply include an elastic component which allows it to be slid onto the torso of the subject, without the need for fasteners.

In an aspect, an active tensioning component included in a positioning element can be used to generate compressive force on a portion of the torso or other body portion. For example, an active tensioning component could be used to tighten a portion of a garment or other wearable item on a portion of the body. It will be appreciated that such tightening by an active tensioning component may produce shear as well as compressive forces. In an aspect, distinct positioning elements (or distinct portions of a single positioning element) are positioned on either side of a joint. An active tensioning component positioned across the joint and connected to the distinct positioning elements (or distinct portions of a single positioning element), can be used to simulate or supplement muscle contraction, to produce or enhance movement of the joint or, conversely, to resist joint movement.

It is contemplated that a torso support as described herein functions generally as follows: activation of one or more force applying elements 102 to apply force to a target region of the torso is accomplished by sensing the position of a landmark in or on the torso with respect to the torso support, determining the position of the target region (a muscle or bony structure, for example, to which force is to be applied) relative to the torso support based on at least one signal indicative of a position of a landmark in or on the torso and a known relationship between the landmark and target region, selecting at least one force applying element positioned closest to the target region, and controlling actuation of the at least one selected force applying element to apply force to the target region. In the embodiment of FIG. 1, a plurality of pulse-echo A-mode ultrasound modules 114 (indicated by black circles in FIG. 1) can be used to detect the position of a landmark (e.g., a specific bony structure) on the pelvis, as described in U.S. Patent Publication No. 2010/0198067 to Mahfouze et el., which is incorporated herein by reference.

By selecting the force applying element based upon the sensed position of the landmark, the location at which the force is applied to the torso can be adjusted to compensate for changes in the position of the torso support with respect to the torso of the subject due to different postures or due to movement of the torso support relative to the torso due to, e.g., loosening or slippage of the torso support. If a particular posture and/or motion of a subject is known to produce motion or loading of muscles and/or bony structures in the subject's torso that is likely to result in injury or discomfort, the active torso support can respond to detection of that posture, or motion by applying force to one or more appropriate portions of the torso to provide support expected to prevent or minimize injury or discomfort. For example, in the embodiment of FIG. 1, inclinometer 118 (which can be a MEMS type digital inclinometer (for example, an Analog Devices ADIS 16209)) can be used to detect the inclination of the subject's torso, to distinguish between upright and bending postures. The selected force applying element 102 can be activated, for example, when the subject is in a bending posture to provide additional support to the back.

The approach for selecting the force applying element(s) to be activated is described in greater detail in connection with FIGS. 2 and 3.

Figure 2:
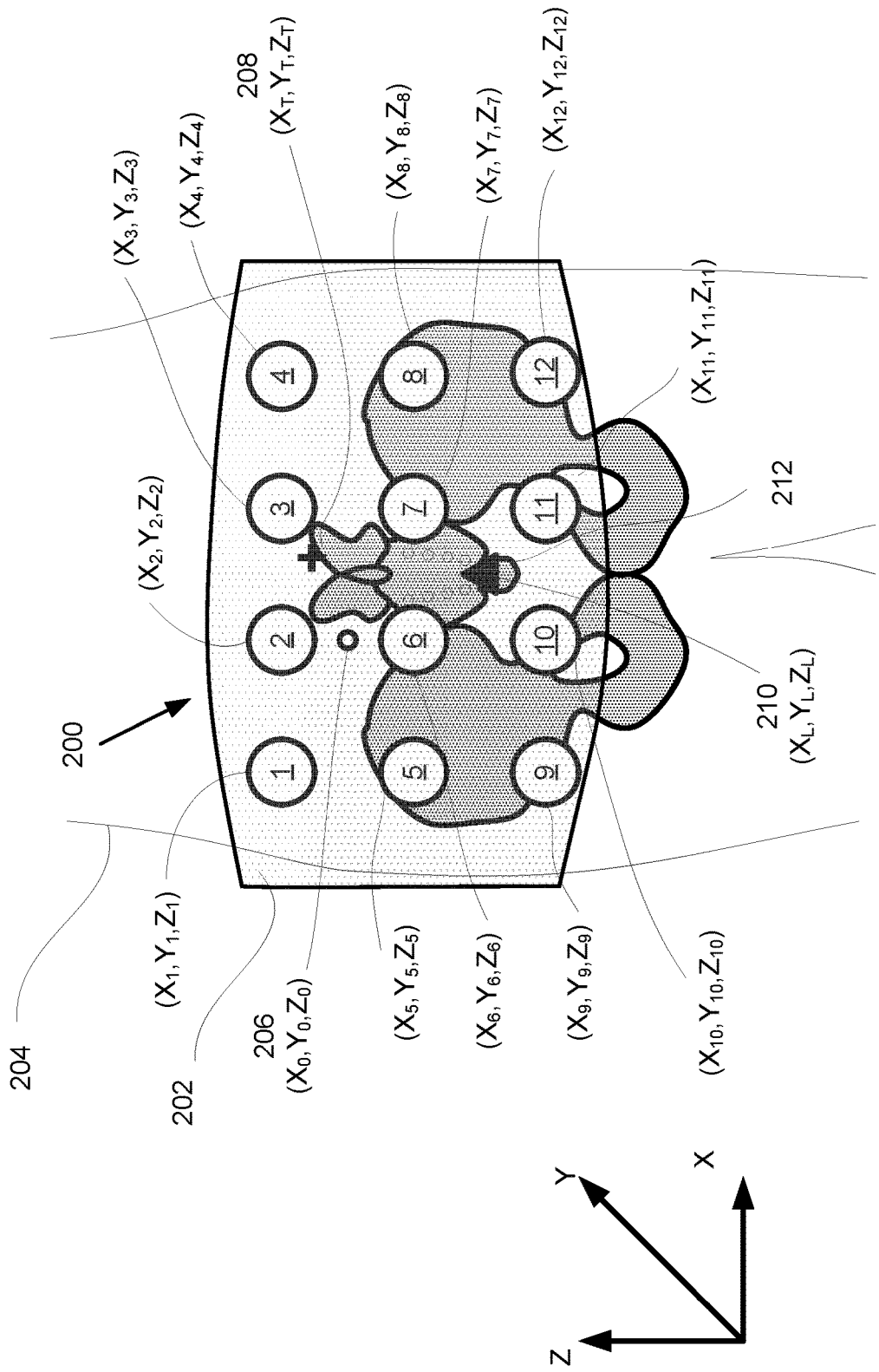
FIG. 2 is an illustration of a torso support.

FIG. 2 depicts a torso support 200, of the type depicted in FIG. 1. Torso support 200 includes multiple force applying elements 1-12 and positioning element 202. Positioning element 202 is configured as a belt worn around the waist/lower torso of subject 204. Positioning element 202 includes a reference location 206, indicated by a white circle in FIG. 2 and having coordinates $X_0$, $Y_0$, $Z_0$. Each of force applying elements 1-12 is attached to positioning element 202 at a known location with respect to reference location 206. Each force applying element i has coordinates $X_1$, $Y_1$, $Z_1$. Also shown are target region 208 (indicated by a cross), having coordinates $X_T$, $Y_T$, $Z_T$, and landmark 210 (indicated by a black triangle), having coordinates $X_L$, $Y_L$, $Z_L$. Target region 208 is a region of the torso of subject 204 at which it is desired to apply force, e.g., to provide support during motion or loading of some or all of the torso. Target region 208 may correspond to a muscle or bony structure, for example. Landmark 210 can be any landmark in or on the torso of the subject that can be sensed by sensors configured to provide a sense signal to the control circuitry of torso support 200. Sensors and control circuitry are not depicted in FIG. 2, but are depicted and described elsewhere herein, for example in connection with FIGS. 1 and 4. In the example shown in FIG. 2, landmark 210 is a region of coccyx 212 of subject 204, which can be distinguished and localized using ultrasound sensors, as discussed in connection with FIG. 1.

FIG. 3 illustrates aspects of the selection of force applying elements for applying force to a target region 208 using torso support 202 as depicted in FIG. 2. FIG. 3 depicts reference location 206, target region 208, and landmark 210 as shown in FIG. 2. For the sake of clarity, only a few of the force applying elements (2, 3, 6 and 7) are shown in FIG. 3. The positions of the various elements of the system shown in FIG. 3 are expressed in Cartesian coordinates, but other coordinate systems may be used. In order to determine which force applying element or elements should be activated to provide force to target region 208, first a signal that contains information regarding the position of the landmark 210 with respect to reference location 206 of the torso support is detected. Various types of signals may be sensed to determine the position of the landmark 210. The position of landmark 210 relative to reference location 206 is indicated by $D_{0,L}$ which may include both scalar and vector components to indicate both distance and direction relative to reference location 206. Next, the position of target region 208 relative to the reference location 206 of the torso support (indicated by $D_{0,T}$) is determined, based on the at least one landmark position signal and on a known position of the target region relative to the landmark (indicated by $D_{L,T}$). In FIG. 3, known positional relationships are indicated by solid lines, measured relationships are indicated by dashed lines, and relationships calculated from other known and/or measured relationships are indicated by dotted lines. As indicated in FIG. 3, $D_{L,T}$ is known, $D_{0,L}$ is measured, and $D_{0,T}$ is determined (calculated) therefrom. At least one force applying element positioned closest to the target region is selected based on the position of each force applying element relative to target region 208. As noted previously, the position of each force applying element is known with respect to the reference position 206 on the positioning element 202, as shown in FIG. 2. For example, force applying elements 2, 3, 6, and 7 shown in FIG. 3 have known positions ($D_{0,2}$ $D_{0,3}$, $D_{0,6}$, and $D_{0,7}$, respectively) relative to reference location 206. Similarly, other force applying elements 1, 4, 5, and 8-12 shown in FIG. 2 have known positions relative to reference position 206, and the position of each of these force applying elements can thus be determined with respect to target region 208. In an aspect, the positions of all force applying elements with respect to target region 208 can be determined.

However, for greater efficiency, once a force applying element having a distance to the target region shorter than the known distance between the force applying elements has been identified, it is not necessary to consider any force applying elements that are more than one such distance away. One or more force applying elements positioned closest to target region 208 can then be selected for activation to apply force to the target region 208. For example the force applying element that is closest to the target region may be selected. "Closest" may refer to the shortest spatial distance, or, in some embodiments, the shortest electrical distance (e.g., lowest impedance/resistance path), or other distance measurement as known to those having skill in the art. In the example shown in FIG. 3, force applying element 3 may be selected as being located at the position closest to target region 208. Once one or more force applying elements have been selected, the selected force applying element(s) can be activated to apply force to the back of the subject. It will be appreciated that, while FIG. 3 depicts a target region that is in a different location than the landmark, in some cases the target region may be in the same location as the landmark (and in some cases the target region itself may serve as the landmark). In such cases, the process for identifying the force applying element(s) to be activated will be simplified in that once the position of the landmark has been determined, no further steps are necessary to determine the position of the target region.

Figure 4:
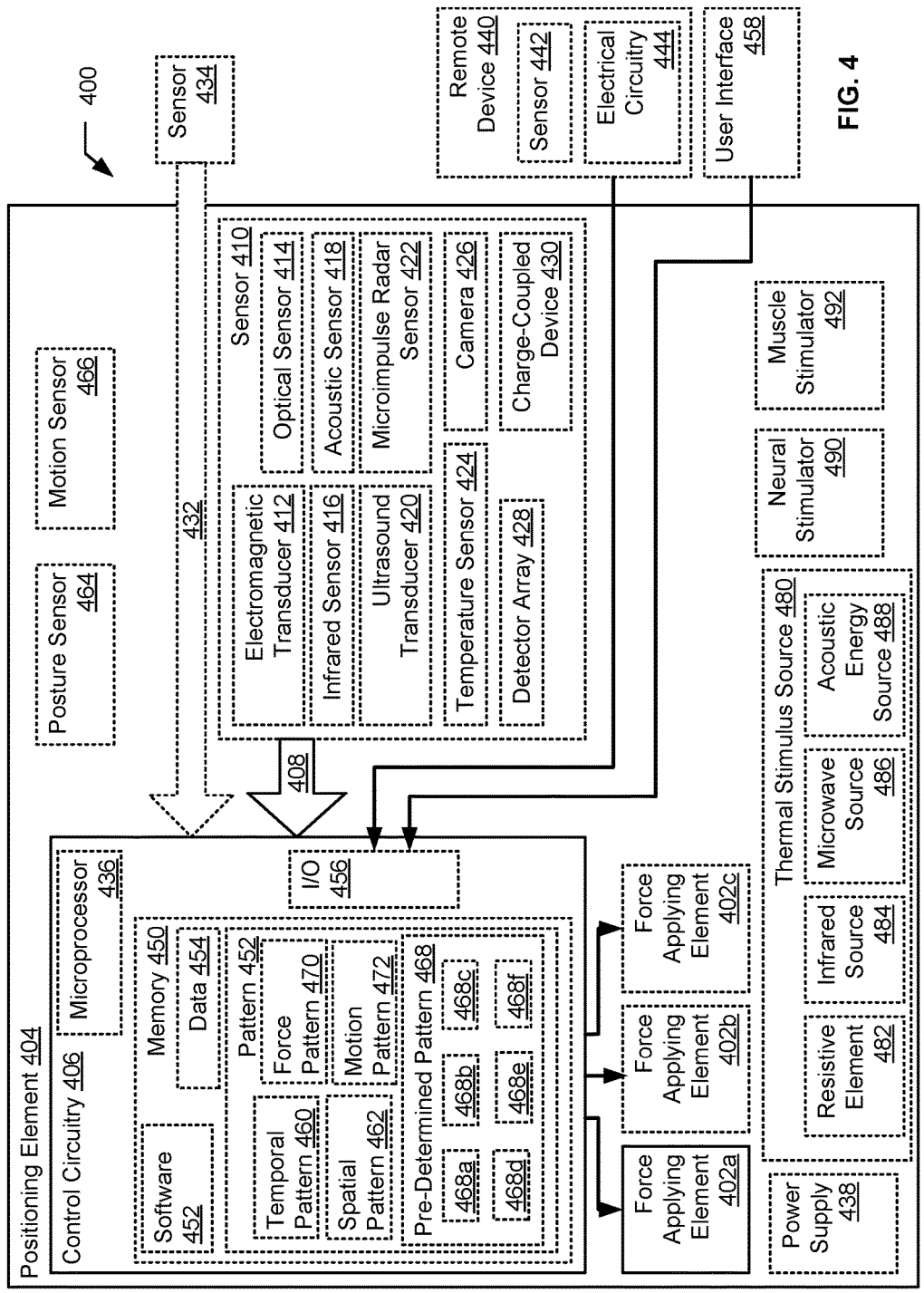
FIG. 4 is a block diagram of a torso support.

FIG. 4 is a block diagram depicting components of a generalized torso support 400, which includes a plurality of force applying elements 402a, 402b, and 402c, a positioning element 404, and control circuitry 406. Force applying elements and positioning elements are as described herein above.

Control circuitry 406 is adapted to receive at least one landmark position signal 408 indicative of a position of a landmark in or on the body of the subject relative to the torso support, determine the position of a target region on the torso of the subject relative to the torso support based on the at least one landmark position signal and on a known position of the target region relative to the landmark, select at least one force applying element (e.g., 402a) positioned closest to the target region, and control actuation of the at least one selected force applying element to apply force to the target region.

In an aspect, the torso support 400 includes at least one sensor 410 adapted to sense a parameter indicative of the position of the landmark in or on the body of the subject and to produce the at least one landmark position signal. The sensor may include, for example, an electromagnetic transducer 412, an optical sensor 414, an infrared sensor 416, an acoustic sensor 418, an ultrasound transducer 420, a microimpulse radar sensor 422, or a temperature sensor 424. The sensor may be configured to sense muscle activity or neural activity. An electromagnetic sensor (e.g., a surface electrode) may be used for sensing electrical activity produced by a nerve, nerve plexus, or other neural structure, or by a muscle (including cardiac or skeletal muscle) below the skin, as described for example in U.S. Pat. No. 8,170,656 issued May 1, 2012, to Tan et al., which is incorporated herein by reference. Body surface electrical potentials measured with electrodes on the skin surface can be used to determine the location of the heart, e.g., as described in U.S. Pat. No. 7,983,743 issued Jul. 19, 2011 to Rudy et al., which is incorporated herein by reference. Magnetic fields produced by neural activity can be sensed, for example, by a magnetometer, e.g., as described by Sander et al. in "Magnetoencephalography with a chip-scale atomic magnetometer," Biomedical Optics Express, May 2012, Vol. 3, No. 5, p. 982, which is incorporated herein by reference.

In an aspect, infrared sensing is used for imaging blood vessels to map the vasculature in the torso of the subject, using a method as described in U.S. Pat. No. 8,238,622 issued Aug. 7, 2012 to Miura et al. See also U.S. Pat. No. 4,032,889 to Nassimbene issued Jun. 28, 1977, which is incorporated herein by reference. U.S. Pat. No. 8,229,178 issued Jul. 24, 2012 to Zhang et al., which is incorporated herein by reference, describes a method for acquiring a palm vein image with visible and infrared light and extracting features from the image for authentication of individual identity. It will be appreciated that the feature extraction and template matching approach used to authenticate identity could similarly be used to match a detected image with a map to localize a landmark.

The sensor may include a camera 426, a detector array 428 (which may be linear array, or two-dimensional array, for example), or Charge-Coupled Device (CCD) 430. In an aspect, the landmark can be a feature on the skin surface such as a pore, a mole, a wrinkle, a hair shaft or hair follicle, etc. Skin characteristics can be identified in an image obtained with CCD sensor, and compared to a reference image to determine a landmark location, using an approach as described in U.S. Pat. No. 7,697,735 issued Apr. 13, 2010 to Adam et al., which is incorporated herein by reference. Registration and comparison of biometric data with template date can be performed as described, for example, in U.S. Pat. No. 8,264,325 issued Sep. 11, 2012 to Fukuda et al., which is incorporated herein by reference.

Acoustic sensors (particularly ultrasound) can be used to detect bony and/or soft-tissue structures within the torso of the subject, using a system and approach generally as described in U.S. Published Application No. 2010/0198067 to Mahfouze et al., dated Aug. 5, 2010, which is incorporated herein by reference.

In an aspect, micro-impulse radar sensors can be used to detect air or fluid filled regions within the torso, which may serve as landmarks in some embodiments, as described in U.S. Pat. No. 6,233,479 issued May 15, 2001 to Haddad et al., which is incorporated herein by reference. Cardiac and neural activity may be detected with a 10 GHz probe, as discussed in U.S. Pat. No. 4,344,440 issued Aug. 17, 1982 to Aaby et al.

In an aspect, a sensor includes a temperature sensor. Temperature sensors are well known to those having skill in the art, including but not limited to resistance temperature detectors (e.g., thermistors, thin film temperature sensors), thermocouples, and infrared/pyroelectric thermometers, etc. Temperature measurements may provide information about muscle damage, inflammation, blood flow, for example.

In an aspect, torso support 400 receives a landmark position signal 432 from a remote sensor 434 not located on the torso support. The transmission of signals from remote sensors to control circuitry on the torso support can occur over a wireless link, as is well known in the art, for example, as described in U.S. Pat. No. 8,170,656 issued May 1, 2012, to Tan et al., and U.S. Published Application No. 2010/0198067 to Mahfouze et el., dated Aug. 5, 2010, each of which is incorporated herein by reference. For example, as described in Tan et al., remote sensors may be located in wearable items such as armbands, wristwatch, shirt, gloves, or other items of clothing, and may include, for example EMG sensors, location sensors, or gesture sensors. Such wearable items may also include a feedback device for providing haptic feedback (vibration or pressure), e.g., in response to sensed motion. For example in an aspect a signal from a remote video camera can supply information regarding the position of a landmark. Other remote sensors, for example as described in Mahfouze et al., may include, but are not limited to, force sensors (e.g., located in a shoe worn by a subject), inertial sensors such as accelerometers, ultrasound transducers, orientation sensors, angle sensors, etc. Such sensors may be worn or carried on the body of the subject. In some aspects, sensors are located remotely from other system components and connected thereto via a wireless link.

Control circuitry 406 may include analog or digital electrical circuitry. In an aspect, control circuitry 406 may include a microprocessor 436. Torso support 400 may include various other elements, including power supply 438. Torso support 400 may be used in connection with a remote device 440, which may include one or more sensors 442, as well as electrical circuitry 444. Control circuitry 406 may include memory 450, which may store software (program modules) 452 used in the operation of torso support 400, and/or data 454. Control circuitry 406 may include I/O structure 456, which provides for communication with remote device 440, e.g., via a wired or wireless (e.g., electromagnetic or optical) connection, or with a user interface 458. Electrical circuitry 444 in remote device 440 includes any electrical circuitry needed for processing signal from sensors 442 and sending signals to or receiving signals from active torso support 400 via I/O structure 456.

In an aspect, the control circuitry 406 is adapted to control actuation of the at least one selected force applying element according to a temporal pattern 460. In an aspect, the control circuitry is adapted to select at least one additional force applying element (e.g., 402b and/or 402c), and to control actuation of the at least one selected force applying element 402a and the at least one additional force applying element (402b and/or 402c) according to a spatial pattern 462 and temporal pattern 460. For example, a spatial pattern provides for applying force at several spatially separated locations to support several different muscles (or different portions of a larger muscle) that are loaded or stressed during a particular motion. Controlling actuation according to a temporal pattern may be as simple as applying a constant force at a selected location for a specific duration (e.g., a duration corresponding to an expected duration of a particular motion, such as a portion of a gait cycle), or applying a force that gradually ramps up to a maximum value as a function of time. More complex temporal or spatio-temporal patterns (e.g., cyclical patterns) may also be employed.

In an aspect, control of the torso support is based upon sensed motion or posture of the subject. Thus, in an aspect, torso support includes at least one sensor 464 adapted for sensing a posture of the subject, and/or at least one sensor 466 adapted for sensing a motion of the subject. Sensor 464 for sensing posture of the subject may include, for example an integrating accelerometer or an inclinometer.

Posture sensing may be performed, for example, as described in U.S. patent application Ser. No. 13/721,474, entitled Posture Dependent Active Torso Support, naming Roderick A. Hyde, Jordin T. Kare, Dennis J. Rivet, and Lowell L. Wood, Jr. as inventors, filed 20 Dec. 2012, which is incorporated herein by reference. A sensor 466 for sensing motion of the subject may include various types of motion sensors known to those having skill in the art, examples of which include a sensor system as described in U.S. Published Patent Application 2011/0082393, to Bort, dated Apr. 7, 2011, which employs piezoelectric sensors to detect deformation of an orthosis caused by movements of a body region, which is incorporated herein by reference; accelerometers, strain gauges, and pressure gauges as described in U.S. Published Patent Application 2001/0020143 to Stark et al., dated Sep. 6, 2001, which is incorporated herein by reference; and force and pressure sensors for detecting joint motion and stress, as discussed in U.S. Pat. No. 5,827,209 issued Oct. 27, 1998 to Gross, which is incorporated herein by reference.

A signal from sensor 464 or sensor 466 may be processed by control circuitry to determine the posture or motion of the subject. Control circuitry 406 may be configured to cause the application of force to a particular target location (e.g., a weak muscle in the subject's back) upon detection of a motion anticipated to cause loading or strain on the muscle. For example, the torso support could be activated to apply force to the weak muscle upon detection of a motion corresponding to the subject bending to pick up an object from the floor, and to release the support once the subject had straightened up again.

Control circuitry 406 may be adapted to control actuation of the at least one selected force applying element (e.g., 402a) according to a pre-defined pattern 468 selectable from a plurality of pre-defined patterns (e.g., 468a-468f). For example, the torso support 400 may include a user input (e.g., user interface 458 may be a user input), and pre-defined pattern 468 may be selectable from the plurality of pre-defined patterns 468a-468f based upon an input received on the user interface 458. Alternatively, or in addition, the torso support 400 may include at least one sensor 464 or 466, adapted for sensing a motion or posture of the subject, respectively, as described herein above, and pre-defined pattern 468 may be selectable from the plurality of pre-defined patterns 468a-468f based upon a sensed motion or posture of the subject. In an aspect, the plurality of pre-defined patterns 468a-468f includes patterns corresponding to a plurality of pre-defined motions or postures of the subject, which may include, but is not limited to, standing, sitting, lying, walking, getting up, sitting down, lying down, twisting, leaning forward, or rolling while lying down (e.g., changing position from lying on a back to lying on a side, lying on a side to lying on a front, lying on a side to lying on a back, lying on a front to lying on a side, and so forth). Control circuitry 406 may be adapted to control actuation of the at least one selected force applying element 402a by controlling a pattern of force applied by the at least one selected force applying element 402a, or by controlling a pattern of motion generated by the at least one selected force applying element 402a, for example by using force pattern 470 or motion pattern 472.

In an embodiment, torso support includes a thermal stimulus source 480, which may include for example, a resistive element 482, an infrared source 484, a microwave source 486, an acoustic energy source 488, or other elements capable of providing localized heating to the skin or underlying tissues. A thermal stimulus may be applied to stimulate blood circulation, promote healing, enhance comfort of sore or injured muscles, or serve as a counter-stimulus to reduce sensation of pain, for example.

In an embodiment, the torso support includes a neural stimulator 490 or a muscle stimulator 492. A neural stimulator 490 or muscle stimulator 492 may include an electrode for delivering an electrical stimulus, or one or more coils for delivering a magnetic stimulus, for example, either of which can be driven by an appropriately configured electrical control signal, as known to those having skill in the art. (See, for example, U.S. Pat. No. 8,285,381 issued Oct. 9, 2012 to Fahey et al., which is incorporated herein by reference). Other types of neural or muscle stimulators may be used, as known to those having skill in the art. Nerve and/or muscle stimulation can be used to activate muscles to provide a higher level of strength or stability in the back, or to block or counter pain signals, for example.

Figure 5:
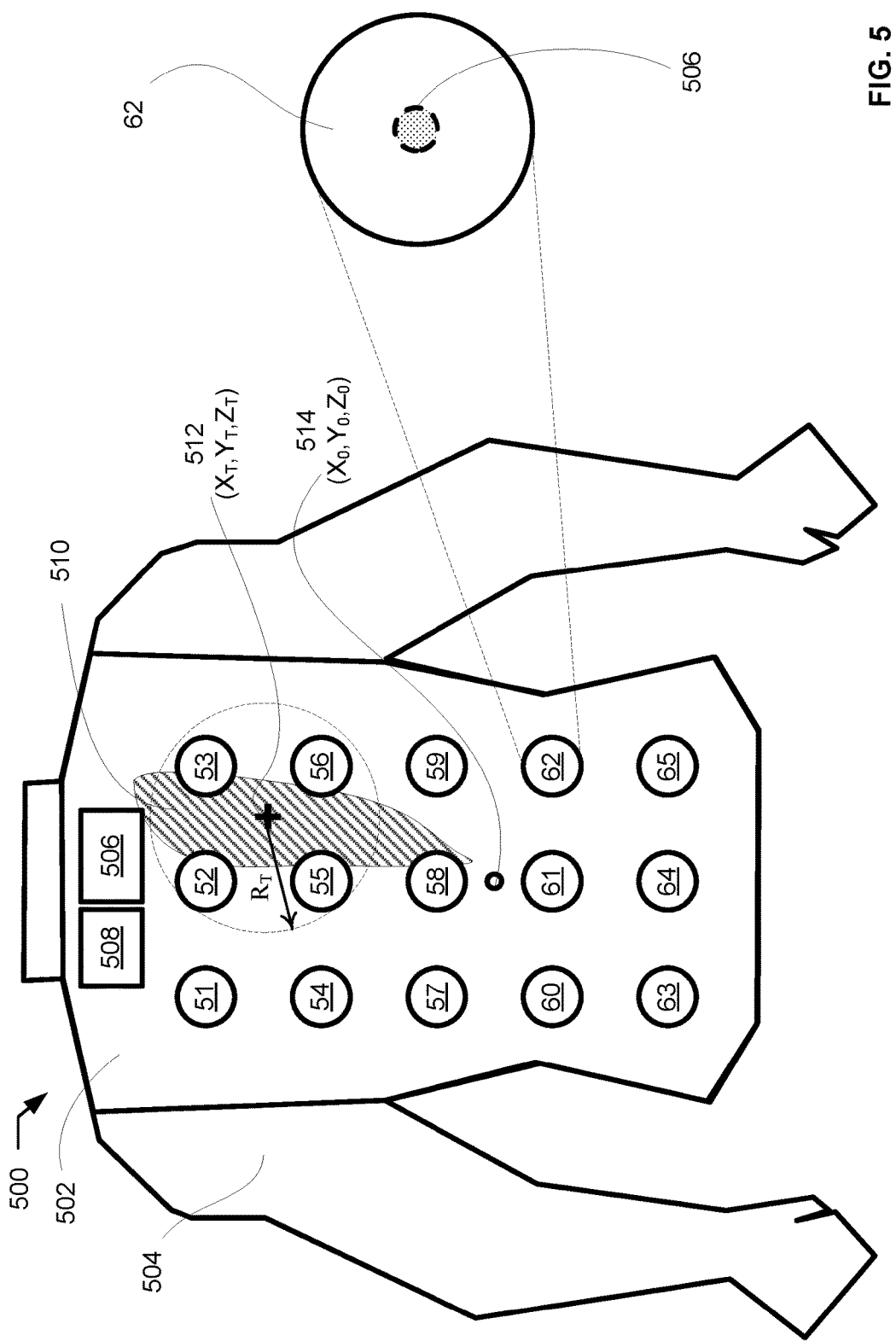
FIG. 5 is an illustration of a torso support.

A further example of a torso support is depicted in FIG. 5. In this example, the sensed landmark, as well as the target region to which force is applied is an active muscle; thus the landmark and the target region are co-located and have the same position relative to the torso support. Torso support 500 includes positioning element 502, which is configured as a vest worn on the torso of subject 504, a plurality of electromechanical force applying elements 51-65, control circuitry 506, and power supply 508, which may be, for example a battery, housed with or adjacent to control circuitry 506. Control circuitry 506 is connected to force applying elements 51-65 by wired connections (not shown). However, as an alternative, control circuitry 506 and force applying elements 51-65 could include transmitters and receivers for wireless communication between components. Each of force applying elements 51-65 has associated therewith an electrical sensor (e.g., an electrode) adapted to contact the skin of the subject to detect electrical activity (electromyogram, or EMG) associated with muscle activity. See, for example, electrode 506 on force applying element 62, illustrated in expanded view. Electrode 506 is located on the side of force applying element 62 that faces toward the torso of subject 504 so that it can contact the skin of subject 504. In use, electrical activity from a muscle (e.g., muscle 510) is sensed from one or more electrodes associated with force applying elements. For example, activity from muscle 510 would produce an EMG signal detectable by electrodes associated with force applying elements 52, 53, 55, 56 and 58. The position of active muscle 510 is determined based on the EMG signal levels on the various electrodes. Thus, a combined landmark/target region 512 having location ($X_T$, $Y_T, Z_T$) relative to reference point 514 on torso support 500, corresponding to a central region of muscle 510, is identified. Accordingly one or more force applying elements are selected to apply force to the target region. For example, force applying elements 52, 53, 55 and 56 may be selected as being within a radius $R_T$ of target region 512. Selected force applying elements 52, 53, 55 and 56 can then be actuated to deliver force to target region 512. In an aspect, force applying elements 52, 53, 55 and 56 can be actuated to deliver force to target region 512 while muscle 510 is actively contracting. In another aspect, force applying elements 52, 53, 55 and 56 can be actuated to deliver force to target region 512 at a specified delay following active contraction of muscle 510.

Figure 6:
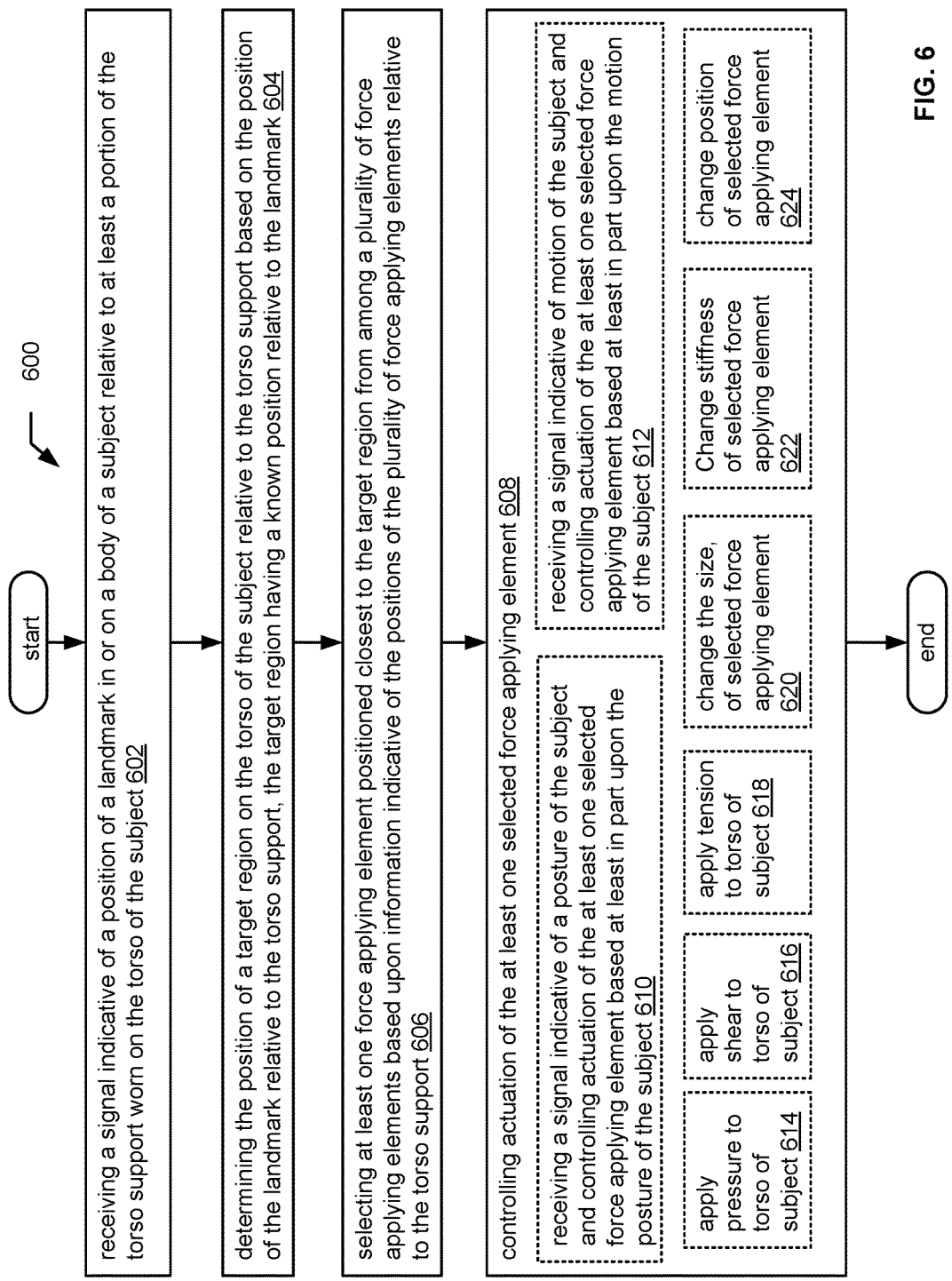
FIG. 6 is a flow diagram of a method of controlling a torso support.

FIG. 6 is a flow diagram of a method 600 of controlling a torso support as described herein. Method 600 includes receiving a signal indicative of a position of a landmark in or on a body of a subject relative to at least a portion of a torso support worn on the torso of the subject, as indicated at 602; determining the position of a target region on the torso of the subject relative to the torso support based on the position of the landmark relative to the torso support, the target region having a known position relative to the landmark, at 604; selecting at least one force applying element positioned closest to the target region from among a plurality of force applying elements based upon information indicative of the positions of the plurality of force applying elements relative to the torso support, at 606; and controlling actuation of the at least one selected force applying element, at 608.

In an aspect, method 600 also includes receiving a signal indicative of a posture of the subject and controlling actuation of the at least one selected force applying element based at least in part upon the posture of the subject, as indicated at 610. In an aspect, the method includes receiving a signal indicative of motion of the subject and controlling actuation of the at least one selected force applying element based at least in part upon the motion of the subject, as indicated at 612.

In an aspect, method 600 includes controlling actuation of the at least one selected force applying element to apply pressure 614, shear 616, or tension 618 to the torso of the subject. The method can include controlling actuation of the at least one selected force applying element to change the size 620, stiffness 622, or position 624 of the at least one selected force applying element.

Figure 7:
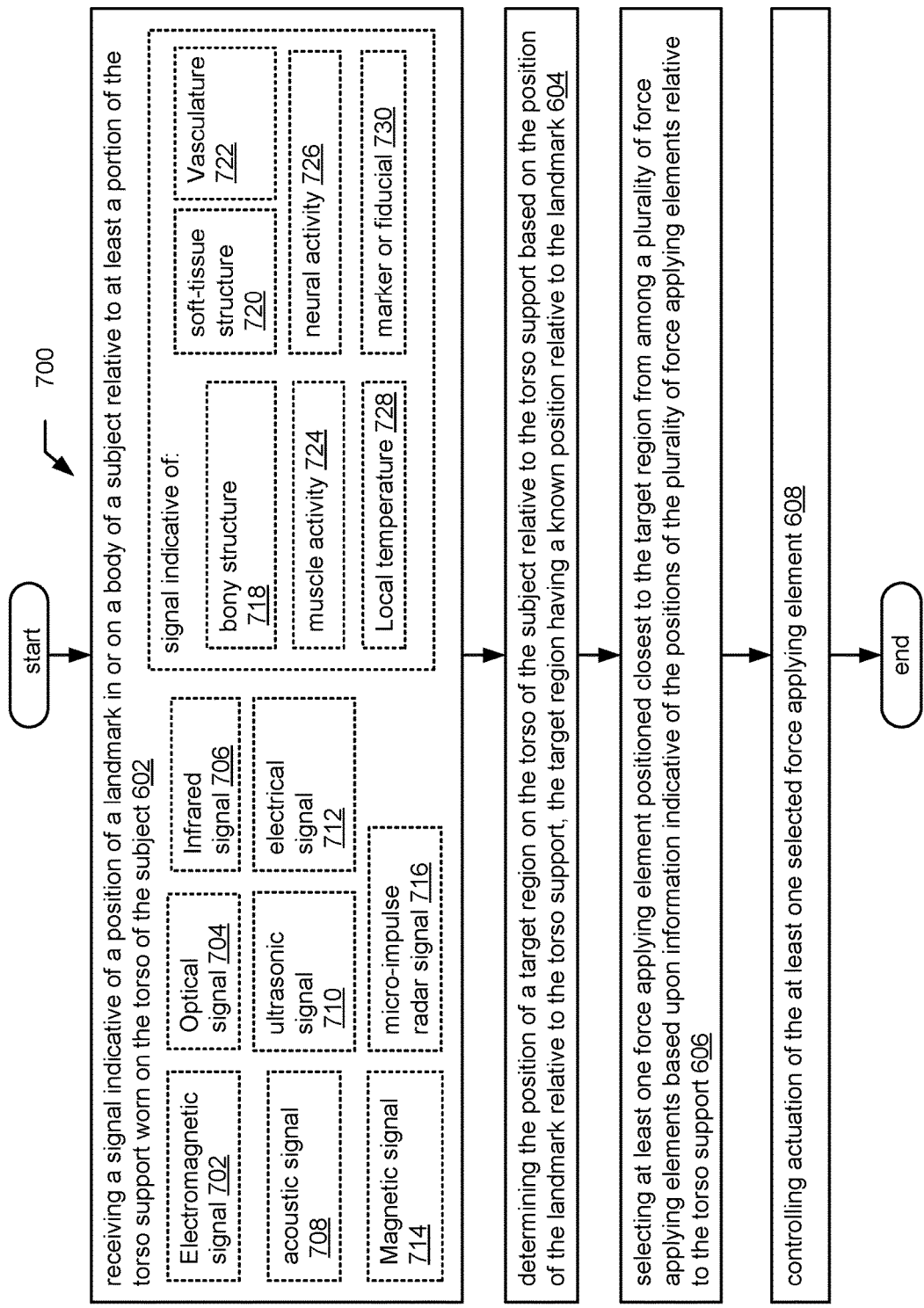
FIG. 7 is a flow diagram of a method of controlling a torso support.

FIG. 7 depicts a method 700, including variations of the method shown in FIG. 6. In various embodiments, receiving a signal indicative of a position of a landmark includes receiving an electromagnetic signal 702, optical signal 704, infrared signal 706, acoustic signal 708, ultrasonic signal 710, electrical signal 712, magnetic signal 714, or micro-impulse radar signal 716. Receiving a signal indicative of the position of a landmark may include receiving a signal indicative of at least one bony structure within the body of the subject 718, a soft-tissue structure within the body of the subject 720, vasculature below a skin surface of the body of the subject 722, muscle activity 724, neural activity 726, or a local temperature 728 on or below the skin surface. Receiving a signal indicative of the position of a landmark may include receiving a signal indicative of a marker or fiducial 730, which may be on the skin surface of the subject, or below the skin surface of the subject.

Figure 8:
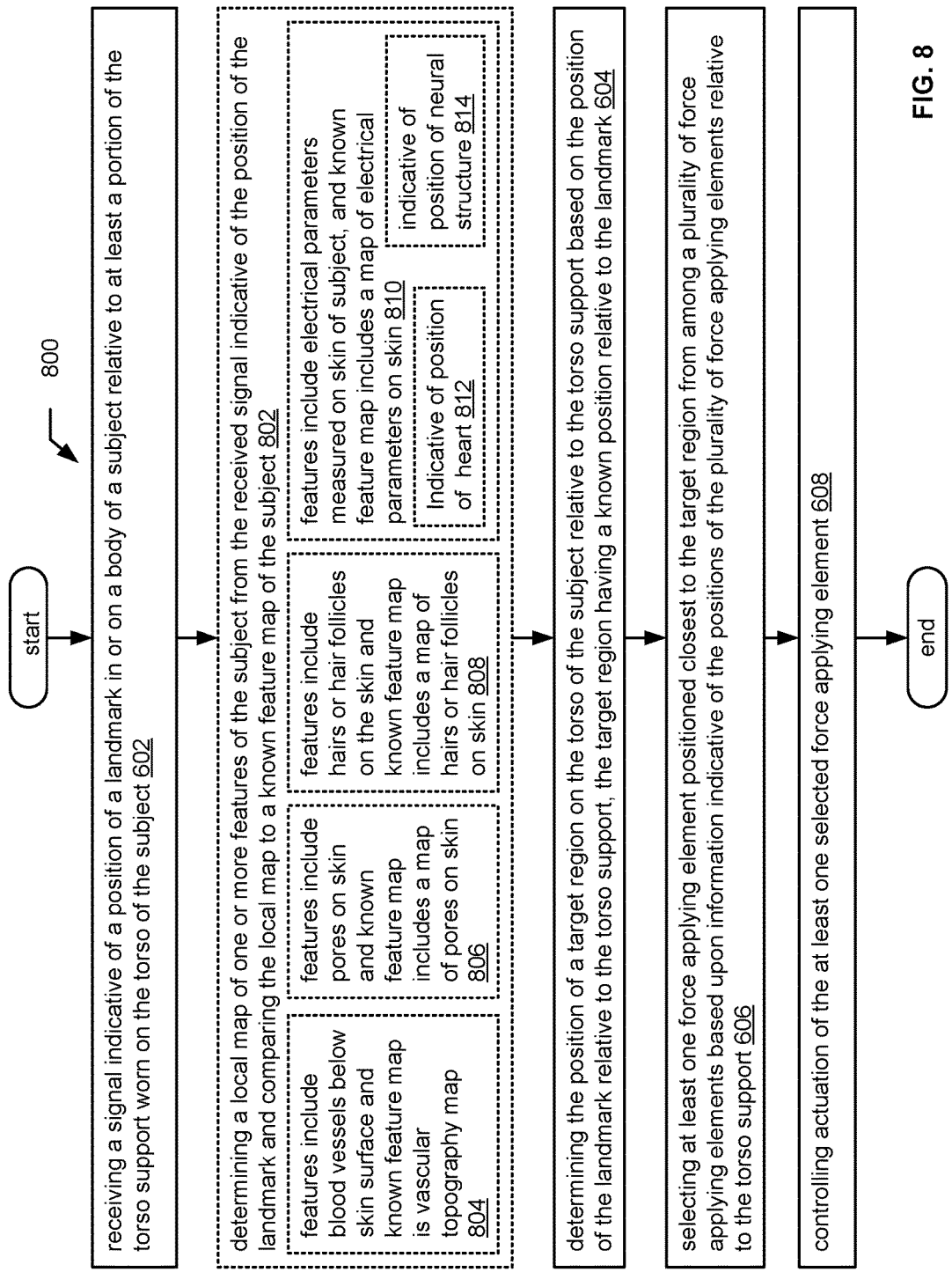
FIG. 8 is a flow diagram of a method of controlling a torso support.

As shown in FIG. 8, in an aspect, a related method 800 includes determining a local map of one or more features of the subject from the received signal indicative of the position of the landmark and comparing the local map to a known feature map of the subject, as indicated at 802. For example, in an aspect the one or more features include blood vessels below a skin surface of the body of the subject, and the known feature map is a vascular topography map of the subject, as indicated at 804. In another aspect, the one or more features include pores on the skin of the subject, and the known feature map includes a map of pores on the skin of the subject, as indicated at 806. In another aspect, the one or more features include hairs or hair follicles on the skin of the subject, and the known feature map includes a map of hairs or hair follicles on the skin of the subject, as indicated at 808. In an aspect, the one or more features include electrical parameters measured on the skin of the subject, and the known feature map includes a map of electrical parameters on the skin of the subject, as indicated at 810. The electrical parameters may be indicative of the position of the heart of the subject, as indicated at 812 or the position of a neural structure of the subject, as indicated at 814, for example.

Figure 9:
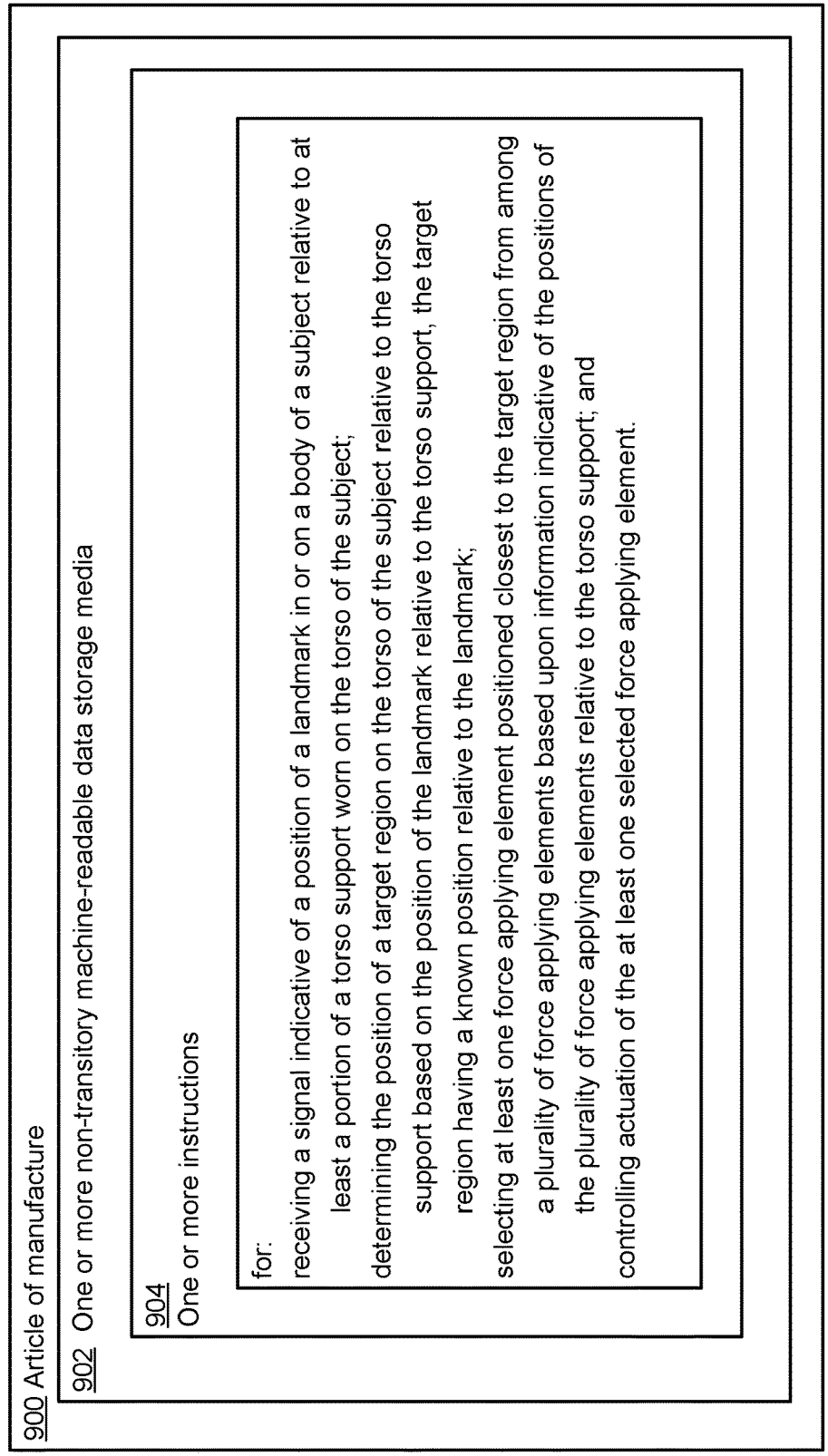
FIG. 9 illustrates an article of manufacture including non-transitory machine-readable data storage media bearing one or more instructions.

FIG. 9 depicts an article of manufacture 900 that includes one or more non-transitory machine-readable data storage media 902 bearing one or more instructions 904 for: receiving a signal indicative of a position of a landmark in or on a body of a subject relative to at least a portion of the torso support worn on the torso of the subject; determining the position of a target region on the torso of the subject relative to the torso support based on the position of the landmark relative to the torso support, the target region having a known position relative to the landmark; selecting at least one force applying element positioned closest to the target region from among a plurality of force applying elements based upon information indicative of the positions of the plurality of force applying elements relative to the torso support; and controlling actuation of the at least one selected force applying element. Instructions 904 depicted in FIG. 9 correspond to the method 600 shown in FIG. 6. Other variants of methods as depicted in FIGS. 6-8 and as described herein can be implemented through the use of non-transitory machine-readable data storage media bearing one or more suitable instructions.

In an aspect, the one or more non-transitory machine-readable data storage media 902 bear one or more instructions 904 for receiving a signal indicative of a posture of the subject and controlling actuation of the at least one selected force applying element based at least in part upon the posture of the subject. In an aspect, the one or more non-transitory machine-readable data storage media 902 bear one or more instructions 904 for receiving a signal indicative of motion of the subject and controlling actuation of the at least one selected force applying element based at least in part upon the motion of the subject.

The one or more non-transitory machine-readable data storage media 902 may bear one or more instructions 904 for determining the position of at least one bony structure within the body of the subject, a soft-tissue structure within the body of the subject, vasculature below a skin surface of the body of the subject, an active muscle, or an active neural structure.

The one or more non-transitory machine-readable data storage media 902 may bear one or more instructions 904 for determining the position of the target region based upon one or more measurements of local temperature on or below the skin surface.

The one or more non-transitory machine-readable data storage media 902 may bear one or more instructions 904 for determining the position of a marker or fiducial on the skin surface of the subject, or below the skin surface of the subject.

The one or more non-transitory machine-readable data storage media 902 may bear one or more instructions 904 for determining a local map of one or more features of the subject from the received signal indicative of the position of the landmark and one or more instructions 904 for comparing the local map to a known feature map of the subject. For example, in various embodiment, the one or more features include blood vessels below a skin surface of the body of the subject and the known feature map is a vascular topography map of the subject; the one or more features include pores on the skin of the subject and the known feature map includes a map of pores on the skin of the subject; the one or more features include hairs or hair follicles on the skin of the subject and the known feature map includes a map of hairs or hair follicles on the skin of the subject; or the one or more features include electrical parameters measured on the skin of the subject, and the known feature map includes a map of electrical parameters on the skin of the subject. Electrical parameters may be indicative of the position of the heart of the subject, or the position of a neural structure (such as a nerve, spinal cord, nerve ganglion, nerve plexus, etc.) of the subject.

In an aspect, the one or more non-transitory machine-readable data storage media 902 bear one or more instructions 904 for controlling actuation of the at least one selected force applying element to apply pressure, shear, or tension to the torso of the subject.

In an aspect, the one or more non-transitory machine-readable data storage media 902 bear one or more instructions 904 for controlling actuation of the at least one selected force applying element, for example, to change the size, stiffness, or position of the at least one selected force applying element.

Figure 10:
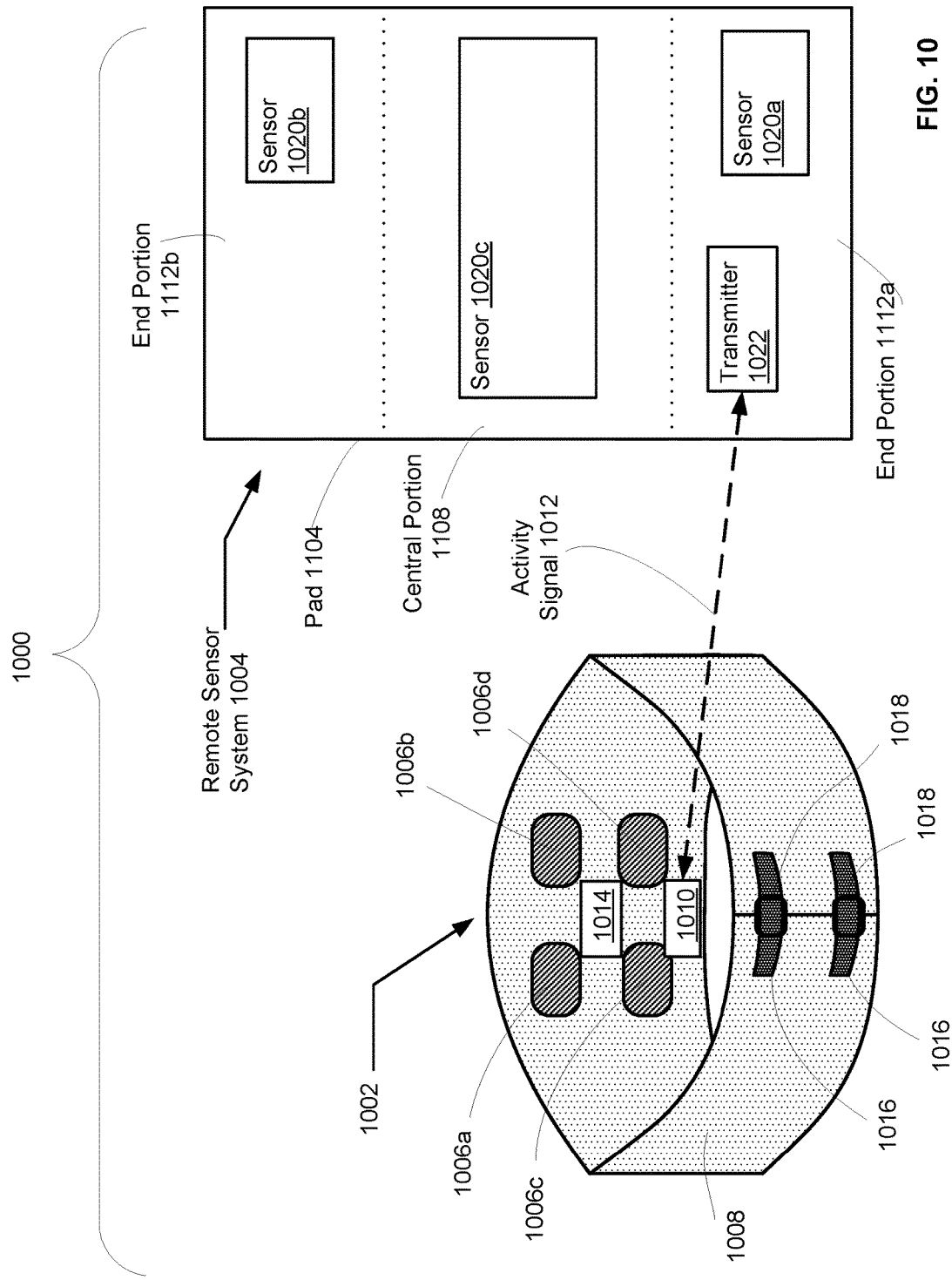
FIG. 10 is an illustration of a torso support system.

FIG. 10 depicts an embodiment of a torso support system 1000 that includes a torso support 1002 that is used in combination with a remote sensor system 1004. Torso support 1002 includes force applying elements 1006a-1006d, which are adapted to apply force to a localized region of a torso of a subject wearing the torso support; at least one positioning element 1008 adapted to position force applying element 1006a-1006d with respect to the torso of the subject; at least one receiver 1010 adapted to receive at least one activity signal 1012 indicative of the posture or activity of the subject detected by the at least one remote sensor system 1004 located remote from the torso support 1002; and control circuitry 1014 configured to control actuation of the at least one force applying element 1006a-1006d based at least in part on at the least one activity signal 1012 received by the at least one receiver 1010. In some embodiments it may be desirable to provide for two-way communication between torso support 1002 and remote sensor system 1004, in which case receiver 1010 may be a transceiver or other two-way communication device, or a component of communication circuitry that includes one or more transmitter in addition to one or more receiver, and such variations are considered to fall within the scope of the present invention.

Remote sensor system 1004 includes at least one sensor (sensors 1020a, 1020b, and 1020c are shown) used to detect an input indicative of a posture or activity of subject; and at least one transmitter 1022 adapted for transmitting activity signal 1012, indicative of the posture or activity of the subject. As will be described in greater detail in connection with FIG. 11, remote sensor system 1004 is configured as a pad 1104 that can be positioned on the seat and armrests of a chair.

Force applying elements 1006a-1006d can be used to apply force or pressure to a region of the torso of the subject, for example, for the purpose of providing support to weak or injured muscles and/or to prevent or minimize discomfort or injury to muscles or other structures in the torso due to loading. Torso support 1002 may be configured as a back support or back brace, as depicted in FIG. 10, but is not limited thereto, and may be configured to support or brace other portions of the torso, including, for example, portions of a back, a side, an abdomen, a chest, a ribcage, a stomach, a hip, a pelvic region, a thoracic region, a shoulder region, a pectoral region, a buttock, a lower back, or an upper back.

It is contemplated that a torso support system as described herein functions generally as follows: if a particular posture or activity of a subject is known to produce motion or loading of muscles and/or bony structures in the subject's torso that is likely to result in injury or discomfort, the active torso support will respond to detection of that posture or activity by the remote sensor system by applying force to one or more appropriate portions of the torso to provide support expected to prevent or minimize injury or discomfort. A person suffering from lower back pain is typically advised to avoid twisting motions, particularly twisting the torso between hips and shoulders, and to reduce the load on back muscles by shifting the load to other muscles, e.g., the arms and legs. Tasks such as lifting, getting in and out of a vehicle or chair, and getting in or out of bed are particularly problematic for a person with back pain. An active torso support as described herein provides additional support to reduce loading, as described herein and illustrated by a number of examples. In situations during which less or no support is needed, force applying elements can be deactivated, or the force applied by the force applying element can be reduced to provide the subject greater freedom of movement, flexibility, or comfort.

In the embodiment depicted in FIG. 10, and in other embodiments described and depicted herein, a force applying element can be any structure that is capable of applying force to a region of the torso of the subject, via a torso-contacting portion such as a pad or probe, and a controllable force-generating component that acts to move the torso contacting portion relative to the torso (e.g., by pressing against the torso and/or by applying shear forces to the torso, e.g., by engaging the surface of the torso by friction). A force applying element can be adapted to fit against a portion of the torso of the subject, where the portion of the torso of the subject is selected from a back, a side, an abdomen, a chest, a ribcage, a stomach, a hip, a pelvic region, a thoracic region, a shoulder region, a pectoral region, a buttock, a lower back, and an upper back. Size, configuration, and force-applying capability of the force applying element are adapted for use with the selected portion of the torso.

Force applying elements (e.g., force applying elements 1006a-1006d) can be controlled by control circuitry (e.g., control circuitry 1014), e.g., via an electrical signal carried via an electrical connection or via a wireless signal such as an optical or electromagnetic signal transmitted from the control circuitry to the force applying element. A force applying element may include one or more actuator, mechanical linkage, expandable element, inflatable element, pneumatic element, hydraulic element, or other structures or components capable of applying force or pressure in a controlled fashion to a localized area of the torso.

A force applying element may be adapted to apply force to the torso of the subject with at least a component of the force in a direction normal to the surface of the torso of the subject. For example, a force applying element can include a plate (which may be curved or planar) a probe, or any structure having shape and size suitable for applying force to a desired portion of the torso. The force applying element may be adapted to apply compressive force to the skin surface.

A force applying element can also include a skin-engaging element adapted to apply tensile or shear force to the skin surface; for example a skin-engaging element may include an adhesive, suction cup, or a frictional surface, or other components known to those skilled in the art to provide for the application of tensile or shear forces to the skin. Thus, a force applying element can be adapted to apply force to the torso of the subject with at least a component of the force in a direction tangential to the surface of the torso of the subject. In an aspect, a force applying element includes a passive force applying element and a controllable active force applying element. In an aspect, a force applying element has a controllable stiffness, a controllable dimension, and/or a controllable position relative to the positioning element. A force applying element can include one or more of a spring, an elastic material, or a viscoelastic material. In an aspect, a force applying element includes an actuator, which may include, for example, a mechanical linkage, an expandable element, an inflatable element, a screw, a pneumatic element, or a hydraulic element. Expandable fluid/air filled bladders, are described, for example, in U.S. Pat. No. 4,135,503 to Romano; U.S. Pat. No. 6,540,707 to Stark et al, and U.S. Pat. No. 5,827,209 to Gross et al., each of which is incorporated herein by reference. Expansion of such bladders can be controlled through the use of a motorized pump and electrically controlled valves, with feedback provided by pressure sensors. Mechanically or pneumatically driven force applying elements can be of the type described in U.S. Pat. No. 5,624,383 to Hazard et al., which is incorporated herein by reference. Pneumatic and hydraulic piston type force applying elements as described in U.S. Pat. No. 6,746,413 to Reinecke et al., which is incorporated herein by reference, and screw thread/worm gear assembly structures as described in U.S. Published Patent Application 2009/0030359 to Wikenheiser et al., which is incorporated herein by reference, may be positioned to press against the torso (delivering force substantially perpendicular to the skin surface), or positioned to apply shear forces (i.e., force having a significant component parallel to the skin surface).

Although positioning element 1008 is depicted in FIG. 10 as a belt adapted to be fitted around the waist/mid-torso of a subject, the positioning element can be any structure capable of holding force applying elements 1006a-1006d in position with regard to at least a portion of the torso of the subject, and may include, for example, include at least one band, strap, belt, or harness, or a garment such as a corset, girdle, jacket, vest, or brief. The positioning element may include one or multiple straps or other components, without limitation. The positioning element can be constructed from flexible, resilient, or elastic material, including but not limited to leather, fabric, webbing, mesh, cable, cord, flexible metals or polymers, or sections of rigid metals, polymers or other materials connected in such a manner that the sections can be movably fitted around the torso of the subject, e.g., by a hinge or other linkage or by one or more sections of flexible material. A positioning element (e.g., positioning element 1008) may include fasteners to secure the positioning element with respect to the torso of the subject, e.g., straps 1016 and buckles 1018 as depicted in FIG. 10, or other fasteners as are known in the art, including but not limited to buckles, snaps, zippers, latches, clips, ties, hook and loop fasteners, lacings, and so forth. A positioning element may include an active or passive tensioning component (for example, elastic) to provide for tightening of the positioning element about the torso of the subject to provide for a secure fit. In an embodiment, positioning element may simply include an elastic component which allows it to be slid onto the torso of the subject, without the need for fasteners.

Force applying elements 1006a-1006d, receiver 1010, control circuitry 1014, and other system components described herein may be attached to the positioning element 1008 or held in place by pressure or friction, e.g., by being pressed between the torso of the subject and the positioning element.

Figure 11:
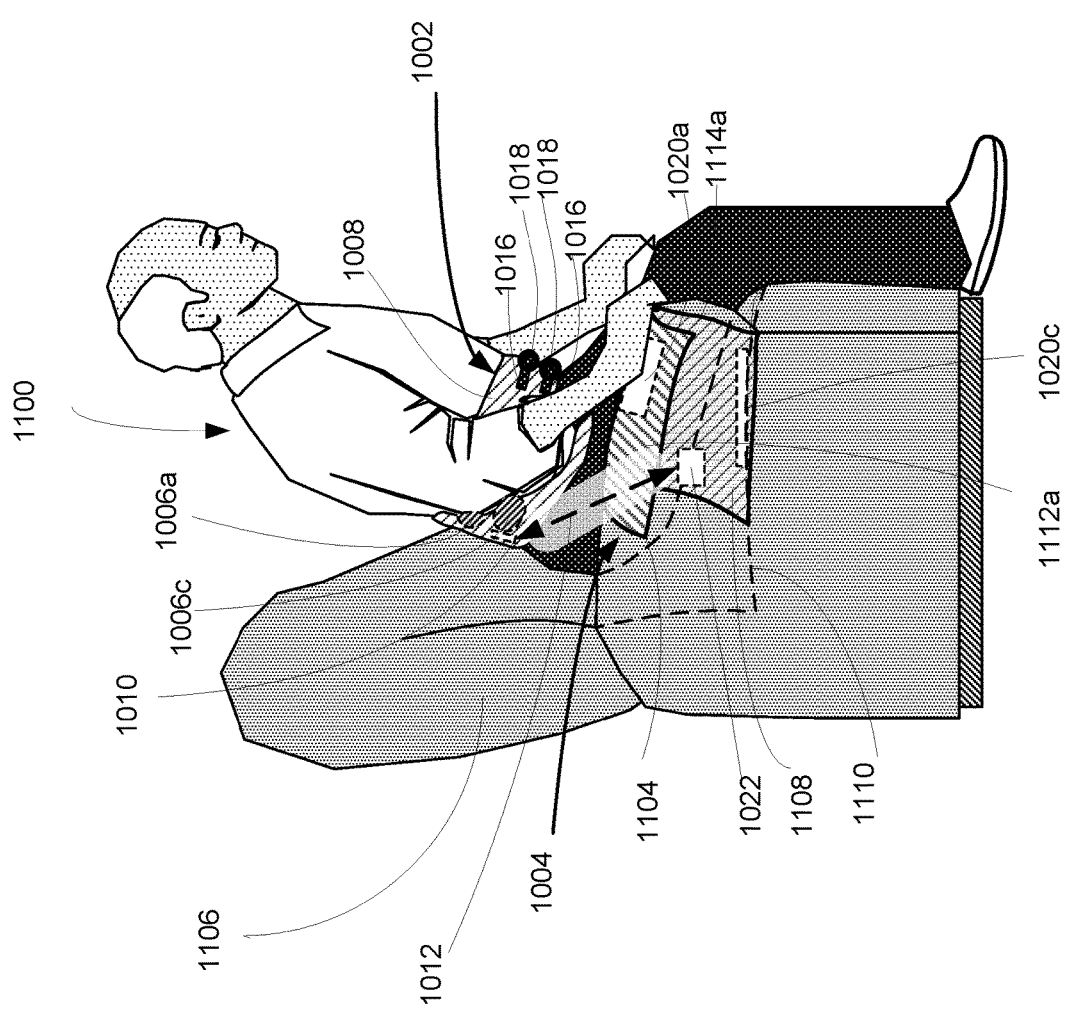
FIG. 11 is an illustration of a torso support system in use.

A torso support system as shown in FIG. 10 is depicted in use in FIG. 11. Subject 1100 wears torso support 1002 around his mid-section, as a back-brace. Positioning element 1008 is secured by straps 1016 and buckles 1018. Force applying elements (e.g., 1006a and 1006c visible in FIG. 11), also shown in FIG. 10, are positioned against the lower back region of subject 1100. Receiver 1010 in torso support 1002 receives activity signal 1012 from transmitter 1022 in remote sensor system 1004. Remote sensor system 1004 is configured as a pad 1104 that is placed on the chair 1106, with central portion 1108 including sensor 1020c positioned over seat 1110 of chair 1106 and end portion 1112a including sensor 1020a positioned over armrest 1114a of chair 1106. End portion 1112b and sensor 1020b of pad 1104 are not depicted in FIG. 11, but are as shown in FIG. 10.

Figure 12:
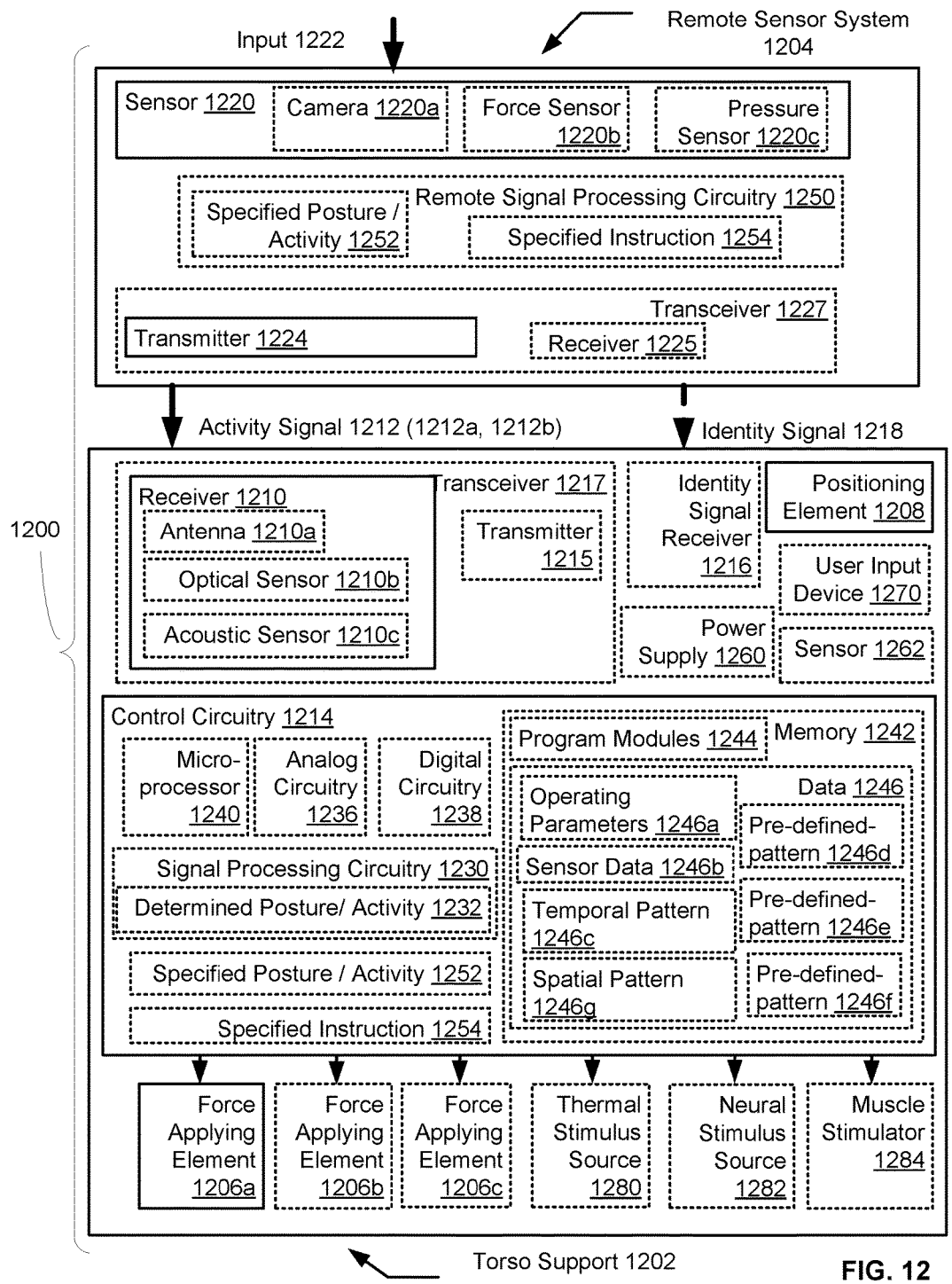
FIG. 12 is a block diagram of a torso support system.

FIG. 12 is a block diagram depicting components of a generalized torso support system 1200, which includes torso support 1202 and at least one remote sensor system 1204. Torso support 1202 includes at least one force applying element 1206a adapted to apply force to a localized region of a torso of a subject; at least one positioning element 1208 adapted to position the at least one force applying element with respect to the torso of the subject; and at least one receiver 1210 adapted to receive at least one activity signal 1212. Torso support 1202 may include additional force applying elements; three force applying elements 1206a-1206c are depicted in FIG. 12, for the purpose of illustration. However, in some embodiments, only a single force applying element may be used, while in other embodiments, larger numbers of force applying elements may be used. Force applying elements are as described in connection with FIG. 10, and are typically electromechanical in nature. It will be appreciated that a wide range of components may impart mechanical force or motion, such as rigid bodies, spring or torsional bodies, hydraulics, electro-magnetically actuated devices, and/or virtually any combination thereof. As used herein "electro-mechanical system" includes, but is not limited to, electrical circuitry operably coupled with a transducer (e.g., an actuator, a motor, a piezoelectric crystal, a Micro Electro Mechanical System (MEMS), etc.). Those skilled in the art will recognize that electro-mechanical as used herein is not necessarily limited to a system that has both electrical and mechanical actuation except as context may dictate otherwise.

Control circuitry 1214 is configured to control actuation of the at least one force applying element (e.g., 1206a-1206c) based at least in part on at the least one activity signal 1212 received by the at least one receiver 1210. Activity signal 1212 is indicative of the posture or activity of the subject detected by the at least one sensor system 1204 located remote from the torso support. Remote sensor system 1204 includes at least one sensor 1220 adapted to detect an input 1222 indicative of a posture or activity of a subject; and at least one transmitter 1224 adapted for transmitting the at least one activity signal 1212 indicative of the posture or activity of the subject. Transmitter 1224 can be adapted for transmitting various types of signals, e.g., an electromagnetic signal, a radiofrequency signal, an optical signal, an infrared signal, or an acoustic signal. It will be appreciated that various types of transmitters are known for transmitting the above signals, and the design of a transmitter adapted to transmit one or more type of signal is known to those having skill in the relevant art. See, e.g., U.S. Pat. No. 8,170,656 issued May 1, 2012, to Tan et al., and U.S. Published Application No. 2010/0198067 to Mahfouze et al., dated Aug. 5, 2010, each of which is incorporated herein by reference.

Figure 13:
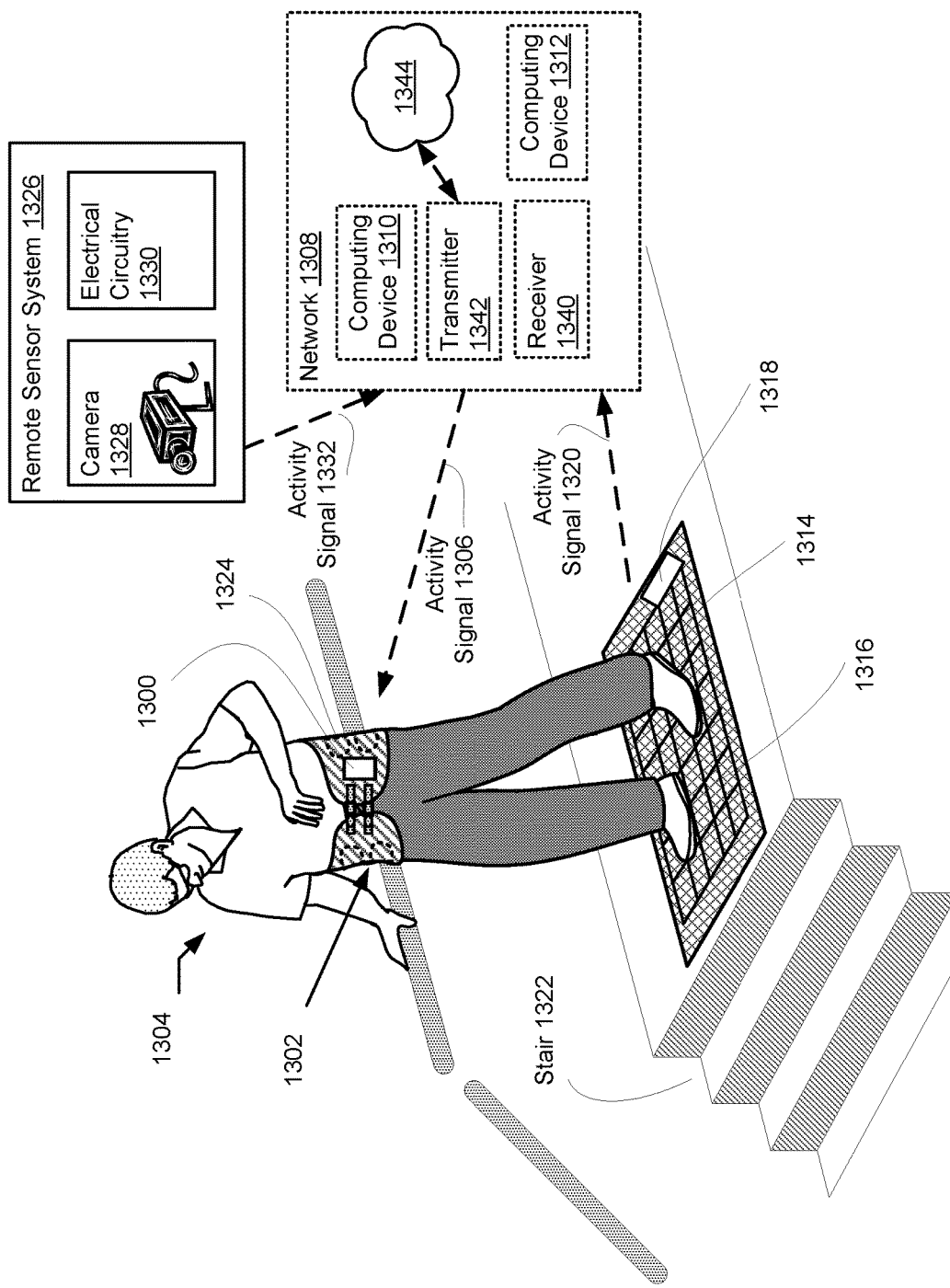
FIG. 13 is an illustration of an embodiment of a torso support system.
Figure 15:
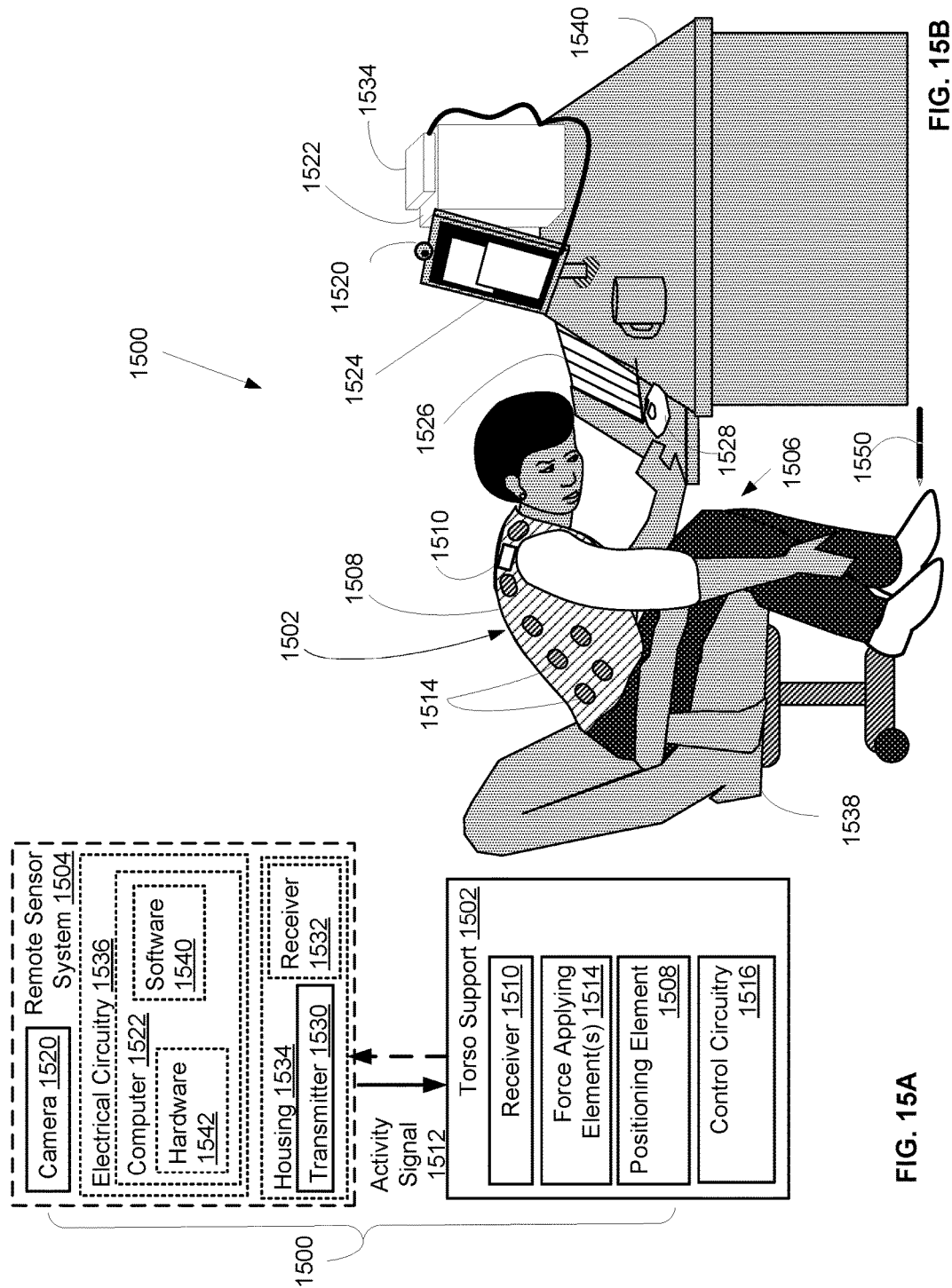
FIG. 15A is a block diagram of an embodiment of a torso support system.
FIG. 15B is an illustration of the torso support system of FIG. 15A.
Figure 16:
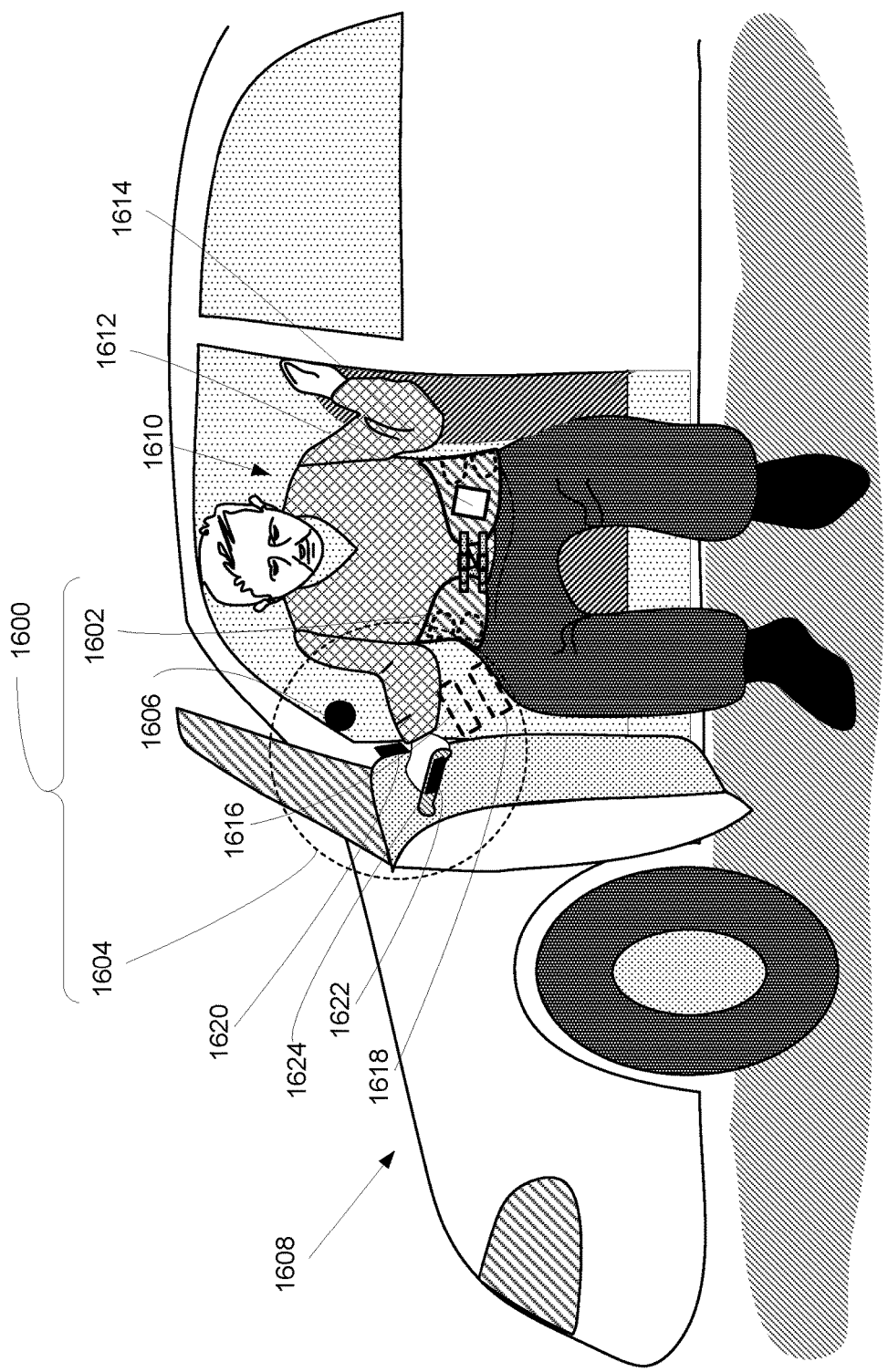
FIG. 16 is an illustration of an embodiment of a torso support system.

Sensor 1220 can include, for example, a camera 1220a, a force sensor 1220b, a pressure sensor 1220c, and/or various other types of sensors as described elsewhere herein or as known to those having skill in the relevant arts. In an aspect, if the at least one sensor in a remote sensor system 1204 includes a camera 1220a, the camera may be adapted for installation in an environment, as shown in FIG. 13; adapted for use with a computer, as shown in FIG. 15; or adapted for installation in a vehicle, as shown in FIG. 16. Sensor 1220 can be a pressure sensor, a motion sensor, a proximity sensor, or other types of sensors as known to those having skill in the art. A proximity sensor may be, for example, a micro-impulse radar sensor, an infrared sensor, an optical sensor, an electromagnetic sensor, an acoustic sensor, or any other type of sensor suitable for detecting the proximity of the subject to a location (with the location typically being defined or determined by one or both of the position of the sensor and the source of the signal detected by the sensor.) For example, proximity of the subject can be determined based on the strength of a signal transmitted from the torso support (or other signal source associated with the subject). In another aspect, the proximity of the subject can be determined based on the strength of a signal transmitted from a remote signal source, reflected from the subject, and detected by the sensor. In an aspect, the at least one sensor is adapted for use in connection with a vehicle (e.g., a car as in the embodiment of FIG. 16, or an airplane), an item of furniture (e.g., a bed or a chair, as in the embodiments of FIGS. 10, 11, 14A and 14B). The at least one sensor may be a component of a seat pad or seat, or a component of a bed or bed pad. In an aspect, the at least one sensor is adapted for use in connection with a floor, e.g., built into the floor, or as a component of a floor mat, as in the embodiment of FIG. 13. In an aspect, the at least one sensor is adapted for use in connection with a door, for example a door in a building, or a door of a vehicle such as a car, truck, or airplane, e.g., as in the embodiment of FIG. 16. In an aspect, the at least one sensor is adapted for use in connection with a hinge, a latch, a door frame, an arm rest, or a handle. The at least one sensor may be adapted for placement in or on a support rail, handle, armrest or handrest. The sensor may be built into any of the above structures during manufacture, or placed on or secured to a support rail, handle, armrest or handrest. For example, one or more sensors may take the form of or be incorporated into a pad, patch, or plate that can be secured to a structure such as a rail, handle, armrest or handrest with adhesive, screws, magnets or other fasteners, or by being placed over the structure and held in place by gravity and/or friction. In an aspect, the at least one sensor may be adapted for use in connection with a stair, for example for detecting that a subject has grasped a stair railing or walked across/through an area leading to or on the stair, e.g., as in the embodiment of FIG. 13.

In an aspect, torso support system 1200 may include both receiver 1210 and transmitter 1215, which in an aspect are components of a transceiver 1217, to provide two-way communication with remote sensor system 1204 or other system components. Similarly, remote sensor system 1204 may include both transmitter 1224 and receiver 1225, which in an aspect are components of transceiver 1227, to provide two-way communication with torso support system 1200 or provide for transmission of signals to or receipt of signals from other system components.

In an aspect, receiver 1210 in torso support 1202 is adapted to receive a wireless signal. The wireless signal may be an electromagnetic signal, e.g., a radio frequency signal, an optical signal, or an infrared signal, or it may be an acoustic signal or other wireless signal. Receivers for receiving wireless signals are well known in the electronic arts. For example, receiver 1210 may include an antenna 1210a suitable for receiving a radio frequency signal, optical sensor 1210b for receiving an optical signal, or acoustic sensor 1210c adapted to receive an acoustic signal.

In an aspect, the at least one transmitter 1224 in the remote sensor system 1204 is adapted for transmitting at least one activity signal 1212 to the at least one receiver 1210; in connection therewith, the at least one receiver 1210 is adapted to receive the at least one activity signal 1212 from the at least one transmitter 1224. Such a configuration is depicted, for example, in FIG. 11.

Torso support 1202 may also include identity signal receiver 1216 adapted to receive a signal 1218 indicative of an identity of the subject. Identity signal 1218 may be an electromagnetic or optical signal containing or encoding the identity of the subject. In connection therewith, control circuitry 1214 is configured to control actuation of the at least one force applying element 1206a-1206c based at least in part on the identity of the subject. For example, control circuitry 1214 may be configured to actuate force applying elements 1206a-406c only if the identity of the subject matches the identity of an authorized user. Or, the control circuitry can actuate force applying elements 1206a-1206c in a particular pattern adapted for a particular subject, based on the identity of the subject. For example, a torso support may be used by different subjects if it is loaned or rented to different subjects by a hospital or other medical equipment supplier. In various aspects, the identity of the subject is determined from an RFID signal, from an identifying number of an electronic device carried by or otherwise associated with the subject (e.g., a cell phone), through facial recognition, or other types of biometric ID. Identity signal receiver 1216 may be adapted to receive an electromagnetic signal, optical signal, or acoustic signal, for example.

In an aspect, control circuitry 1214 includes signal processing circuitry 1230 configured to process the at least one activity signal 1212 to determine the posture or activity 1232 of the subject. Control circuitry 1214 is configured to control actuation of the at least one force applying element (e.g., 1206a-1206c) based at least in part on the determined posture or activity 1232 of the subject.

In various aspects, signal processing circuitry 1230 may be configured to process an image signal, a pressure signal, a motion sensor signal, or a proximity sensor signal, for example, to determine the posture or activity of the subject. For example, methods for processing image signals to determine posture and activity are described in U.S. Pat. No. 7,616,779 issued Nov. 10, 2009 to Liau et al., U.S. Pat. No. 8,396,283, issued Mar. 12, 2013 to Iihoshi et al., U.S. Pat. No. 7,330,566, issued Feb. 12, 2008 to Cutler, or U.S. Pat. No. 7,728,839 issued Jun. 1, 2010 to Yang et al., each of which is incorporated herein by reference. In an aspect, signal processing circuitry 1230 is configured to process a proximity sensor signal; for example, signal processing circuitry 1230 may be configured to determine proximity of the subject to a location based upon a signal strength.

Control circuitry 1214 may include analog circuitry 1236 or digital circuitry 1238. In an aspect, control circuitry 1214 may include a microprocessor 1240. In an aspect, analog circuitry 1236 or digital circuitry 1238 are used in combination with microprocessor 1240. In an aspect, control circuitry 1214 includes software; e.g., control circuitry 1214 may include memory 1242 or other volatile or non-volatile storage structures to contain program modules 1244 used in the operation of torso support 1202. Memory 1242 may also contain various types of data 1246, including but not limited to operating parameters 1246a, sensor data 1246b, and pattern data 1246c, 1246d, 1246e, and 1246f, among others.

Active torso support 1202 may include various other elements, including power supply 1260, and one or more sensors 1262, which may sense various parameters relating to the operation of the torso support or to the status of the subject. For example, sensor 1262 may include an integrating accelerometer or an inclinometer. Data from accelerometers located on the hips of a subject can be used to distinguish walking, turning, ascending or descending stairs, as described in Sabelman et al., ("Accelerometric Activity Identification for Remote Assessment of Quality of Movement", Proceedings of the 26th Annual International Conference of the IEEE EMBS, San Francisco, Calif., USA, Sep. 1-5, 2005, pp. 4781-4784), which is incorporated herein by reference. Posture sensing may be performed, for example, as described in U.S. patent application Ser. No. 13/721,474, entitled Posture Dependent Active Torso Support, naming Roderick A. Hyde, Jordin T. Kare, Dennis J. Rivet, and Lowell L. Wood, Jr. as inventors, filed 20 Dec. 2012, which is incorporated herein by reference. Sensor 1262 include a motion sensor, for example, as described in U.S. Published Patent Application 2011/0082393, to Bort, dated Apr. 7, 2011, which employs piezoelectric sensors to detect deformation of an orthosis caused by movements of a body region, which is incorporated herein by reference. Other types of sensor 1262 include accelerometers, strain gauges, and pressure gauges as described in U.S. Published Patent Application 2001/0020143 to Stark et al., dated Sep. 6, 2001, which is incorporated herein by reference; and force and pressure sensors, as discussed in U.S. Pat. No. 5,827,209 issued Oct. 27, 1998 to Gross, which is incorporated herein by reference.

Detection of gait based on signals from accelerometers is performed, for example, as described by Derawi et al., "Improved Cycle Detection for Accelerometer Based Gait Authentication," IEEE Sixth International Conference on Intelligent Information Hiding and Multimedia Signal Processing," Oct. 15-17, 2010, pp. 312-317; Sabelman et al., "Accelerometric Activity Identification for Remote Assessment of Quality of Movement", Proceedings of the 26th Annual International Conference of the IEEE EMBS, San Francisco, Calif., USA, Sep. 1-5, 2005, pp. 4781-4784; Rong et al., "A Wearable Acceleration Sensor System for Gait Recognition," 2007 Second IEEE Conference on Industrial Electronics and Applications, May 23-25, 2007, pp. 2654-2659; and Sekine et al., "Discrimination of Walking Patterns Using Wavelet-Based Fractal Analysis," IEEE Transactions on Neural Systems and Rehabilitation Engineering, Vol. 10, No. 3, September 2002, pp. 188-196, each of which is incorporated herein by reference. The torso support can include other types of sensors, including but not limited to gyro sensors (e.g., to indicate inclination or leaning over of the subject), magnetometers (which provide angle information, or can be used with external field coils to provide both position and angle), and differential position sensors (using GPS or pseudo-GPS signals). A torso support can include one or multiple sensors, without limitation.

Remote devices suitable for use in connection with an active torso support can include other types of sensors, and can be located in the environment or located on the body of the subject at a position remote from the active torso support. In an aspect, an active torso support can receive information from multiple remote devices that include sensors. A remote device in the environment of the subject can include a sensor on stairs or a floor. For example, FIG. 13 depicts a remote device configured as a mat including resistive sensor grid, capable of sensing information regarding gait parameters such as stride length and stride cadence. In an aspect, remote sensors of various types as discussed herein (e.g., accelerometers, gyros, inclinometers, magnetometers, position sensors, force sensors, pressure sensors, motion sensors, proximity sensors) can be attached to or located in or on items carried by the subject, connected to the body of the subject, or otherwise physically interacting with the body of the subject, wherein the remote sensors provide information regarding movement or position of the item imparted to the item by the subject, and hence, movement or posture of the subject. For example, such items include, but are not limited to, sporting equipment such as baseball bats, tennis racquets, skis, eating implements (such as spoon or forks), grooming implements (such as a comb or toothbrush), and musical instruments and related items (e.g., drum sticks, a violin and/or bow, a trombone slide).

In another aspect, an active torso support can be operably coupled to a remote device located on the body of the subject and including at least one sensor including, but not limited to a gyro (e.g., to indicate inclination or leaning over of the subject), force sensor, pressure sensor, accelerometer (which may be a tri-axial accelerometer or an integrating accelerometer), magnetometer (which can be used to provide angle information, or can be used with external field coils to provide both position and angle), or differential position sensors (using GPS or pseudo-GPS signals). For example, accelerometers located on various portions of the body can be used to provide signals indicative of the gait of the subject, including on the legs (see, e.g., Torrealba et al., "Statistics-based technique for automated detection of gait events from accelerometer signals," Electronics Letters, 28 Oct. 2010, Vol. 46, No. 22, and Itoh et al., "Development of New Instrument for Evaluating Leg Motions Using Acceleration Sensors," Environmental Health and Preventive Medicine 12, 111-118, May 2007, each of which is incorporated herein by reference), legs and/or arms (see Mannini et al., "Accelerometry-Based Classification of Human Activities Using Markov Modeling," Computational Intelligence and Neuroscience, Vol. 2011, Article ID 647858, published online 4 Sep. 2011, which is incorporated herein by reference), and/or head (see Sabelman et al., "Accelerometric Activity Identification for Remote Assessment of Quality of Movement", Proceedings of the 26.sup.th Annual International Conference of the IEEE EMBS, San Francisco, Calif., USA, Sep. 1-5, 2005, pp. 4781-4784, which is incorporated herein by reference).

In an aspect, a torso support includes a neural activity sensor adapted to sense neural activity. In another aspect, torso support includes a muscle activity sensor adapted to sense muscle activity. An electromagnetic sensor (e.g., electromagnetic transducer 412 in FIG. 4) may be used for sensing electrical activity produced by a nerve, nerve plexus, or other neural structure, or by a muscle (including cardiac or skeletal muscle) below the skin, as described for example in U.S. Pat. No. 8,170,656 issued May 1, 2012, to Tan et al., which is incorporated herein by reference. Magnetic fields produced by neural activity can be sensed, for example, by a magnetometer, e.g., as described by Sander et al. in "Magnetoencephalography with a chip-scale atomic magnetometer," Biomedical Optics Express, May 2012, Vol. 3, No. 5, p. 982, which is incorporated herein by reference. Sensed neural activity may provide information about the gait of the subject, or about pain or other sensations of the subject. Sensed muscle activity may provide information about the gait or muscle fatigue, for example.

In an aspect, remote sensor system 1204 includes remote signal processing circuitry 1250 configured to process the input 1222 indicative of a posture or activity of a subject to produce activity signal 1212a specifying the posture or activity 1252 of the subject. At least one transmitter 1224 is adapted for transmitting the activity signal 1212a specifying the posture or activity of the subject, and at least one receiver 1210 is adapted to receive the at least one activity signal 1212a specifying the posture or activity 1252 of the subject, detected by the at least one sensor system located remote from the torso support. Control circuitry 1214 is configured to control actuation of the at least one force applying element 1206a-1206c based at least in part on the posture or activity of the subject specified by the at least one activity signal 1212a. For example, input 1222 may include information indicative of posture or activity of a signal.

In an aspect, the remote sensor system 1204 includes remote signal processing circuitry 1250 configured to process the input 1222 indicative of a posture or activity of a subject to produce an activity signal 1212b specifying least one instruction 1254 corresponding to the posture or activity of the subject. At least one transmitter 1224 is adapted for transmitting the activity signal 1212b specifying the at least one instruction 1254, wherein the at least one receiver 1210 is adapted to receive the at least one activity signal 1212b specifying the least one instruction 1254. Control circuitry 1214 is configured to control actuation of the at least one force applying element 1206a-1206c based at least in part on the at least one instruction 1254. In another aspect at least one activity signal 1212b receivable by the at least one receiver 1210 has been processed to specify at least one instruction 1254 corresponding to the posture or activity of the subject, wherein the control circuitry 1214 is configured to control actuation of the at least one force applying element 1206a-1206c based on the at least one instruction 1254.

As an example of the various alternative signal processing approaches described generally above, input 1222 may include, for example, a signal from a pressure sensor on a chair pad or arm rest (e.g., as depicted in FIGS. 10 and 11), which is an analog voltage signal from a pressure sensor 1220c that is carried on a wire to transmitter 1224. The analog voltage is encoded into an electromagnetic signal (activity signal 1212) that is transmitted from transmitter 1224 to receiver 1210 in torso support system 1200, where signal processing may be performed on the signal by signal processing circuitry 1230. Alternatively, or in addition, an analog voltage signal from pressure sensor 1220c is delivered to remote signal processing circuitry 1250, and the signal may be processed to determine a posture or activity specified by the pressure signal. For example, a high pressure signal from a sensor in a chair seat may be indicative of a subject sitting in the chair, whereas a high pressure signal from a sensor in the armrest of a chair may indicate preparation of the subject to sit in the chair. Thus, the specified posture or activity 1252 may be, for example, "seated" or "preparing to sit." Accordingly, an activity signal 1212a representing particular postures or activities (e.g., activity signal 1212a may have a first value to indicate "seated" or a second value to indicate "preparing to sit") is transmitted from transmitter 1224 to receiver 1210 in torso support system 1200. Control circuitry 1214 then controls the torso support based on the specified posture or activity 1252 represented in activity signal 1212a. As a further alternative, remote signal processing circuitry 1250 may process the signal from pressure sensor 1220c to specify an instruction 1254 corresponding to the posture or activity of the subject. For example, the instruction may be to activate the torso support to provide additional support if the subject is preparing to sit, or deactivating the torso support (or maintaining the torso support in a deactivated state) if the subject is already sitting. Thus activity signal 1212b may include a specified instruction ("activate torso support", "deactivate torso support") that corresponds to the detected posture or activity of the subject, as determined by remote signal processing circuitry 1250.

In an aspect, control circuitry (e.g., control circuitry 1214 or control circuitry 406 in FIG. 4) includes actuation circuitry (not specifically shown, but a subsystem of the control circuitry) configured to control actuation of the at least one force applying element responsive to a change in the gait of the subject. For example, actuation circuitry can be configured to control actuation of the at least one force applying element as a function of the speed of the gait. In an aspect, actuation circuitry is configured to control actuation of the at least one force applying element to provide additional support to the torso of the subject responsive to detection of the change in the gait of the subject. In another aspect, actuation circuitry is configured to control actuation of the at least one force applying element to provide less support to the torso of the subject responsive to detection of the change in the gait of the subject.

In an aspect, control circuitry includes gait analysis circuitry (again, not specifically shown, but a subsystem of the control circuitry) configured to detect a change in the gait of the subject to walking, running, climbing stairs, or descending stairs, or from these or other active gaits to standing still. For example, Mannini et al. describe processing of signals from accelerometers worn on a subject's hip, wrist, arm, ankle and thigh to distinguish a variety of activities, including walking, running, standing, and climbing stairs (see Mannini et al., "Accelerometry-Based Classification of Human Activities Using Markov Modeling," Computational Intelligence and Neuroscience, Vol. 2011, Article ID 647858, published online 4 Sep. 2011, and Sekine et al., "Discrimination of Walking Patterns Using Wavelet-Based Fractal Analysis," IEEE Transactions on Neural Systems and Rehabilitation Engineering, Vol. 10, No. 3, September 2002, pp. 188-196, each of which is incorporated herein by reference.) Gait analysis circuitry may be configured to detect a change in the gait of the subject indicative of the subject stumbling, subject falling, or changing direction. Data from accelerometers located on the hips of a subject can be used to distinguish walking, turning, ascending or descending stairs, as described in Sabelman et al., ("Accelerometric Activity Identification for Remote Assessment of Quality of Movement", Proceedings of the 26th Annual International Conference of the IEEE EMBS, San Francisco, Calif., USA, Sep. 1-5, 2005, pp. 4781-4784), which is incorporated herein by reference.

In an aspect, an active torso support or other wearable item includes an inclinometer adapted to generate an inclination signal indicative of an inclination of at least a portion of the body of the subject. For example, a MEMS type digital inclinometer (for example, an Analog Devices ADIS 16209) that can be used to detect the inclination of the subject's torso. Examples of other suitable sensors are gyro sensor, magnetometer, and differential position sensors. An inclinometer can be used in combination with other sensors to provide information regarding the angular position of the subject's limbs or spine, which is indicative of aspects of the subjects gait, and may also provide information regarding disturbances in gait, including tilting, swaying or falling. In connection therewith, gait analysis circuitry may be configured to generate a signal indicative of the gait of the subject based at least in part on the inclination signal. Similarly, actuation circuitry may be configured to control actuation of the at least one force applying element responsive to the signal indicative of the gait of the subject based at least in part on the inclination signal.

In an aspect, control circuitry 1214 is configured to control actuation of the at least one force applying element 1206a-1206c based at least in part on a temporal pattern 1246c stored in memory 1242. Controlling actuation according to a temporal pattern may be as simple as applying a constant force at a selected location for a specific duration (e.g., a duration corresponding to an expected duration of a particular activity or a particular motion, such as a portion of a gait cycle), or applying a force that gradually ramps up to a maximum value as a function of time.

In an aspect, control circuitry 1214 is configured to initiate actuation of the at least one force applying element 1206*a*-1206*c* based at least in part on the at least one activity signal (1212, 1212*a*, or 1212*b*). In another aspect, control circuitry 1214 is configured to cease actuation of the at least one force applying element based at least in part on the at least one activity signal (1212, 1212*a*, or 1212*b*).

In some aspects, control circuitry 1214 is configured to control actuation of the at least one force applying element 1206*a*-1206*c* according to a pre-defined pattern selectable from a plurality of pre-defined patterns, e.g., from pre-defined patterns 1246*d*, 1246*e*, and 1246*f* stored in memory 1242. For example, the plurality of pre-defined patterns may include patterns corresponding to a plurality of pre-defined postures or activities of the subject (including, but not limited to, standing, sitting, lying, walking, getting up, sitting down, leaning forward, twisting, or lying down). The pre-defined pattern may be selected from the plurality of pre-defined patterns in a number of ways. For example, the torso support may include a user input device 1270, and the pre-defined pattern may be selectable from the plurality of pre-defined patterns based upon an input received by the user input device. Alternatively, or in addition, the pre-defined pattern may be selectable from the plurality of pre-defined patterns based at least in part upon the at least one activity signal (1212, 1212*a*, or 1212*b*).

In an aspect, torso support includes at least two spatially separated force applying elements 1206*a*-1206*c* each adapted to apply force to a localized region of the torso of the subject, wherein the at least two spatially separated force applying elements are positioned at different positions with respect to the torso of the subject by the at least one positioning element 1208. In an aspect, control circuitry 1214 is configured to control actuation of the at least two spatially separated force applying elements based at least in part on a temporal pattern 1246*c*. In addition, or as an alternative, control circuitry 1214 is configured to control actuation of the at least two spatially separated force applying elements based at least in part on a spatial pattern 1246*g*. For example, a spatial pattern 1246*g* provides for applying force at several spatially separated locations to support several different muscles (or different portions of a larger muscle) that are loaded or stressed during a particular posture, gait, or activity. More complex temporal or spatio-temporal patterns (e.g., cyclical patterns) may also be employed. Cyclical patterns may be matched to the gait cycle, for example. Control circuitry 1214 may be configured to control actuation of the at least two force applying elements 1206*a*-1206*c* according to a pre-defined pattern selectable from a plurality of pre-defined patterns. Again, as discussed above, the torso support may include a user input device 1270, and the pre-defined pattern may be selectable from the plurality of pre-defined patterns 1246*d*-1246*f* based upon an input received by the user input device 1270. Alternatively, or in addition, the pre-defined pattern may be selectable from the plurality of pre-defined patterns based at least in part upon the at least one activity signal (1212, 1212*a*, or 1212*b*). The plurality of pre-defined patterns includes patterns corresponding to a plurality of pre-defined postures or activities of the subject, including one or more of standing, sitting, lying, walking, getting up, sitting down, leaning forward, twisting, or lying down.

In an aspect, control circuitry 1214 is configured to control actuation of the at least one force applying element by controlling a pattern of force applied by the at least one force applying element. In another aspect, control circuitry 1214 is configured to control actuation of the at least one force applying element by controlling a pattern of motion generated by the at least one force applying element.

In an aspect, active torso support 1202 includes thermal stimulus source 1280 configured to deliver a thermal stimulus to at least a portion of the torso of the subject. Thermal stimulus source 1280 may include, for example, a resistive element, an infrared source, a microwave source, an acoustic energy source, or other elements capable of providing localized heating to the skin or underlying tissues. A thermal stimulus may be applied to stimulate blood circulation, promote healing, enhance comfort of sore or injured muscles, or serve as a counter-stimulus to reduce sensation of pain, for example.

In an aspect, active torso support 1202 includes neural stimulus source 1282 configured to deliver a stimulus to a neural structure in the torso of the subject. In an aspect, active torso support 1202 includes a muscle stimulator 1284 configured to deliver a stimulus to a muscle in the torso of the subject. A neural stimulator 1282 or muscle stimulator 1284 may include an electrode for delivering an electrical stimulus, or one or more coils for delivering a magnetic stimulus, for example, either of which can be driven by an appropriately configured electrical control signal, as known to those having skill in the art. (See, for example, U.S. Pat. No. 8,285,381 issued Oct. 9, 2012 to Fahey et al., which is incorporated herein by reference). Other types of neural or muscle stimulators may be used, as known to those having skill in the art. Nerve and/or muscle stimulation can be used to activate muscles to provide a higher level of strength or stability in the back, or to block or counter pain signals, for example.

As an alternative to, or in addition to, providing nerve or muscle stimulation to activate muscles, a feedback signal may be provided to the subject to prompt the subject to voluntarily activate muscles. Such a feedback signal may take the form of a haptic signal (e.g., vibration, pressure, an electrical stimulus), or an audio or visual feedback signal, e.g., as described in U.S. Pat. No. 8,170,656 issued May 1, 2012, to Tan et al., which is incorporated herein by reference. In an aspect, one or more haptic elements are attached to or carried by a positioning element worn on the body of the subject. In another aspect, haptic elements can be provided in a remote device carried by the subject, such as a cell phone. Audio or visual feedback can be provided to the subject via audio or visual feedback devices (displays, speakers, buzzers, etc.) incorporated into wearable items or by a computing/communication system worn on the body of the subject or operatively connected to components worn on the body of the subject.

As shown in FIG. 12, in an aspect, receiver 1210 on a torso support is adapted to receive the at least one activity signal (1212, 1212*a*, 1212*b*) from the at least one remote sensor system 1204. An example of such a system is depicted in FIGS. 10 and 11.

In another aspect, as shown in FIG. 13, a receiver 1300 on a torso support 1302 worn by subject 1304 is adapted to receive at least one activity signal 1306 from a network 1308 including one or more computing devices 1310, 1312 in communication with at least one sensor system 1314. In the example of FIG. 13, remote sensor system 1314 is a floor mat including resistive sensor grid 1316 (as described in Middleton et al., "A floor sensor system for gait recognition," Fourth IEEE Workshop on Automatic Identification Advanced Technologies, 2005, pp. 171-176, Digital Object Identifier: 10.1109/AUTOID.2005.2, which is incorporated herein by reference). Remote sensor system 1314 also includes transmitter 1318, configured to transmit an activity signal 1320 indicative of the posture or activity of subject 1304. In the example of FIG. 13, remote sensor system 1314 is located at the top of a stair 1322, and is activated when subject 1304 walks across it to approach stair 1322. For example, force applying elements 1324 on torso support 1302 may be activated when subject 1304 walks across remote sensor system 1314, to provide additional support as subject 1304 descends stair 1322. Torso support 1302 may be activated for a fixed amount of time expected to correspond to the amount of time needed to descend stair 1322, for example.

In an aspect, the proximity sensor is a perimeter sensor, that is, the proximity sensor is configured to determine whether the subject has crossed a perimeter. Crossing of the perimeter may indicate that the subject is heading toward an area in which activation of the torso support is to be adjusted. For example, a perimeter sensor may be located at the top and/or bottom of a stairway to determine the approach of the subject to the stairway and corresponding need to activate the torso support to provide support to the subject as he or she ascends or descends the stairs. A perimeter sensor may include, for example, an infrared light source positioned on one side of a hallway leading to a stairway and infrared sensor positioned on the opposite side of the hallway such that a person passing through the hallway toward the stairway breaks the beam, producing change in the signal sensed with the infrared sensor.

In addition, or as an alternative, network 1308 may be in communication with an additional remote sensor system 1326. Remote sensor system 1326 includes a camera 1328 mounted in the environment of subject 1304, which includes an area occupied by the subject, which here is depicted as a hallway, but could be, for example, a bedroom, an office, a vehicle, a hospital room, a room of a care facility, etc. Electrical circuitry 1330 associated with remote sensor system 1326 provides for data processing and transmission of activity signal 1332 to network 1308. The posture or activity of subject 1304 can be determined, for example, by image analysis, e.g., as described in U.S. Pat. No. 7,330,566, issued Feb. 12, 2008 to Cutler, or U.S. Pat. No. 7,728,839 issued Jun. 1, 2010 to Yang et al., each of which is incorporated herein by reference. Network 1308 includes at least one receiver 1340, for receiving activity signal 1320 and/or activity signal 1332 from remote sensor systems 1314 and 1326, respectively, and at least one transmitter 1342, for transmitting activity signal 1306 to receiver 1300 on torso support 1302. Network 1308 includes at least one computing device 1310, which is a computing device located locally (for example, in the subject's house), but which may be in communication with other computing devices located either locally (e.g., computing device 1312) or remotely, via the internet or other computing network, as represented by "cloud" 1344 in FIG. 13. Data acquisition, processing, analysis, and storage may be performed locally or remotely within network 1308. In an aspect, the at least one transmitter 1318 in remote sensor system 1314 is adapted for transmitting at least one activity signal 1320 to network 1308 including one or more computing devices, and the at least one receiver 1300 in torso support 1302 is adapted to receive at least one activity signal 1306 from network 1308. As can be seen, activity signal 1306 is not necessarily the same signal as activity signal 1320, although it may contain some or all of the same information contained in activity signal 1320. Signal 1306 may also include additional information, including, e.g., information from activity signal 1332.

Figure 14:
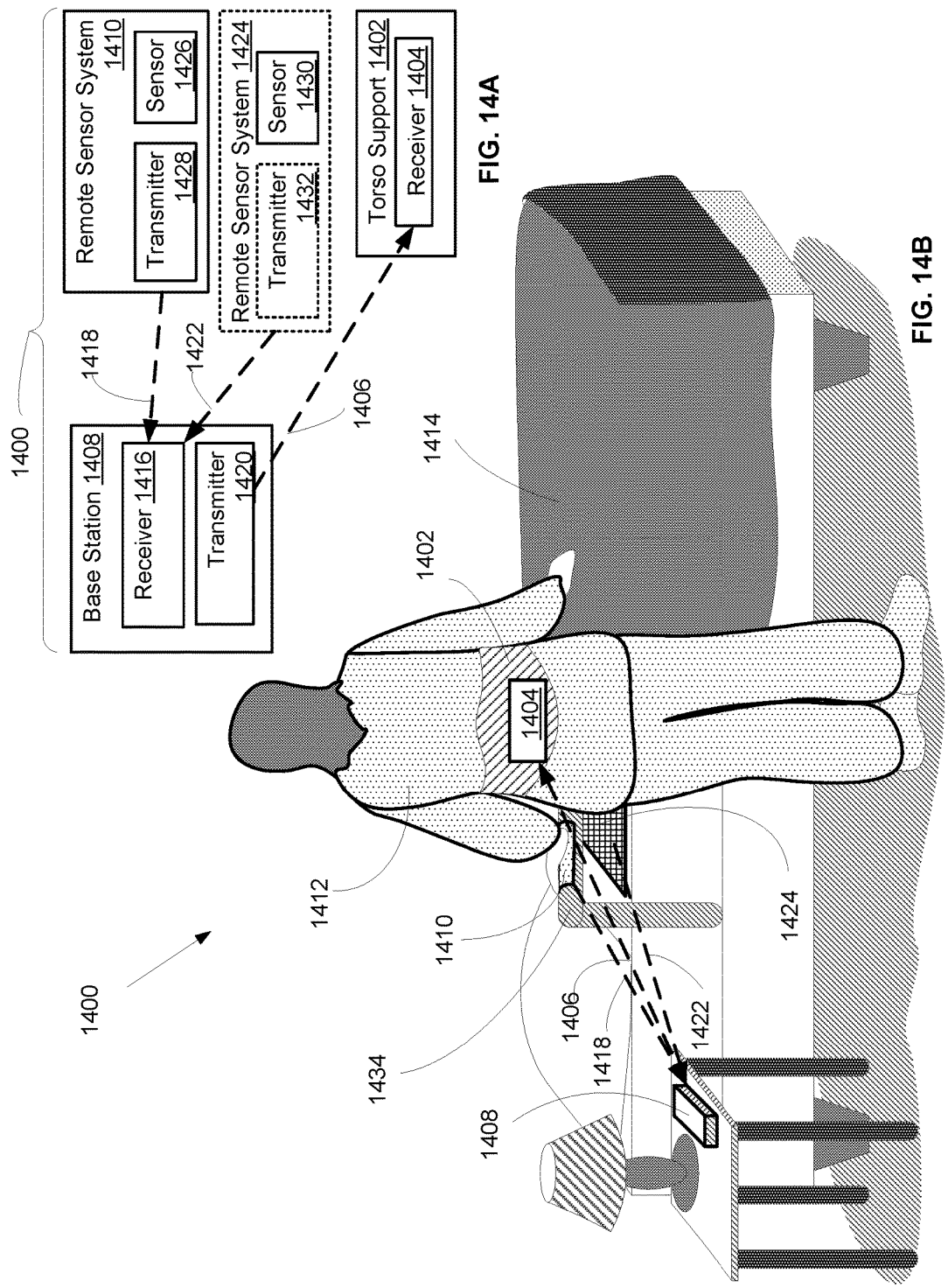
FIG. 14A is a block diagram of an embodiment of a torso support system.
FIG. 14B is an illustration of a torso support system of FIG. 14A.

FIG. 14A depicts another example of a torso support system 1400 in which a torso support 1402 includes a receiver 1404 adapted to receive at least one activity signal 1406 from a base station 1408 which is in communication with at least one sensor system 1410. Torso support system 1400 is depicted in block diagram form in FIG. 14A, and illustrated in FIG. 14B. Torso support 1402 is worn by subject 1412 and can be controlled to provide support to the subject's torso as subject 1412 gets in and out of a bed 1414, for example. In an aspect, base station 1408 includes receiver 1416 for receiving an activity signal 1418 from remote sensor system 1410. Base station 1408 also includes a transmitter 1420 for transmitting an activity signal 1406 to receiver 1404 in torso support 1402. In an aspect, receiver 1416 in base station 1408 also receives an activity signal 1422 from an additional remote sensor system 1424. Although base station 1408 is depicted as including a single receiver 1416 in FIG. 14, in other aspects multiple receivers may be used, without limitation. Similarly, one or multiple receivers may be used in the various embodiments of systems and system components depicted and described herein, as appropriate for the number and types of signals being transmitted between system components. Remote sensor system 1410 includes at least one sensor 1426 and transmitter 1428, and additional remote sensor system 1424 includes at least one sensor 1430 and transmitter 1432. Remote sensor system 1410 includes a sensor 1426 attached to or incorporated into bed rail 1434, and adapted to detect when subject 1412 applies pressure to bed rail 1434, either in anticipation of getting into bed 1414, as depicted in FIG. 14B, or in preparation for rising from bed 1414 (not shown). Sensor 1426 may detect force, pressure, change in capacitance or conductance, stress, strain, or temperature. In other aspects, sensor 1426 is placed on or incorporated into other portions of the bed rail 1434 or bed 1414. Additional remote sensor system 1424, which takes the form of a pad placed on bed 1414 (or potentially built into the mattress, bed frame, or other portion of bed 1414, can be used to detect whether subject 1412 is in bed 1414, e.g., by sensing pressure produced by subject 1412 lying on a pad. In an aspect, information from remote sensor system 1410 and additional remote sensor system 1424 can be used to determine whether subject 1412 is preparing to get into or out of bed 1414. Various other types of sensors could be used to distinguish whether the subject is in the bed or not. Sensed parameters could include, but are not limited to, strain or vibration in the bed frame, or temperature.

FIG. 15A is a block diagram of a torso support system 1500, including a torso support 1502 and remote sensor system 1504, which is configured for use by a subject 1506. Torso support system 1500 is illustrated in greater detail in FIG. 15B. Torso support 1502 includes positioning element 1508 configured as a vest worn by a subject 1506. Torso support 1502 includes a receiver 1510 for receiving an activity signal 1512, one or more force applying elements 1514, and control circuitry 1516 for controlling actuation of force applying elements 1514.

In remote sensor system 1504, the sensor includes a camera 1520, which is adapted for use with a computer 1522. Camera 1520 may be a webcam integrated into monitor 1524, or a camera packaged separately and connected to computer 1522 via either a wired or wireless connection (for example, a USB 2.0 or 2.0 camera). Such cameras are readily available and well-known in the art. Computer 1522 is used in combination with standard input devices such as keyboard 1526 and mouse 1528, for example. Remote sensor system 1504 also includes transmitter 1530 which is adapted for transmitting at least one activity signal indicative of the posture or activity of subject 1506, sensed by camera 1520, and optionally receiver 1532. In an aspect, transmitter 1530 and receiver 1532, if used, may be packaged in housing 1534. Housing 1534 can be connected to computer 1522 and other components of remote sensor system 1504 by a wired connection, as depicted in FIG. 15B, or by a wireless connection. As discussed elsewhere herein, receiver 1532 may be used to enable two-way communication between remote sensor system 1504 and torso support 1502. Remote sensor system 1504 also includes electrical circuitry 1536, which may perform processing of the signal produced by camera 1520, for example. The torso support system 1500 depicted in FIGS. 15A and 15B is configured for use by subject 1506 during the activity of working on computer 1522 while seated in chair 1538 at desk 1540. While computer 1522 is suitable for use by subject 1506 in a conventional manner (for word processing, computer programming, etc. without limitation), computer 1522 may also form a component of remote sensor system 1504, and may contain software 1540 and/or hardware 1542 that form a portion of the electrical circuitry 1536 of remote sensor system 1504, as shown in FIG. 15A. Alternatively, or in addition, some or all of electrical circuitry 1536 may be packaged in housing 1534.

Software 1540 and hardware 1542 can include image processing hardware and/or software used to determine an activity or posture of the subject from an image obtained from camera 1520. Such image processing hardware and/or software may, for example, include or generate a model of the background of the image, segment the image, identify the subject in the image, and analyze the image to determine activity or posture of the subject, e.g., based on parameters such as the angle of the torso relative to the hips, or angle of the shoulders relative to the hips. Processing of an image to determine position or posture-related information may be, for example, as described in U.S. Pat. No. 7,616,779 issued Nov. 10, 2009 to Liau et al., U.S. Pat. No. 8,396,283, issued Mar. 12, 2013 to Iihoshi et al., U.S. Pat. No. 7,330,566, issued Feb. 12, 2008 to Cutler, or U.S. Pat. No. 7,728,839 issued Jun. 1, 2010 to Yang et al. If it is determined that the position or posture of subject 1506 is one that is expected to result in injury or discomfort (e.g., bending and twisting motion/to retrieve a dropped item such as pencil 1550 from the floor is detected through processing of an image obtained with camera 1520), force applying elements 1514 on torso support 1502 are activated in a manner expected to prevent or minimize such injury or discomfort. As described in connection with FIG. 12, activity signal 1512 may contain information indicative of the posture or activity of the subject, or in some aspects may specify a posture or activity, or an instruction corresponding to a posture or activity of the subject.

FIG. 16 illustrates an embodiment of torso support system 1600, including torso support 1602 and remote sensor system 1604 in which the sensor includes at least one camera 1606 adapted for installation in a car 1608. Camera 1606 is a driver-facing dashboard camera or similar camera. Torso support 1602 is worn by subject 1610. Torso support 1602 is similar to the torso support described in connection with FIGS. 1 and 11, and includes receiver 1612, control circuitry (not shown), and force applying elements 1614. Remote sensor system 1604 includes remote signal processing circuitry 1616 and transmitter 1618. In addition, remote sensor system 1604 includes door opening sensor 1620 and door handle sensor 1622.

As noted herein above, getting in and out of a vehicle may be difficult for a person with lower back pain. The person may be advised to break down the motions to separate twisting motion from muscular effort to raise or lower the body. For example, in order to get into a car, subject 1610 may be instructed to support the weight of his body with his arms, by holding onto door handle 1624, as well as with his legs, and maintain hips and shoulders in alignment while lowering his body into the car seat. Then, after subject 1610 is seated in the car seat, he is instructed to swing his legs into car 1608 while turning his body, again maintaining hips and shoulders in alignment.

Thus, entry of subject 1610 into car 1608 is indicated by a signal from door handle sensor 1622 produced when subject 1610 applies pressure to door handle sensor 1622 as a portion of his body weight is transferred to the car via his arm. The process for exiting the car is substantially the reverse; subject 1610 swings his legs out of car 1608 while turning his body, maintaining hips and shoulders in alignment, and then rises, applying pressure to door handle sensor 1622 while using both arm and leg muscles to rise. Entering and exiting the car are preceded by opening of the car door; hence in an aspect, opening of the car door, which is detected by door opening sensor 1620, is an indicator of impending activity during which the back will require additional support. Door opening sensors are conventional in modern cars.

While activity on door opening sensor 1620 may indicate either that a person is about to enter or exit the car, these two activities can be distinguished by determining whether a person is sitting in the car seat (in which case door opening indicates that the person is about to exit the car) or not (in which case door opening indicates that the person is about to enter the car). Presence of subject 1610 in car 1608, as well the position/orientation of subject 1610, can be detected as described in U.S. Pat. No. 7,396,283 issued Mar. 12, 2013 to Iihoshi et al., which is incorporated herein by reference. Processing of signals from door opening sensor 1620, camera 1606, and door handle sensor 1622, e.g., to determine the posture and activity of subject 1610, is performed by remote signal processing circuitry 1616, and posture or activity signal is transmitted to receiver 1612 in torso support 1602 by transmitter 1618. Torso support 1602 functions as described herein above, to provide support to the back of subject 1610 during twisting, sitting, and standing motions that are likely to deleteriously load the subject's back, depending upon the specific needs of subject 1610. It will be appreciated that remote signal processing circuitry 1616 may be in communication with, or include portions of the electrical circuitry and/or computer system of car 1608, in order to receive data from sensors (e.g., door opening sensor 1620) built into car 1608 and (optionally) to share processing through the use of appropriately configured hardware and software.

In a general sense, those skilled in the art will recognize that the various embodiments described herein can be implemented, individually and/or collectively, by various types of electrical circuitry having a wide range of electrical components such as hardware, software, firmware, and/or virtually any combination thereof, limited to patentable subject matter under 35 U.S.C. § 101. Electrical circuitry (e.g., control circuitry 406 and electrical circuitry 444 depicted in FIG. 4, and control circuitry 1214 and remote signal processing circuitry 1250 depicted in FIG. 12, as well as other electrical circuitry) includes electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs (e.g., graphene based circuitry). In a general sense, those skilled in the art will recognize that the various aspects described herein which can be implemented, individually and/or collectively, by a wide range of hardware, software, firmware, and/or any combination thereof can be viewed as being composed of various types of "electrical circuitry."

Those skilled in the art will recognize that at least a portion of the devices and/or processes described herein can be integrated into a data processing system. Those having skill in the art will recognize that a data processing system generally includes one or more of a system unit housing, a video display, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system may be implemented utilizing suitable commercially available components, such as those typically found in data computing/communication and/or network computing/communication systems.

Figure 17:
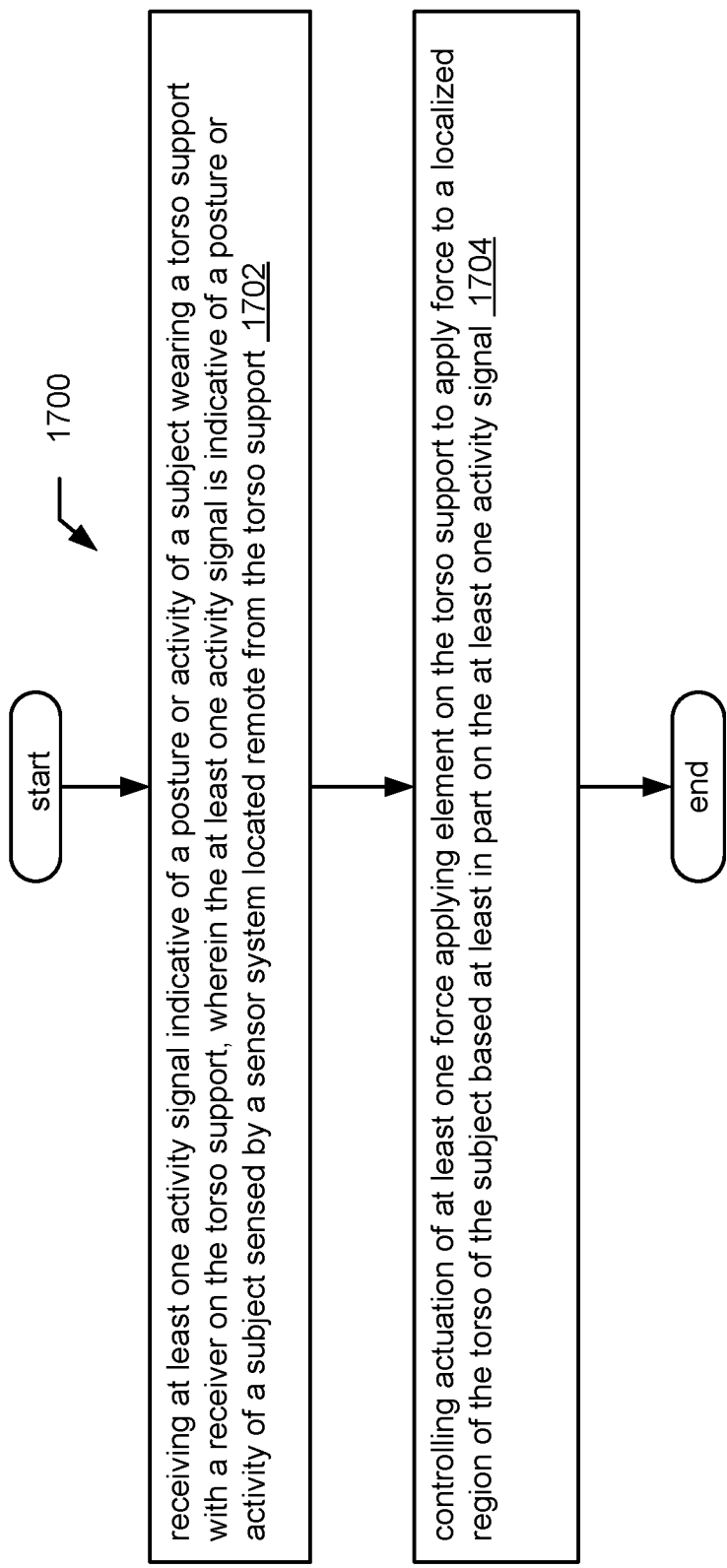
FIG. 17 is a flow diagram of a method of controlling a torso support.

FIG. 17 depicts a method 1700 of controlling a torso support. Method 1700 includes receiving at least one activity signal indicative of a posture or activity of a subject wearing a torso support with a receiver on the torso support, wherein the at least one activity signal is indicative of a posture or activity of a subject sensed by a sensor system located remote from the torso support at 1702; and controlling actuation of at least one force applying element on the torso support to apply force to a localized region of the torso of the subject based at least in part on the at least one activity signal at 1704. Here and elsewhere, a solid line around a method step indicates a fundamental aspect of the method, while a dashed line indicates an optional or alternative step that may be included in some, but not all, implementations of the method.

Figure 18:
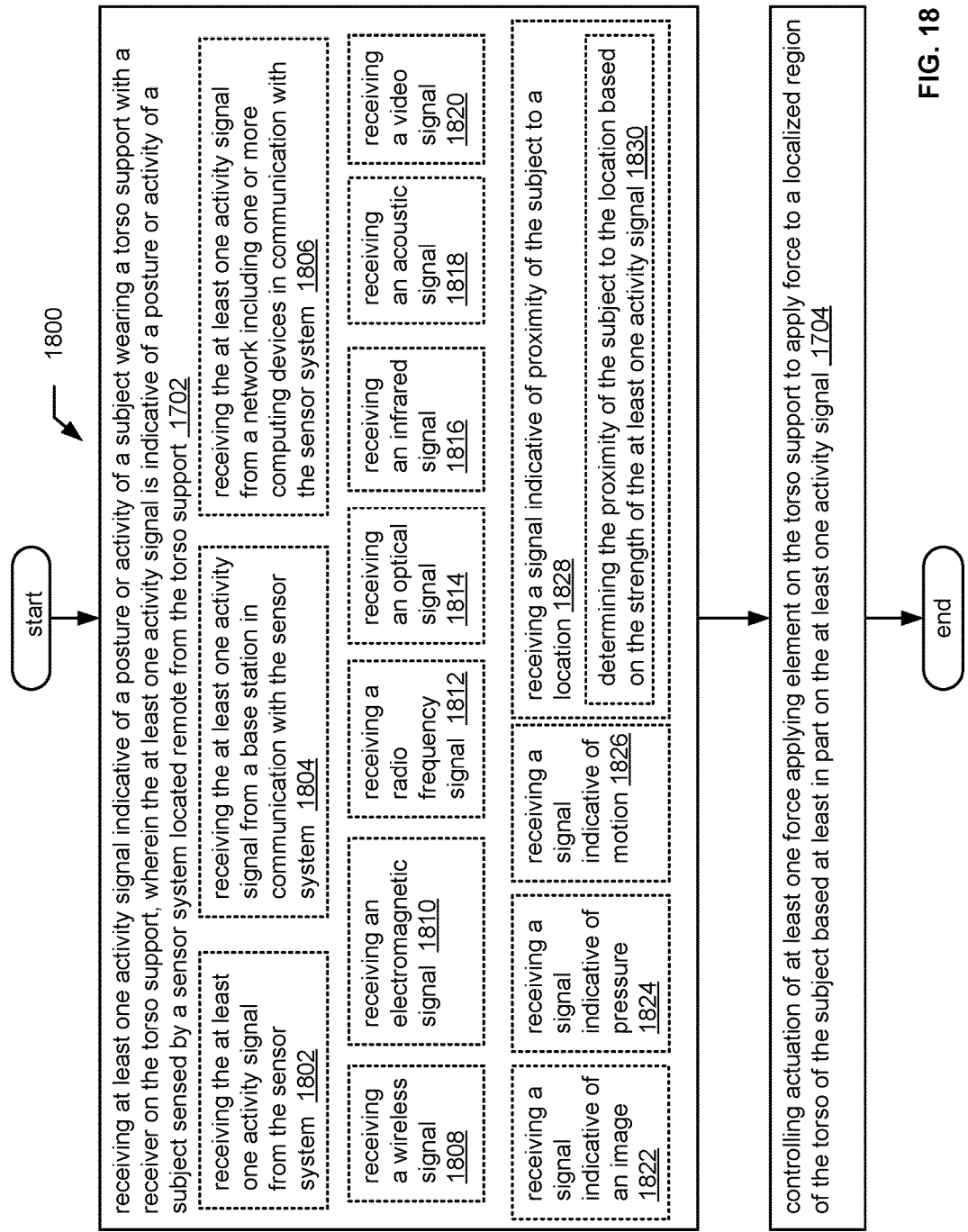
FIG. 18 is a flow diagram of a method of controlling a torso support.

Further method aspects are shown in FIG. 18. Here and elsewhere, steps 1702 and 1704 are as described in connection with FIG. 17. In an aspect, a method 1800 includes receiving the at least one activity signal from the sensor system, as indicated at 1802. Such method can be carried out, for example, with a system as depicted in FIG. 11. In another aspect a method includes receiving the at least one activity signal from a base station in communication with the sensor system, as indicated at 1804. Such method can be carried out, for example, with a system as depicted in FIG. 14. In another aspect, a method includes receiving the at least one activity signal from a network including one or more computing devices in communication with the sensor system, as indicated at 1806. Such method can be carried out, for example, with a system as depicted in FIG. 13. As indicated in FIG. 18, in an aspect receiving the at least one activity signal includes receiving a wireless signal, at 1808, which may be, for example, an electromagnetic signal 1810, a radio frequency signal 1812, an optical signal 1814, an infrared signal 1816, or an acoustic signal 1818. Receiving the at least one activity signal may include receiving a video signal 1820 (e.g., from a video camera), a signal indicative of an image 1822 (e.g., an image signal, processed image signal, or other signal containing image data or other representation of an image), a signal indicative of pressure 1824, motion 1826, or proximity of the subject to a location 1828. For example, the method can include determining the proximity of the subject to the location based on the strength of the at least one activity signal, as indicated at 1830.

Figure 19:
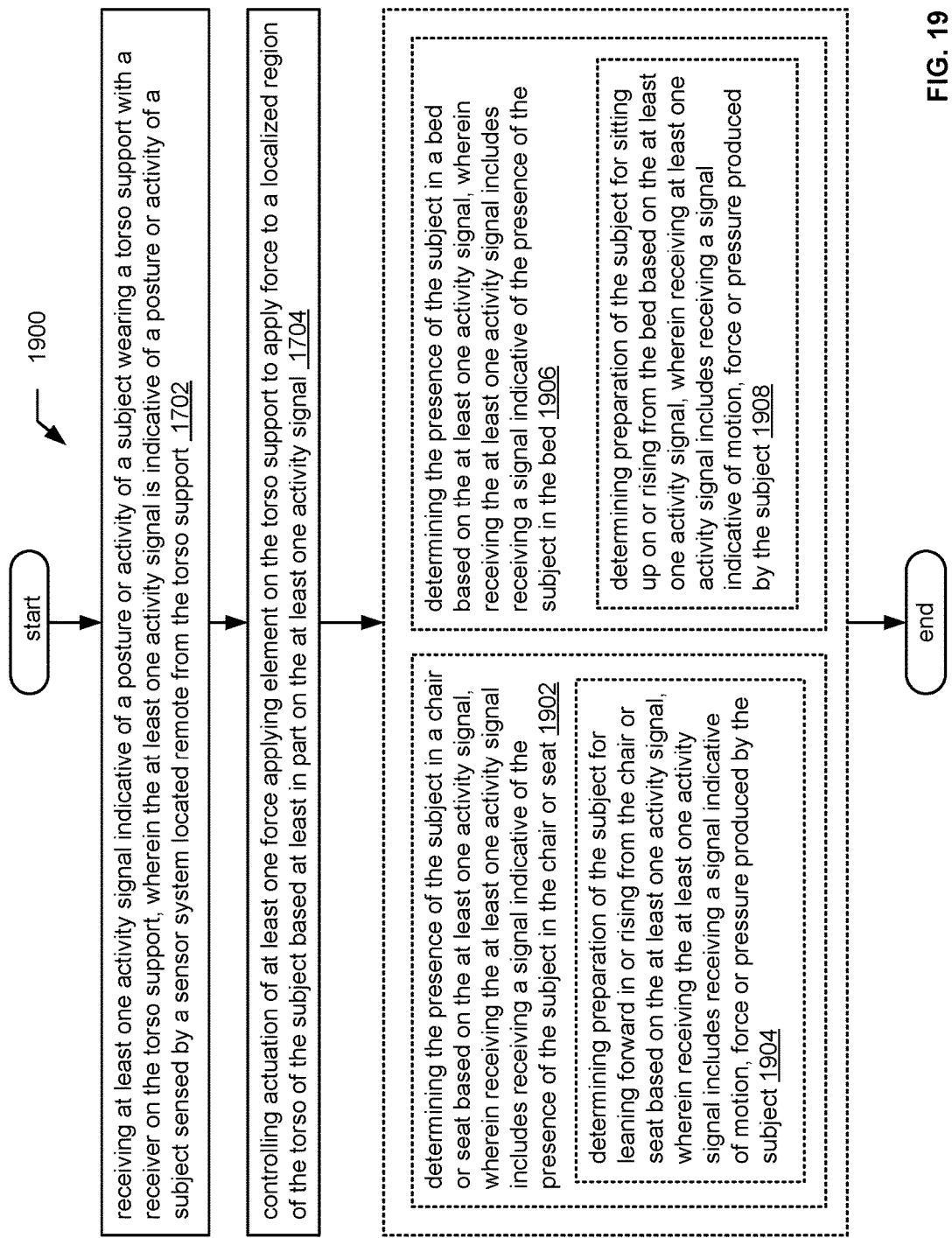
FIG. 19 is a flow diagram of a method of controlling a torso support.

FIG. 19 depicts further aspects of the method of FIG. 17. In an aspect, a method 1900 includes determining the presence of the subject in a chair or seat based on the at least one activity signal, wherein receiving the at least one activity signal includes receiving a signal indicative of the presence of the subject in the chair or seat, as indicated at 1902. In various aspects, a signal from a pressure sensor, force sensor, temperature sensor, motion sensor, or vibration sensor, located in or on a portion of the chair or seat could be used to detect whether the subject was in the chair or seat. For example, sensor 1020c in FIGS. 10 and 11 produces a signal indicative of the presence of the subject in chair 1106. Method 1900 may also include determining preparation of the subject for leaning forward in or rising from the chair or seat based on the at least one activity signal, wherein receiving the at least one activity signal includes receiving a signal indicative of motion, force or pressure produced by the subject, at 1904. Referring again to the embodiment depicted in FIGS. 10 and 11, sensors 1020a and 1020b on the arms of chair 1106 can be activated when the subject presses down on them, indicating preparation of the subject to rise from chair 1106. In other aspects, in the system depicted in FIG. 15, camera 1520 can be used to obtain an image of subject 1506 that can be analyzed to determine whether subject 1506 is present in chair 1538, and/or whether subject 1506 is leaning forward or making other movements that indicate preparation to rise from chair 1538.

In another aspect, method 1900 as shown in FIG. 19 includes determining the presence of the subject in a bed based on the at least one activity signal as indicated at 1906, wherein receiving the at least one activity signal includes receiving a signal indicative of the presence of the subject in the bed. For example, a signal from pressure sensor, force sensor, temperature sensor, motion sensor, or vibration sensor, located in or on a portion of the bed could be used to detect whether the subject was in the bed. In addition, method 1900 may include determining preparation of the subject for sitting up on or rising from the bed based on the at least one activity signal, wherein receiving at least one activity signal includes receiving a signal indicative of motion, force or pressure produced by the subject, as indicated at 1908. For example, when the subject wishes to sit up or rise from the bed, the subject may grasp a bed rail 1434 (as depicted in FIG. 14), or place his or her hand(s) on the edge of the bed to help support his or her body and reduce strain on his or her back. Therefore, preparation of the subject for sitting up or rising may be indicated by a signal from force, pressure sensor, motion sensor, or vibration sensor, located in or on a bedrail, headboard, edge of the bed, or other portion of the bed that is loaded by the subject in preparation for and/or during sitting up in or rising from the bed.

Figure 20:
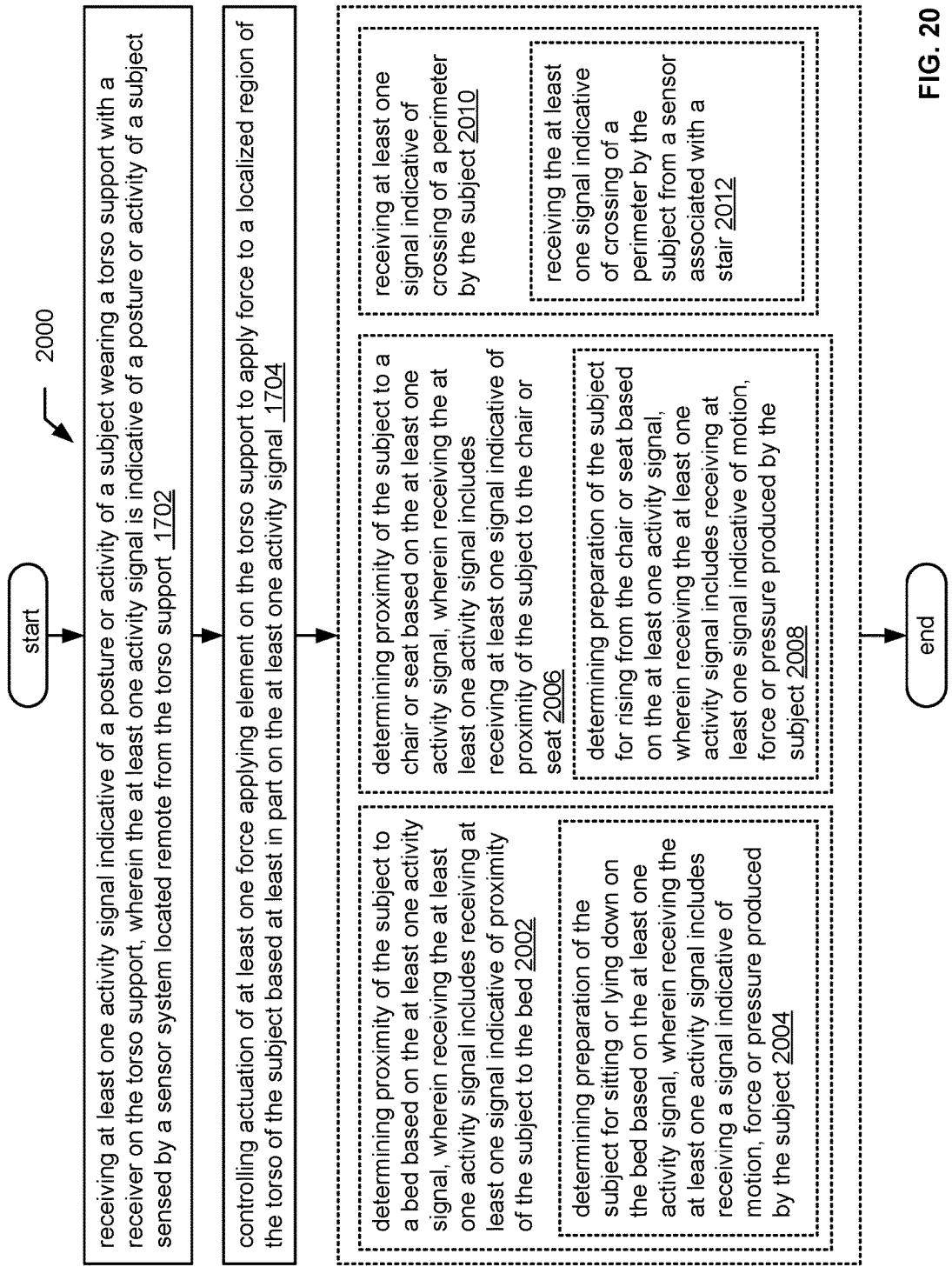
FIG. 20 is a flow diagram of a method of controlling a torso support.

A shown in FIG. 20, in an aspect a method 2000 includes determining proximity of the subject to a bed based on the at least one activity signal, wherein receiving the at least one activity signal includes receiving at least one signal indicative of proximity of the subject to the bed, as indicated at 2002. In addition, the method includes determining preparation of the subject for sitting or lying down on the bed based on the at least one activity signal, wherein receiving the at least one activity signal includes receiving a signal indicative of motion, force or pressure produced by the subject at 2004.

Alternatively, or in addition, method 2000 includes determining proximity of the subject to a chair or seat based on the at least one activity signal, wherein receiving the at least one activity signal includes receiving at least one signal indicative of proximity of the subject to the chair or seat, as indicated at 2006. In addition, method 2000 may include determining preparation of the subject for rising from the chair or seat based on the at least one activity signal, wherein receiving the at least one activity signal includes receiving at least one signal indicative of motion, force or pressure produced by the subject, as indicated at 2008.

In another aspect, receiving the at least one activity signal includes receiving at least one signal indicative of crossing of a perimeter by the subject, as indicated at 2010. For example, method 2000 may include receiving the at least one signal indicative of crossing of a perimeter by the subject from a sensor associated with a stair 2012, e.g., as depicted in FIG. 13.

Figure 21:
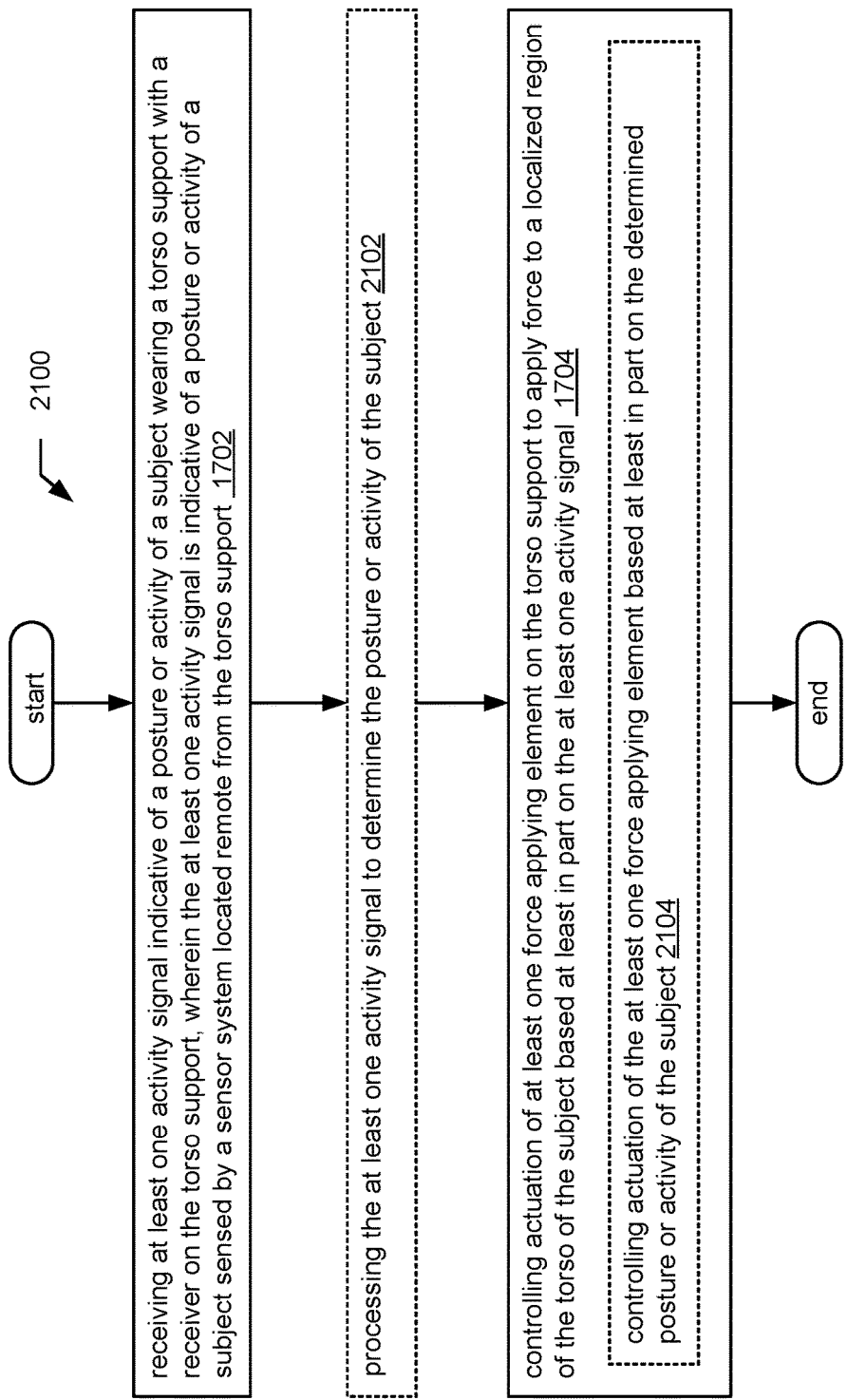
FIG. 21 is a flow diagram of a method of controlling a torso support.

As shown in FIG. 21, in an aspect, a method 2100 includes processing the at least one activity signal to determine the posture or activity of the subject, at 2102. Method 2100 can then include controlling actuation of the at least one force applying element based at least in part on the determined posture or activity of the subject, as indicated at 2104. Determined posture or activity can be obtained as described in connection with FIG. 12, for example.

Figure 22:
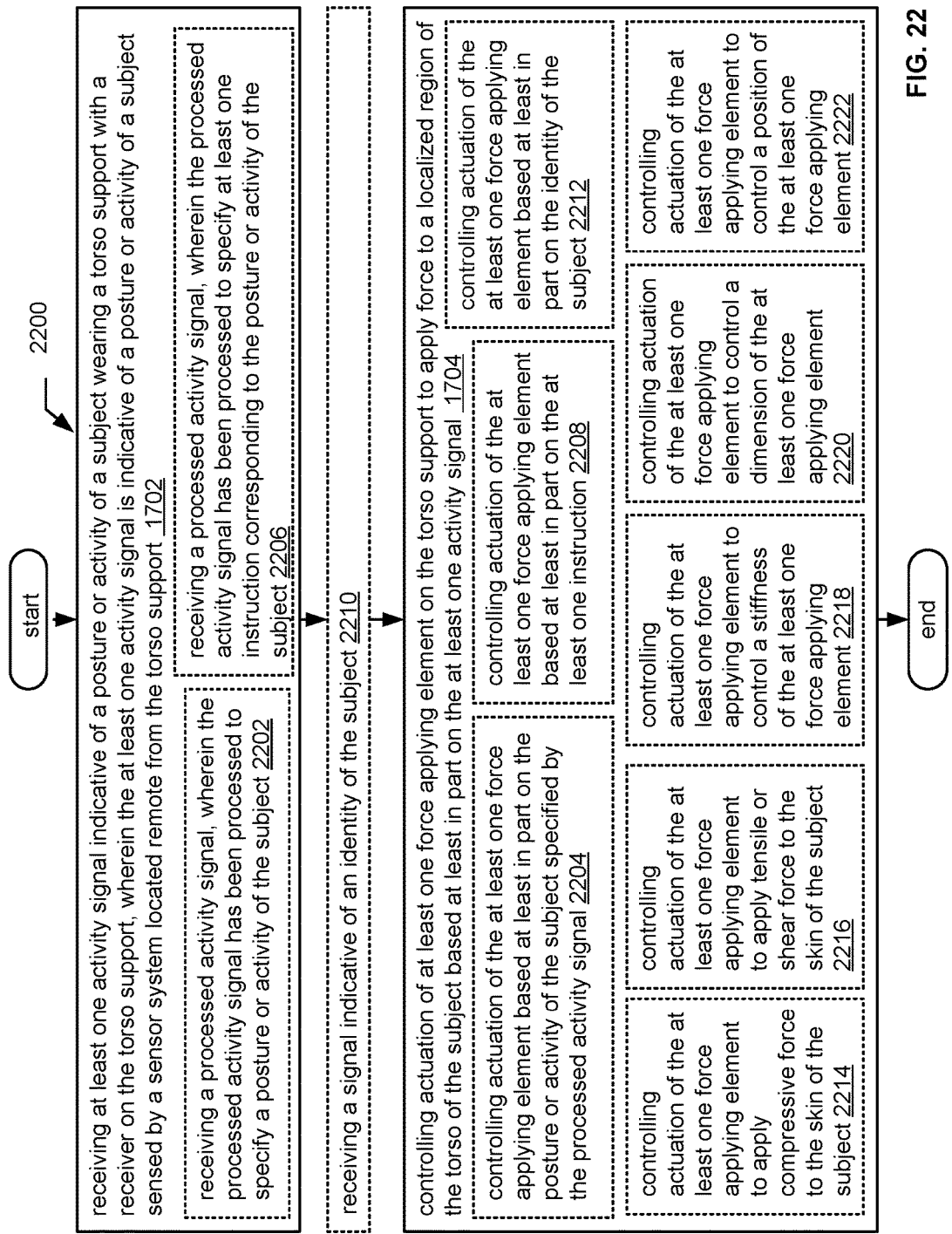
FIG. 22 is a flow diagram of a method of controlling a torso support.

In another aspect, as shown in FIG. 22, in related method 2200, receiving the at least one activity signal includes receiving a processed activity signal, wherein the processed activity signal has been processed to specify a posture or activity of the subject, as indicated at 2202. In connection therewith, method 2200 includes controlling actuation of the at least one force applying element based at least in part on the posture or activity of the subject specified by the processed activity signal, as indicated at 2204.

In another aspect of method 2200, receiving the at least one activity signal includes receiving a processed activity signal, wherein the processed activity signal has been processed to specify at least one instruction corresponding to the posture or activity of the subject, as indicated at 2206. In connection therewith, method includes controlling actuation of the at least one force applying element based at least in part on the at least one instruction, as indicated at 2208. The use of a processed activity signal that specifies the posture or activity of the subject, or an instruction corresponding to the posture or activity of the subject, is described in connection with FIG. 12.

In yet another aspect, method 2200 includes receiving a signal indicative of an identity of the subject, at 2210, and subsequently controlling actuation of the at least one force applying element based at least in part on the identity of the subject, at 2212, as described in connection with FIG. 12.

In various aspects, method 2200 includes controlling actuation of the at least one force applying element to apply compressive force to the skin of the subject, at 2214, apply tensile or shear force to the skin of the subject, at 2216, control a stiffness of the at least one force applying element, at 2218, control a dimension of the at least one force applying element, at 2220, or control a position of the at least one force applying element, at 2222.

Figure 23:
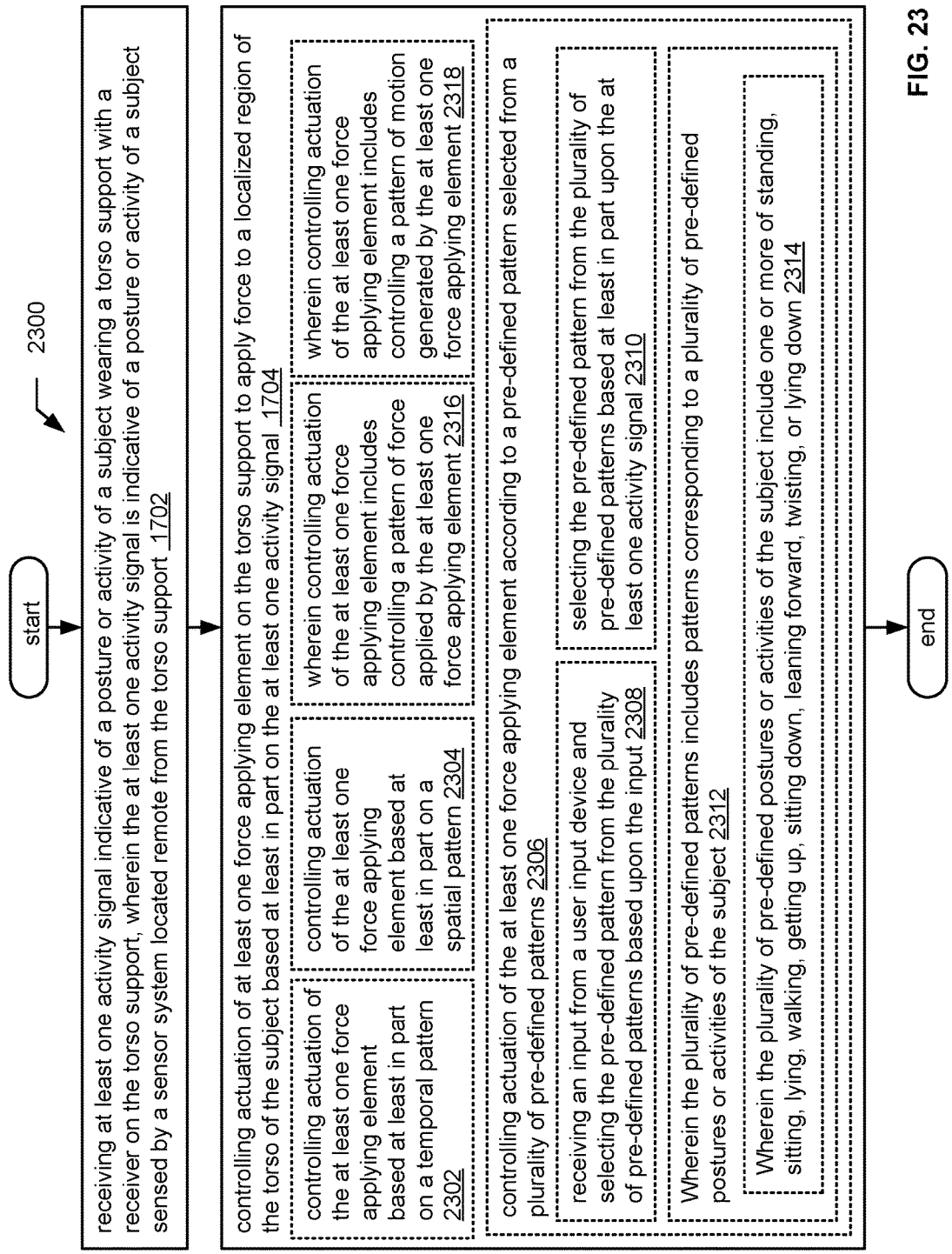
FIG. 23 is a flow diagram of a method of controlling a torso support.

FIG. 23 illustrates a method 2300 including aspects relating to controlling actuation of the at least one force applying element according to patterns. In an aspect, method 2300 includes controlling actuation of the at least one force applying element based at least in part on a temporal pattern, as indicated at 2302. In an aspect, method 2300 includes controlling actuation of the at least one force applying element based at least in part on a spatial pattern, at 2304. It will be appreciated that force and motion may be related, depending upon the mechanical properties of the torso support and the portion of the body of the subject to which force is applied, but that either force or motion (or a parameter derived therefrom) may be measured and used as a control parameter.

In an aspect, method 2300 includes controlling actuation of the at least one force applying element according to a pre-defined pattern selected from a plurality of pre-defined patterns, as indicated at 2306. Method 2300 may include receiving an input from a user input device and selecting the pre-defined pattern from the plurality of pre-defined patterns based upon the input, as indicated at 2308, selecting the pre-defined pattern from the plurality of pre-defined patterns based at least in part upon the at least one activity signal, as indicated at 2310, or a combination thereof. The plurality of pre-defined patterns may include patterns corresponding to a plurality of pre-defined postures or activities of the subject, as indicated at 2312, which may include, for example, one or more of standing, sitting, lying, walking, getting up, sitting down, leaning forward, twisting, or lying down, as indicated at 2314.

Controlling actuation of the at least one force applying element can include controlling a pattern of force applied by the at least one force applying element, as indicated at 2316, or controlling a pattern of motion generated by the at least one force applying element, as indicated at 2318.

Figure 24:
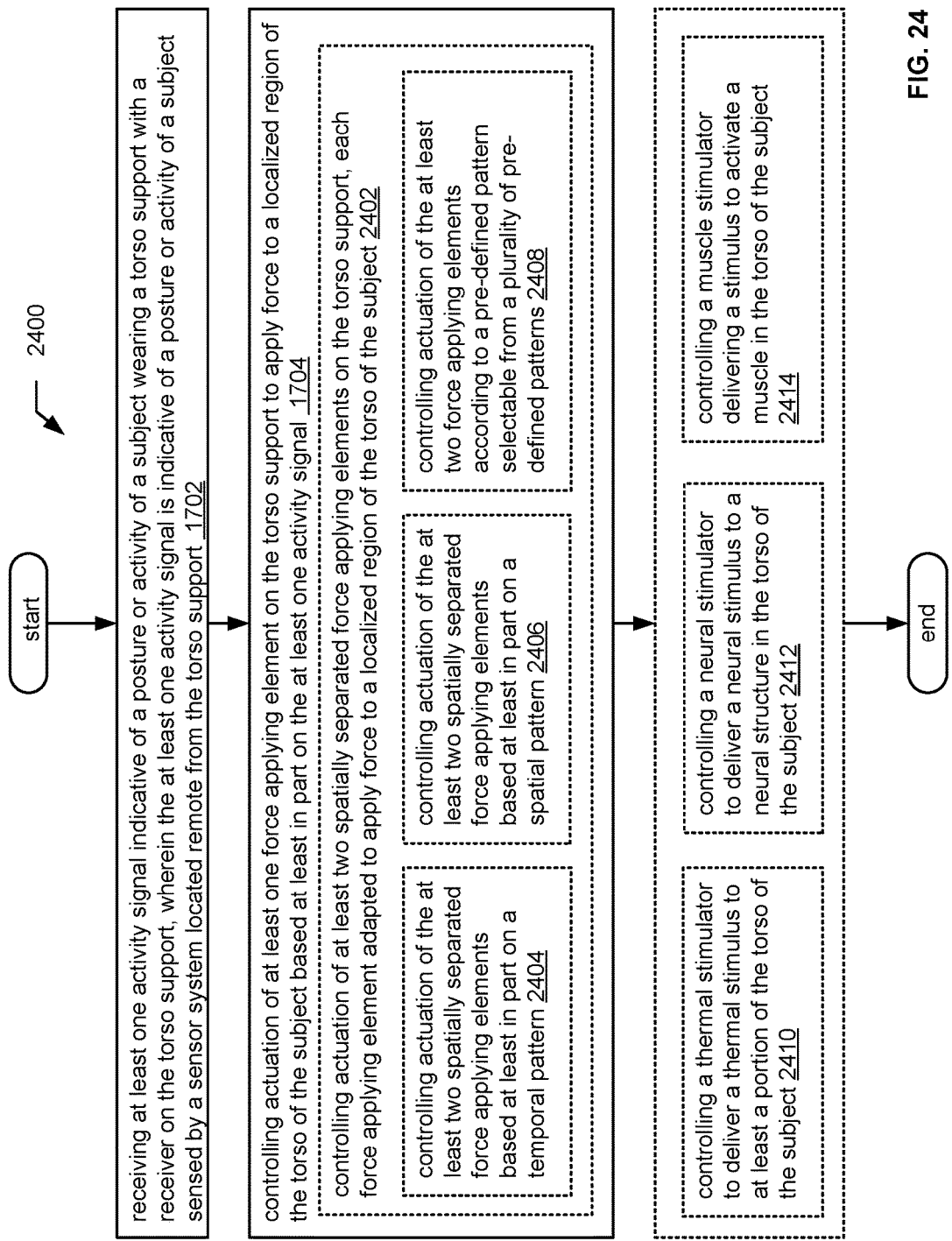
FIG. 24 is a flow diagram of a method of controlling a torso support.

In another aspect, as shown in FIG. 24, a method 2400 includes controlling actuation of at least two spatially separated force applying elements on the torso support, each force applying element adapted to apply force to a localized region of the torso of the subject, as indicated at 2402. For example, method 2400 may include controlling actuation of the at least two spatially separated force applying elements based at least in part on a temporal pattern, as indicated at 2404, or controlling actuation of the at least two spatially separated force applying elements based at least in part on a spatial pattern, as indicated at 2406, or both. In an aspect, method 2400 includes controlling actuation of the at least two force applying elements according to a pre-defined pattern selectable from a plurality of pre-defined patterns, as indicated at 2408. Controlling actuation according to a pre-defined pattern may be generally as described in connection with FIG. 23, for example.

In further aspects, method 2400 includes controlling a thermal stimulator to deliver a thermal stimulus to at least a portion of the torso of the subject, at 2410, controlling a neural stimulator to deliver a neural stimulus to a neural structure in the torso of the subject, at 2412, and/or controlling a muscle stimulator to deliver a stimulus to activate a muscle in the torso of the subject, at 2414.

In various embodiments, methods as described herein may be performed according to instructions implementable in hardware, software, and/or firmware. Such instructions may be stored in non-transitory machine-readable data storage media, for example. Those having skill in the art will recognize that the state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware in one or more machines, compositions of matter, and articles of manufacture, limited to patentable subject matter under 35 § USC 101. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

In some implementations described herein, logic and similar implementations may include software or other control structures. Electrical circuitry, for example, may have one or more paths of electrical current constructed and arranged to implement various functions as described herein. In some implementations, one or more media may be configured to bear a device-detectable implementation when such media hold or transmit device detectable instructions operable to perform as described herein. In some variants, for example, implementations may include an update or modification of existing software or firmware, or of gate arrays or programmable hardware, such as by performing a reception of or a transmission of one or more instructions in relation to one or more operations described herein. Alternatively or additionally, in some variants, an implementation may include special-purpose hardware, software, firmware components, and/or general-purpose components executing or otherwise invoking special-purpose components.

Implementations may include executing a special-purpose instruction sequence or invoking circuitry for enabling, triggering, coordinating, requesting, or otherwise causing one or more occurrences of virtually any functional operations described herein. In some variants, operational or other logical descriptions herein may be expressed as source code and compiled or otherwise invoked as an executable instruction sequence. In some contexts, for example, implementations may be provided, in whole or in part, by source code, such as C++, or other code sequences. In other implementations, source or other code implementation, using commercially available and/or techniques in the art, may be compiled/implemented/translated/converted into a high-level descriptor language (e.g., initially implementing described technologies in C or C++ programming language and thereafter converting the programming language implementation into a logic-synthesizable language implementation, a hardware description language implementation, a hardware design simulation implementation, and/or other such similar mode(s) of expression). For example, some or all of a logical expression (e.g., computer programming language implementation) may be manifested as a Verilog-type hardware description (e.g., via Hardware Description Language (HDL) and/or Very High Speed Integrated Circuit Hardware Descriptor Language (VHDL)) or other circuitry model which may then be used to create a physical implementation having hardware (e.g., an Application Specific Integrated Circuit). Those skilled in the art will recognize how to obtain, configure, and optimize suitable transmission or computational elements, material supplies, actuators, or other structures in light of these teachings.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof, limited to patentable subject matter under 35 U.S.C. § 101. In an embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, limited to patentable subject matter under 35 U.S.C. § 101, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to non-transitory machine-readable data storage media such as a recordable type medium such as a floppy disk, a hard disk drive, a Compact Disc (CD), a Digital Video Disk (DVD), a digital tape, a computer memory, etc. A signal bearing medium may also include transmission type medium such as a digital and/or an analog communication medium (e.g., a fiber optic cable, a waveguide, a wired communications link, a wireless communication link (e.g., transmitter, receiver, transmission logic, reception logic, etc.) and so forth).

FIG. 25 depicts an article of manufacture 2500 that includes one or more non-transitory machine-readable data storage media 2502 bearing one or more instructions 2504 for receiving at least one activity signal indicative of a posture or activity of a subject wearing a torso support with a receiver on the torso support, wherein the at least one activity signal is indicative of a posture or activity of a subject sensed by a sensor system located remote from the torso support; and controlling actuation of at least one force applying element on the torso support to apply force to a localized region of the torso of the subject based at least in part on the at least one activity signal.

Instructions 2504 depicted in FIG. 25 correspond to the method 1700 shown in FIG. 17. Other variants of methods as depicted in FIGS. 9-24 and as described herein can be implemented through the use of non-transitory machine-readable data storage media bearing one or more suitable instructions.

In an aspect, the one or more non-transitory machine-readable data storage media 2502 bear one or more instructions for carrying out the variants of method 900 as shown in FIG. 9, e.g., receiving the at least one activity signal from the sensor system, one or more instructions for receiving the at least one activity signal from a base station in communication with the sensor system, or one or more instructions for receiving the at least one activity signal from a network including one or more computing devices in communication with the sensor system, receiving a video signal, receiving a signal indicative of an image, receiving a signal indicative of pressure, receiving a signal indicative of motion, or receiving a signal indicative of proximity of the subject to a location, and/or additionally determining the proximity of the subject to the location based on the strength of the at least one activity signal.

In an aspect, the one or more non-transitory machine-readable data storage media 2502 bear one or more instructions for carrying out the variants of method 1900 as shown in FIG. 19, e.g., one or more instructions for determining the presence of the subject in a bed based on the at least one activity signal, wherein the one or more instructions for receiving the at least one activity signal include one or more instructions for receiving a signal indicative of the presence of the subject in a bed, optionally in combination with one or more instructions for determining preparation of the subject for sitting up on or rising from the bed based on the at least one activity signal, wherein the one or more instructions for receiving the at least one activity signal include one or more instructions for receiving a signal indicative of motion, force or pressure produced by the subject, and/or one or more instructions for determining the presence of the subject in a chair or seat based on the at least one activity signal, wherein the one or more instructions for receiving the at least one activity signal include one or more instructions for receiving a signal indicative of the presence of the subject in the chair or seat, optionally in combination with one or more instructions for determining preparation of the subject for leaning forward in or rising from the chair or seat, wherein the one or more instructions for receiving the at least one activity signal include one or more instructions for receiving a signal indicative of motion, force or pressure produced by the subject.

In an aspect, the one or more non-transitory machine-readable data storage media 2502 bear one or more instructions for carrying out the variants of method 2000 as shown in FIG. 20, e.g., one or more instructions for determining proximity of the subject to a bed based on the at least one activity signal, wherein the one or more instructions for receiving the at least one activity signal include one or more instructions for receiving a signal indicative of the proximity of the subject to a bed, optionally with one or more instructions for determining preparation of the subject for sitting or lying down on the bed, wherein the one or more instructions for receiving the at least one activity signal include one or more instructions for receiving a signal indicative of motion, force or pressure produced by the subject; one or more instructions for receiving at least one activity signal indicative of the proximity of the subject to a chair or seat, optionally with one or more instructions for receiving at least one activity signal indicative of motion, force or pressure produced by the subject, the motion, force or pressure indicative of preparation of the subject for rising from the chair or seat; and/or one or more instructions for determining crossing of a perimeter by the subject, wherein the one or more instructions for receiving the at least one activity signal include one or more instructions for receiving a signal indicative of crossing of the perimeter by the subject.

In an aspect, the one or more non-transitory machine-readable data storage media 2502 bear one or more instructions for carrying out the variants of method 2100 as shown in FIG. 21, e.g., one or more instructions for processing the at least one activity signal to determine the posture or activity of the subject, and one or more instructions for controlling actuation of the at least one force applying element based at least in part on the determined posture or activity of the subject.

In an aspect, the one or more non-transitory machine-readable data storage media 2502 bear one or more instructions for carrying out the variants of method 2200 as shown in FIG. 22, e.g., one or more instructions for receiving a processed activity signal that specifies the posture or activity of the subject from the at least one sensor system, wherein the processed activity signal has been processed by the at least one sensor system to specify a posture or activity of the subject, and one or more non-transitory machine-readable data storage media bear one or more instructions for controlling actuation of the at least one force applying element based at least in part on the posture or activity of the subject specified by the processed activity signal. Alternatively, or in addition, the one or more non-transitory machine-readable data storage media 2502 may bear one or more instructions for receiving a processed activity signal specifying at least one instruction corresponding to the posture or activity of the subject, or one or more instructions for receiving a signal indicative of an identity of the subject, as well as one or more instructions for controlling actuation of the at least one force applying element based at least in part on the identity of the subject. The one or more non-transitory machine-readable data storage media 2502 may bear one or more instructions for carrying out various addition aspects as depicted in FIG. 22, e.g., controlling actuation of the at least one force applying element to apply compressive force to the skin of the subject, controlling actuation of the at least one force applying element to apply tensile or shear force to the skin of the subject, controlling actuation of the at least one force applying element to control a stiffness of the at least one force applying element, controlling actuation of the at least one force applying element to control a dimension of the at least one force applying element, and controlling actuation of the at least one force applying element to control a position of the at least one force applying element.

In an aspect, the one or more non-transitory machine-readable data storage media 2502 bear one or more instructions for carrying out the variants of method 2300 as shown in FIG. 23, e.g., one or more instructions for controlling actuation of the at least one force applying element based at least in part on a temporal pattern, one or more instructions for controlling actuation of the at least one force applying element based at least in part on a spatial pattern, one or more instructions for controlling actuation of the at least one force applying element by controlling a pattern of force applied by the at least one force applying element, or one or more instructions for controlling actuation of the at least one force applying element by controlling a pattern of motion generated by the at least one force applying element. The one or more non-transitory machine-readable data storage media 2502 may bear one or more instructions for controlling actuation of the at least one force applying element according to a pre-defined pattern selected from a plurality of pre-defined patterns, possibly in combination with one or more instructions for receiving an input from a user input device and selecting the pre-defined pattern from the plurality of pre-defined patterns based upon the input, and/or one or more instructions for selecting the pre-defined pattern from the plurality of pre-defined patterns based at least in part upon the at least one activity signal. As discussed herein above, the plurality of pre-defined patterns includes patterns corresponding to a plurality of pre-defined postures or activities of the subject, e.g., standing, sitting, lying, walking, getting up, sitting down, or lying down.

In an aspect, the one or more non-transitory machine-readable data storage media 2502 bear one or more instructions for carrying out the variants of method 2400 as shown in FIG. 24, e.g., one or more instructions for controlling actuation of at least two spatially separated force applying elements on the torso support, each of the at least two spatially separated force applying elements adapted to apply force to a localized region of the torso of the subject. The one or more instructions for controlling actuation of the at least two spatially separated force applying elements on the torso support may include one or more instructions for controlling actuation of the at least two spatially separated force applying elements based at least in part on a temporal pattern, at least in part on a spatial pattern, or according to a pre-defined pattern selectable from a plurality of pre-defined patterns. In addition, the one or more non-transitory machine-readable data storage media may bear one or more instructions for controlling a thermal stimulator to deliver a thermal stimulus to at least a portion of the torso of the subject, one or more instructions for controlling a neural stimulator to deliver a neural stimulus to a neural structure in the torso of the subject, and/or one or more instructions for controlling a muscle stimulator to deliver a stimulus to activate a muscle in the torso of the subject.

Elements of the systems depicted in FIGS. 1 and 4 and FIGS. 10-16 can be combined to form other variations of controllable active torso support system or other active wearable systems. For example, in an aspect a system includes one or more sensors as depicted and described in connection with FIGS. 1 and 4 as well as one or more sensors as depicted and described in connection with FIGS. 10-16. Components worn on the torso as well as components worn on other parts of the body may incorporate various types of sensors, force-applying elements, stimulators (e.g., thermal, neural, or muscle stimulators), and/or feedback devices (e.g., haptic devices, audio, or visual feedback devices). In addition, components worn on the body may be operably connected to sensors in the environment of the subject.

As discussed herein above, in some aspects, systems as described herein are operably connected to and include the capability to transmit signals to and receive signals from computing and/or communication networks. Processing of data to control force-applying elements, stimulators, and/or feedback devices can be performed by electrical control circuitry located on the torso support or other wearable item, or in local or remote portions of a computing or communication network. Signals may contain sensed data from any of the various types of sensors described herein, pertaining to gait, posture, or motion of the subject, muscle or nerve activity, or parameters such as temperature. Sensed data may include raw or processed data, or information derived therefrom.

In various aspects, sensed data is processed to evaluate the gait, posture, or motion of the subject, e.g., to determine if one or more aspect of the gait, posture, or motion is 'good' or 'bad,' and/or to determine a deviation of all or a portion of the gait, posture, or motion from a desirable gait, posture, or motion. Force applying elements may be activated in an appropriate pattern, as discussed herein above, to provide support to the torso or other body portions responsive to the determined gait, posture, or motion, or to constrain movement in a pattern determined to improve the gait, posture, or motion of the subject. In an aspect, muscle or nerve stimulation are provided to modify muscle activation in a pattern determined to improve the gait, posture, or motion of the subject. In an aspect, feedback can be provided to the subject, based on the sensed data, to notify the subject of the need to voluntarily correct gait, posture, or motion. Feedback can be provided in real-time (while the subject is actively performing or engaged in the gait, posture, or motion), and take the form of a haptic, audio or visual notification or alarm. In some aspects, feedback can take the form of an evaluation or recommendation (presented in visual or audio form) regarding the gait, posture or motion or correction or improvement thereto. The evaluation or recommendation can be provided to the subject, and/or alternatively, or in addition, be provided to another party, for example a medical care provider, a physical therapist, a coach, a trainer, or any other individual working with the subject to correct or improve gait, posture, or movement, or having an interest in the gait, posture, or movement of the subject. Such an evaluation or recommendation can be provided via a computing/communication system (e.g., a computer, tablet computer, smart phone, entertainment device) including a display and/or speaker operably connected thereto.

In an aspect, sensed data (raw or processed) is compared to one or more template representing desirable or target values for gait, posture, or motion (or conversely, one or more templates representing undesirable or to-be-avoided values for gait, posture, or motion). Such comparison can be based on windowing, thresholding or distance measurements (e.g., least-squares), for example. For example, values that are within a window, above (or below) a threshold, or within a specified distance from the template values are deemed to be 'good', while values that not are deemed to be 'bad.' In an aspect, the amount of deviation from the template can also be determined. Template values can be based on selected data measured from the subject, or from one or more other individuals. Template values can reflect pooled (e.g., averaged) values from a population of individuals. In an aspect, the subject or other user can provide an input via a user interface to select one or more particular instance of data representing a gait, posture, or motion as an exemplar or template of a desirable gait, posture, or motion. Controlling a wearable system such as a torso support to provide muscle/joint support, muscle activation, and/or feedback to a subject in response to sensed gait, posture, or motion can be used in health, medical, therapeutic, or physical training contexts to prevent or minimize discomfort or injury, or to improve performance in activities in which gait, posture, or motion is of importance.

The herein described subject matter sometimes illustrates different components contained within, or connected with, different other components. It is to be understood that such depicted arrangements are merely exemplary, and that in fact many other arrangements may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components may be referred to herein as "configured to," "configured by," "configurable to," "operable/operative to," "adapted/adaptable," "able to," "conformable/conformed to," etc. Those skilled in the art will recognize that such terms (e.g., "configured to") generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

The invention claimed is:
1. A system comprising:
a wearable item including
a plurality of actuators, each actuator configured to be positioned with respect to a localized region of a body of a subject;
at least one landmark sensor adapted to sense a parameter indicative of a position of a landmark in or on the body of the subject and to produce at least one landmark position signal; and
at least one positioning element adapted to be worn on the body of the subject and to position the at least one landmark sensor and the plurality of actuators with respect to the body of the subject, wherein each of the plurality of actuators is in a known position relative to the wearable item;
at least one activity sensor adapted to detect an input indicative of a posture, gait or activity of the subject, and to generate an activity signal indicative of the posture, gait or activity of the subject; and
control circuitry including
electrical circuitry for receiving from the at least one landmark sensor the at least one landmark position signal;
electrical circuitry for receiving from the at least one activity sensor the at least one activity signal;
signal processing circuitry for calculating a position of a target region on the body of the subject relative to the wearable item based on the at least one landmark position signal and on a known position of the target region relative to the landmark;
signal processing circuitry for selecting at least one actuator positioned closest to the target region; and
electrical circuitry for generating an electrical control signal for controlling actuation of the at least one actuator based at least in part on the at least one activity signal.

2. The system of claim 1, wherein the signal processing circuitry for calculating the position of the target region on the body of the subject relative to the wearable item based on the at least one landmark position signal and on the known position of the target region relative to the landmark is configured to determine the position of the target region, wherein the target region is at the same location as the landmark.

3. The system of claim 2, wherein the signal processing circuitry for calculating the position of the target region on the body of the subject relative to the wearable item based on the at least one landmark position signal and on the known position of the target region relative to the landmark is configured to determine the position of the target region, wherein the target region is the landmark.

4. The system of claim 1, including one or more neural stimulator, muscle stimulator, or thermal stimulus source carried by the at least one positioning element.

5. The system of claim 1, wherein the at least one landmark sensor includes an electromagnetic transducer, an optical sensor, an infrared sensor, an acoustic sensor, an electrical transducer, a magnetic transducer, an ultrasound transducer, a micro-impulse radar sensor, or a temperature sensor.

6. The system of claim 1, wherein the at least one landmark sensor is configured to sense muscle activity or neural activity.

7. The system of claim 1, wherein the at least one landmark sensor is configured to sense a signal indicative of at least one of a bony structure within the body of the subject, a soft-tissue structure within the body of the subject, vasculature below a skin surface of the body of the subject, muscle activity, neural activity, a local temperature on or below the skin surface, a marker or fiducial, on or below the skin surface of the subject.

8. The system of claim 1, wherein the at least one activity sensor includes at least one force sensor, pressure sensor, capacitance sensor, conductance sensor, stress sensor, strain sensor, camera, motion sensor, proximity sensor, perimeter sensor, micro-impulse radar sensor, infrared sensor, optical sensor, electromagnetic sensor, acoustic sensor, accelerometer, gyro, inclinometer, magnetometer, or position sensor.

9. The system of claim 1, wherein the electrical circuitry for receiving from the at least one landmark sensor the at least one landmark position signal includes electrical circuitry located on the wearable item.

10. The system of claim 1, wherein the electrical circuitry for receiving from the at least one activity sensor the at least one activity signal includes a receiver for receiving the at least one activity signal from a remote activity sensor.

11. The system of claim 1, wherein the signal processing circuitry for calculating the position of the target region on the body of the subject relative to the wearable item based on the at least one landmark position signal and on the known position of the target region relative to the landmark is configured to determine the position of the target region, wherein the target region is at a different location than the landmark.

12. The system of claim 1, including a memory operably connected to the control circuitry, wherein the electrical circuitry for generating an electrical control signal for controlling actuation of the at least one actuator based at least in part on the at least one activity signal is configured to generate the electrical control signal based at least in part on a temporal pattern stored in the memory.

13. The system of claim 1, including a memory operably connected to the control circuitry, wherein the electrical circuitry for generating an electrical control signal for controlling actuation of the at least one actuator based at least in part on the at least one activity signal is configured to generate a plurality of control signals for controlling the plurality of actuators in a spatial and temporal pattern.

14. The system of claim 1, wherein one or more of the plurality of actuators has associated therewith an electrical sensor adapted to detect an electromyographic signal associated with muscle activity, wherein the electrical sensor is at least one of the at least one landmark sensor and the at least one activity sensor.

15. The system of claim 1, wherein the plurality of actuators includes one or more force applying element or haptic element.

16. The system of claim 1, wherein the at least one positioning element includes at least one of a garment, band, strap, belt or harness.

17. The system of claim 1, wherein the signal processing circuitry for selecting the at least one actuator positioned closest to the target region is configured to select the at least one actuator positioned at at least one of the shortest spatial distance from the target region and the shortest electrical distance from the target region.

* * * * *

UNITED STATES PATENT AND TRADEMARK OFFICE
CERTIFICATE OF CORRECTION

PATENT NO. : 10,314,733 B2
APPLICATION NO. : 15/161599
DATED : June 11, 2019
INVENTOR(S) : Roderick A. Hyde et al.

Page 1 of 1

It is certified that error appears in the above-identified patent and that said Letters Patent is hereby corrected as shown below:

On the Title Page

Item (71) Applicant: "Elwha LLC, Belleveue, WA (US)" should be --Elwha LLC, Bellevue, WA (US)--

Signed and Sealed this
Eleventh Day of February, 2020

Andrei Iancu
*Director of the United States Patent and Trademark Office*